US008005620B2

(12) United States Patent
Gustafsson et al.

(10) Patent No.: US 8,005,620 B2
(45) Date of Patent: Aug. 23, 2011

(54) SYSTEMS AND METHODS FOR BIOPOLYMER ENGINEERING

(75) Inventors: Claes Gustafsson, Belmont, CA (US); Sridhar Govindarajan, Redwood City, CA (US); Jeremy Stephen Minshull, Los Altos, CA (US)

(73) Assignee: DNA Twopointo Inc., Menlo Park, CA (US)

( * ) Notice: Subject to any disclaimer, the term of this patent is extended or adjusted under 35 U.S.C. 154(b) by 1395 days.

(21) Appl. No.: 10/566,953

(22) PCT Filed: Jul. 30, 2004

(86) PCT No.: PCT/US2004/024752
§ 371 (c)(1),
(2), (4) Date: Jan. 31, 2006

(87) PCT Pub. No.: WO2005/013090
PCT Pub. Date: Feb. 10, 2005

(65) Prior Publication Data
US 2006/0136184 A1    Jun. 22, 2006

Related U.S. Application Data

(60) Provisional application No. 60/491,815, filed on Aug. 1, 2003, provisional application No. 60/536,357, filed on Jan. 14, 2004, provisional application No. 60/536,862, filed on Jan. 15, 2004.

(51) Int. Cl.
*G01N 33/48* (2006.01)
*G06G 7/58* (2006.01)
*G06F 7/60* (2006.01)
*G06F 17/00* (2006.01)

(52) U.S. Cl. ............... 702/19; 702/20; 703/2; 703/11; 700/90

(58) Field of Classification Search ............... None
See application file for complete search history.

(56) References Cited

U.S. PATENT DOCUMENTS

| | | |
|---|---|---|
| 5,843,708 A | 12/1998 | Hardman et al. |
| 7,117,096 B2 | 10/2006 | Luo et al. |
| 2002/0048772 A1 | 4/2002 | Dahiyat et al. |
| 2002/0119492 A1 | 8/2002 | Chirno et al. |
| 2002/0177170 A1 | 11/2002 | Luo et al. |
| 2004/0072245 A1 | 4/2004 | Gustafsson et al. |
| 2004/0161796 A1 | 8/2004 | Gustafsson et al. |
| 2006/0136184 A1 | 6/2006 | Gustafsson et al. |
| 2006/0205003 A1 | 9/2006 | Gustafsson et al. |
| 2007/0239364 A1 | 10/2007 | Fox |
| 2008/0050357 A1 | 2/2008 | Gustafsson et al. |

FOREIGN PATENT DOCUMENTS

| | | |
|---|---|---|
| WO | WO 03/075129 A2 | 9/2003 |
| WO | PCT/US2004/024752 | 7/2004 |
| WO | WO 2005/012877 A2 | 2/2005 |
| WO | WO 2005/013090 A3 | 2/2005 |

OTHER PUBLICATIONS

Fox et al., 2003, "Optimizing the search algorithm for protein engineering by directed evolution," Protein Engineering vol. 16: 589-597.
Gustafsson et al., 2003, "Putting engineering back into protein engineering: bioinformatic approaches to catalyst design," Current Opinion in Biotechnology 14: 366-370.
Gustafsson et al., 2001, "Exploration of sequence space for protein engineering," Journal of Molecular Recognition 14: 308-314.
Hayes et al., 2002, "Combining computational and experimental screening for rapid optimization of protein properties," PNAS 99: 15926-15931.
Schneider et al., 1998, "Peptide design by artificial neural networks and computer-based evolutionary," Biochemistry, vol. 95, Issue 21, pp. 12179-12184.
Adenot et al., 1999, "Peptides quantitative structure-function relationships: An automated mutation strategy to design peptides and pseudopeptides from substitution matrices," Journal of Molecular Graphics and Modeling 17, 292-309.
Damborský, Jiří, 1998, "Quantitative structure-function and structure-stability relationships of purposely modified proteins," Protein Engineering 11, 21-30.
Del Sol Mesa et al., 2003, "Automatic Methods for Predicting Functionally Important Residues," J. Mol. Biol. 326, 1289-1302.
Fariselli et al., 2002, "Prediction of protein-protein interaction sites in heterocomplexes with neural networks," Eur. J. Biochem 269, 1356-1361.
Govindarajan et al., 2003, "Systematic Variation of Amino Acid Substitutions for Stringent Assessment of Pairwise Covariation," J. Mol. Biol. 328, 1061-1069.
Hellberg et al., 1986, "Peptide Quantitative Structure-Activity Relationships, a Multivariate Approach," J. Med. Chem 30, 1126-1135.

(Continued)

*Primary Examiner* — Shubo Zhou
(74) *Attorney, Agent, or Firm* — Jones Day; Brett Lovejoy

(57) ABSTRACT

Methods, computer systems, and computer program products for biopolymer engineering. A variant set for a biopolymer of interest is constructed by identifying, using a plurality of rules, a plurality of positions in the biopolymer of interest and, for each respective position in the plurality of positions, substitutions for the respective position. The plurality of positions and the substitutions for each respective position in the plurality of positions collectively define a biopolymer sequence space. A variant set comprising a plurality of variants of the biopolymer of interest is selected. A property of all or a portion of the variants in the variant set is measured. A sequence-activity relationship is modeled between (i) one or more substitutions at one or more positions of the biopolymer of interest represented by the variant set and (ii) the property measured for all or the portion of the variants in the variant set. The variant set is redefined to comprise variants that include substitutions in the plurality of positions that are selected based on a function of the sequence-activity relationship.

44 Claims, 29 Drawing Sheets

OTHER PUBLICATIONS

Jonsson et. al., 1993, "Quantitative sequence-activity models (QSAM)-tools for sequence design," Nucleic Acids Research 21, 733-739.

Lu et al., 2001, "Predicting the reactivity of proteins from their sequence alone. Kazal family of protein inhibitors of serine proteinases," PNAS 98, 1410-1415.

Ness et al., 2001, "Molecular Breeding: The Natural Approach to Protein Design," Advances in Protein Chemistry 55, 261-292.

Pierce et al., 2002, "Protein Design is *NP*-hard," Protein Engineering 15, 779-782.

Sandberg et al., 1993, "Engineering multiple properties of a protein by combinatorial mutagenesis," Proc. Natl. Acad. Sci. 90, 8367-8371.

Shaw et al., 2002, "Predicting Amino Acid Residues Responsible for Enzyme Specificity Solely from Protein Sequences," Biotechnology and Bioengineering 79, 295-300.

Wrede et al. 1998, "Peptide Design Aided by Neural Networks; Biological Activity of Artificial Signal Peptidase I Cleavage Sites," Biochemistry 37, 3588-3593.

Agrafiotis et al., 2002, "On the use of neural network ensembles in QSAR and QSPR," J Chem Inf Comput Sci, vol. 42, pp. 903-911.

Free et al., 1964, "A mathematical contribution to structure-activity studies," Journal of Medicinal Chemistry, American Chemical Society, vol. 7, No. 4, pp. 395-399.

Irini et al., 2002, "Additive method for the Prediction of Protein-Peptide Binding Affinity. Application to the MHC Class I Molecule HLA-A*0201," Journal of Proteome Research, vol. 1, No. 3, pp. 263-272.

Koshi et al., "Mutation Matrices and Physical-Chemical Properties: Correlations and Implications," 1997, *PROTEINS: Structure, Function and Genetics* vol. 27, pp. 336-344.

Norinder et al., 1997, "A Quantitative Structure-Activity Relationship Study of Some Substance P-related Peptides. A Multivariate Approach using PLS and Variable Selection," Journal of Peptide Research vol. 49, No. 2, pp. 155-162.

Svetnik et al., 2003, "Random Forest: A Classification and Regression Tool for Compound Classification and QSAR Modeling," J Chem Inf Comput Sci, vol. 43, No. 6, pp. 1947-1958.

Partial European Search Report dated Oct. 13, 2008 for EP 08003668.4.

Supplementary European Search Report dated Jan. 12, 2007 for European Application No. 04779720.4 (PCT/US2004024752).

Communication relating to Partial European Search Report dated Mar. 4, 2009 for EP 08003668.4.

Communication pursuant to Article 94(3) EPC dated Aug. 18, 2009 for EP 08003668.4.

U.S. Appl. No. 12/238,216, filed Sep. 25, 2008, Gustafsson et al.

International Search Report and Written Opinion dated Feb. 21, 2006 for International Application No. PCT/US04/024751.

Preliminary Amendment Under 37 C.F.R. § 1.115 dated Sep. 24, 2008 for U.S. Appl. No. 12/238,216.

```
┌─────────────────────────────────────────────────────────────┐
│ Selection of antibody with some initial binding (step 1)    │
└─────────────────────────────────────────────────────────────┘
                              │
                              ▼
┌─────────────────────────────────────────────────────────────┐
│ Initial design                                              │
│ a) Identify positions where substitution is acceptable and  │
│ choose substitution s to explore. (step 2)                  │
│ b) Design an initial small set of variants using experimental│
│ design methods. (step 3)                                    │
└─────────────────────────────────────────────────────────────┘
```

Initial design
a) Identify positions where substitution is acceptable and choose substitution s to explore. (step 2)
b) Design an initial small set of variants using experimental design methods. (step 3)

Optionally add new substitutions from step 02 for inclusion in the new variant set Synthesize and test antibody variant set for target binding and viral neutralizing activity. (step 4)

Propose a new variant set based on the model. (step 7)

Modify initial selection parameters based on performance (Step 09)

End-point reached

Iterate

Derive sequence –activity relationships (step 5)

Combine results from different sequence-function models. (step 6)

Select the best variant(s) (step 8). Use sequences and activities of these variants to modify algorithms used for substitution selection (step 9) and sequence-function modeling. (step 10)

Modify methods for combining different sequence-function models based on performance (Step 10)

Figure 3

| Select initial candidate antibody sequence(s) |

A: Substitutions from homologous sequences in framework & CDR
- Identify framework sequences within a defined evolutionary distance (PAM units)
- Reconstruct phylogenetic tree for framework region only RULE 1a:
- Select a defined number of framework residues that have undergone advantageous change RULE 2a:
- Select defined number of framework and defined number of CDR positions with highest mutability index RULE 3a:
- Select all amino acid substitutions from sequences in the same Chothia class SCORE:: Weighted value for each rule satisfied

B: Substitutions from homologous structures
- Superpose homologous structures from PDB RULE 1b:
- Estimate mean RMSD for every window of a defined number of residues
- Select framework sites with an RMSD greater than a defined value RULE 2b:
- Identify changes found in homologous sequences
- Select framework varying sites within a defined distance from CDR SCORE:: Weighted value for each rule satisfied

C: Substitutions from substitution matrices
- Calculate substitution matrix for all framework regions and canonical classes, rank all possible single substitutions for favorability RULE 1c:
- Select highest scoring substitutions for each matrix RULE 2c:
- Rank all possible single substitutions for favorability using a universal substitution matrix
- Select highest scoring positions SCORE: Weighted value for each rule satisfied

D: Substitutions from PCA analysis
- Determine principal components of sequence variation in alignment of homologs RULE 1d:
- Group CDRs based on PCA of amino acid sequences in the CDR.
- Select highest scoring CDR positions that differentiate antibody sequences by function RULE 2d:
- Group CDR positions based on observed amino acid frequencies at each site
- Rank the groups based on contributions to one or more principal components
- Select the top groups of sites to vary.

SCORE: Weighted value for each rule satisfied

E: Substitutions from Binding pocket Analysis

RULE 1e:
- Select sites based where physico-chemical properties of residues are conserved in the pocket RULE 2e:
- Select CDR changes derived from evolutionary models to correlate properties of amino acids.

SCORE: Weighted value for each rule satisfied

Figure 5

E coli leader peptide
-20          -10        -1
MKKLLFAIPL   VVPFYSHSTM    (SEQ ID NO.: 1)

Proteinase K
1            11           21           31           41
APAVEQRSEA   APLIEARGEM   VANKYIVKFK   EGSALSALDA   AMEKISGKPD 51           61           71           81           91
HVYKNVFSGF   AATLDENMVR   VLRAHPDVEY   IEQDAVVTIN   AAQTNAPWGL 101          111          121          131          141
ARISSTSPGT   STYYYDESAG   QGSCVYVIDT   GIEASHPEFE   GRAQMVKTYY 151          161          171          181          191
YSSRDGNGHG   THCAGTVGSR   TYGVAKKTQL   FGVKVLDDNG   SGQYSTIIAG 201          211          221          231          241
MDFVASDKNN   RNCPKGVVAS   LSLGGGYSSS   VNSAAARLQS   SGVMVAVAAG 251          261          271          281          291
NNNADARNYS   PASEPSVCTV   GASDRYDRRS   SFSNYGSVLD   IFGPGTSILS 301          311          321          331          341
TWIGGSTRSI   SGTSMATPHV   AGLAAYLMTL   GKTTAASACR   YIADTANKGD 351          361          371
LSNIPFGTVN   LLAYNNYQAV   DHHHHHH    (SEQ ID NO.: 2)

Figure 8

```
-60        -50        -40        -30        -20        -10        -1
atgaaaaaac tgctgttcgc gattccgctg gtggtgccgt tctatagcca tagcaccatg 1          11         21         31         41         51
GCACCGGCCG TTGAACAGCG TTCTGAAGCA GCTCCTCTGA TTGAGGCACG TGGTGAAATG 61         71         81         91         101        111
GTAGCAAACA AGTACATCGT GAAGTTCAAG GAGGGTTCTG CTCTGTCTGC TCTGGATGCT 121        131        141        151        161        171
GCTATGGAAA AGATCTCTGG CAAGCCTGAT CACGTCTATA AGAACGTGTT CAGCGGTTTC 181        191        201        211        221        231
GCAGCAACTC TGGACGAGAA CATGGTCCGT GTACTGCGTG CTCATCCAGA CGTTGAATAC 241        251        261        271        281        291
ATCGAACAGG ACGCTGTGGT TACTATCAAC GCGGCACAGA CTAACGCACC TTGGGGTCTG 301        311        321        331        341        351
GCACGTATTT CTTCTACTTC CCCGGGTACG TCTACTTACT ACTACGACGA GTCTGCCGGT 361        371        381        391        401        411
CAAGGTTCTT GCGTTTACGT GATCGATACG GGCATCGAGG CTTCTCATCC TGAGTTTGAA 421        431        441        451        461        471
GGCCGTGCAC AAATGGTGAA GACCTACTAC TACTCTTCCC GTGACGGTAA TGGTCACGGT 481        491        501        511        521        531
ACTCATTGCG CAGGTACTGT TGGTAGCCGT ACCTACGGTG TTGCTAAGAA AACGCAACTG 541        551        561        571        581        591
TTCGGCGTTA AAGTGCTGGA CGACAACGGT TCTGGTCAGT ACTCCACCAT TATCGCGGGT 601        611        621        631        641        651
ATGGATTTCG TAGCGAGCGA TAAAAACAAC CGCAACTGCC CGAAAGGTGT TGTGGCTTCT 661        671        681        691        701        711
CTGTCTCTGG GTGGTGGTTA CTCCTCTTCT GTTAACAGCG CAGCTGCACG TCTGCAATCT 721        731        741        751        761        771
TCCGGTGTCA TGGTCGCAGT AGCAGCTGGT AACAATAACG CTGATGCACG CAACTACTCT 781        791        801        811        821        831
CCTGCTAGCG AGCCTTCTGT TTGCACCGTG GGTGCATCTG ATCGTTATGA TCGTCGTAGC 841        851        861        871        881        891
TCCTTCAGCA ACTATGGTTC CGTCCTGGAT ATCTTCGGCC CTGGTACTTC TATCCTGTCT
```

Figure 9A

```
901        911        921        931        941        951
ACCTGGATTG GCGGTAGCAC TCGTTCCATT TCCGGTACGA GCATGGCTAC TCCACATGTT 961        971        981        991        1001       1011
GCTGGTCTGG CAGCATACCT GATGACCCTG GGTAAGACCA CTGCTGCATC CGCTTGTCGT 1021       1031       1041       1051       1061       1071
TACATCGCGG ATACTGCGAA CAAAGGCGAT CTGTCTAACA TCCCGTTCGG CACCGTTAAT 1081       1091       1101       1111       1121       1131
CTGCTGGCAT ACAACAACTA TCAGGCTgtc gaccatcatc atcatcatca tag
```

(SEQ ID NO.: 3)

Figure 9B gi|19171215|emb|CAD20578.1|/89
gi|19171217|emb|CAD20579.1|/1-
gi|19171219|emb|CAD20580.1|/1-
gi|19171221|emb|CAD20581.1|/1-
gi|16215662|emb|CAC95042.1|/90
gi|16506136|dbj|BAB70705.1|/78
gi|16506134|dbj|BAB70704.1|/78
gi|16506140|dbj|BAB70707.1|/78
gi|16215677|emb|CAC95049.1|/90
gi|117631|sp|P29138|CUDP_METAN
gi|6624958|emb|CAB63911.1|/90-
gi|16215669|emb|CAC95045.1|/90
gi|460032|gb|AAA91584.1|/84-36
gi|6634475|emb|CAB64346.1|/87-
gi|16215664|emb|CAC95043.1|/87
gi|2351388|gb|AAC49831.1|/86-3
gi|8671180|emb|CAB95012.1|/85-
gi|16215666|emb|CAC95044.1|/85
gi|16215671|emb|CAC95046.1|/85
gi|4092486|gb|AAC99421.1|/64-2
gi|18542429|gb|AAL75579.1|AF46
SUTIKA/91-367
gi|131077|sp|P06873|PRTK_TRIAL
gi|230675|pdb|2PRK|/1-277
gi|494434|pdb|1PEK|E/1-277
gi|224977|prf||1205229A/1-275
gi|14278658|pdb|1IC6|A/1-277
gi|131084|sp|P23653|PRTR_TRIAL
gi|4761119|gb|AAD29255.1|AF104
gi|14626933|gb|AAK70804.1|/81-
gi|639712|gb|AAC48979.1|/83-34
gi|742825|prf||2011184A/84-362
gi|628051|pir||JC2142/84-362
gi|15808791|gb|AAL08502.1|AF41
gi|15808805|gb|AAL08509.1|AF41
gi|28918475|gb|EAA28148.1|/90-
gi|10181226|gb|AAC27316.2|/92-
gi|131088|sp|P20015|PRTT_TRIAL
gi|9971109|emb|CAC07219.1|/86-
gi|7543916|emb|CAB87194.1|/89-
gi|5813790|gb|AAD52013.1|AF082
gi|23894244|emb|CAD23614.1|/11
gi|22652141|gb|AAN03634.1|AF40
gi|24528136|emb|CAD24010.1|/10
gi|24528132|emb|CAD24008.1|/10
A35742./126-403
gi|114081|sp|P08594|AQL1_THEAQ
AAA82980./129-408
gi|15640187|ref|NP_229814.1|/1
AAA22247./107-381

Figure 10

| Residue | PC1 contrib. | PC2 contrib. | PC1+2 contrib. |
|---|---|---|---|
| 15D | -0.0881 | -0.0803 | -0.1684 |
| 18D | -0.0881 | -0.0803 | -0.1684 |
| 19Q | -0.0881 | -0.0803 | -0.1684 |
| 22L | -0.0881 | -0.0803 | -0.1684 |
| 23P | -0.0881 | -0.0803 | -0.1684 |
| 65Y | -0.0881 | -0.0803 | -0.1684 |
| 66D | -0.0881 | -0.0803 | -0.1684 |
| 110R | -0.0881 | -0.0803 | -0.1684 |
| 137P | -0.0881 | -0.0803 | -0.1684 |
| 164D | -0.0881 | -0.0803 | -0.1684 |
| 189C | -0.0881 | -0.0803 | -0.1684 |
| 198R | -0.0881 | -0.0803 | -0.1684 |
| 8P | -0.0772 | -0.0777 | -0.1549 |
| 34T | -0.0772 | -0.0777 | -0.1549 |
| 67A | -0.0772 | -0.0777 | -0.1549 |
| 75Q | -0.0772 | -0.0777 | -0.1549 |
| 161T | -0.0772 | -0.0777 | -0.1549 |
| 199V | -0.0772 | -0.0777 | -0.1549 |
| 167V | -0.0899 | -0.0589 | -0.1488 |
| 21D | -0.0733 | -0.0657 | -0.1390 |
| 169N | -0.0613 | -0.0746 | -0.1359 |
| 134H | -0.0675 | -0.0664 | -0.1339 |

| Variation | Score | Primary contribution to score |
|---|---|---|
| N95C | 5 | Structural stability at higher temperature: from published literature |
| P97S | 3 | P to S for flexibility and structural perturbabtion |
| S107D | 5 | from active homologs |
| S123A | 7 | Thermostable consensus |
| E138A | 5 | From experiments in literature |
| M145F | 5 | From experiments to improve thermostability |
| Y151A | 8 | From experiments to improve thermostability |
| V167I | 10 | Allow user specified conservative changes (controlled perturbation) |
| L180I | 10 | Allow user specified conservative changes (controlled perturbation) |
| Y194S | 10 | Varaiation observed in highly active clone from our initial exp. |
| A199S | 8 | Allow user specified conservative changes (controlled perturbation) |
| K208H | 7 | PCA modelling of homologs collected from GenBank. |
| A236V | 7 | PCA modelling of homologs collected from GenBank. |
| R237N | 5 | From experiments to improve thermostability (in literature) |
| P265S | 3 | P to S for flexibility and structural perturbabtion |
| V267I | 10 | Allow user specified conservative changes (controlled perturbation) |
| S273T | 15 | Multiple sources identify this change. (thermostability and other) |
| G293A | 8 | For thermostability considerations (observed in thermitases) |
| L299C | 5 | For disulphide bridges with N95C ( from literature) |
| I310K | 5 | from structural studies |
| K332R | 8 | for thermostability considerations (observed in thermitases) |
| S337N | 8 | for thermostability considerations (observed in thermitases) |
| P355S | 3 | P to S for flexibility and structural perturbabtion |

Figure 15 variant-1: 123, 151, 293, 310, 332, 355
variant-2: 95, 145, 167, 199, 237, 273
variant-3: 97, 138, 180, 194, 236, 267
variant-4: 107, 132, 208, 265, 299, 337
variant-5: 123, 145, 151, 167, 273, 337
variant-6: 97, 107, 180, 236, 237, 310
variant-7: 123, 138, 199, 208, 265, 355
variant-8: 95, 194, 267, 293, 299, 332
variant-9: 95, 132, 138, 145, 167, 208
variant-10: 236, 237, 273, 293, 332, 355
variant-11: 97, 123, 265, 299, 310, 337
variant-12: 107, 151, 180, 194, 199, 267
variant-13: 95, 107, 123, 180, 194, 337
variant-14: 138, 151, 167, 199, 208, 299
variant-15: 97, 145, 237, 273, 293, 310
variant-16: 132, 236, 265, 267, 332, 355
variant-17: 97, 151, 199, 236, 299, 355
variant-18: 95, 107, 167, 180, 293, 310
variant-19: 145, 237, 265, 267, 332, 337
variant-20: 123, 132, 138, 194, 208, 273
variant-21: 123, 208, 236, 267, 293, 299
variant-22: 107, 132, 138, 145, 337, 355
variant-23: 97, 180, 194, 199, 265, 310
variant-24: 95, 151, 167, 237, 273, 332

Figure 16

| Variant # | Changes | Reasons |
| --- | --- | --- |
| variant-25 | 95 | Confirm detrimental effect on enzyme |
| variant-26 | 97 | Confirm detrimental effect on enzyme |
| variant-27 | 138 | Confirm detrimental effect on enzyme |
| variant-28 | 208 | Confirm detrimental effect on enzyme |
| variant-29 | 236 | Confirm detrimental effect on enzyme |
| variant-30 | 237 | Confirm detrimental effect on enzyme |
| variant-31 | 265 | Confirm detrimental effect on enzyme |
| variant-32 | 299 | Confirm detrimental effect on enzyme |
| variant-33 | 107, 123, 145 | New combinations of positive changes |
| variant-34 | 151, 167, 180 | New combinations of positive changes |
| variant-35 | 194, 199, 267 | New combinations of positive changes |
| variant-36 | 273, 293, 310 | New combinations of positive changes |
| variant-37 | 332, 337, 355 | New combinations of positive changes |
| variant-38 | 107, 151, 194, 273, 332 | New combinations of positive changes |
| variant-39 | 123, 167, 199, 293, 337 | New combinations of positive changes |
| variant-40 | 145, 180, 267, 310, 355 | New combinations of positive changes |
| variant-41 | 107, 167, 267, 273, 337 | New combinations of positive changes |
| variant-42 | 123, 180, 194, 293, 355 | New combinations of positive changes |
| variant-43 | 145, 151, 199, 310, 332 | New combinations of positive changes |
| variant-44 | 145, 167, 194 | New combinations of positive changes |
| variant-45 | 180, 199, 273 | New combinations of positive changes |
| variant-46 | 267, 293, 332 | New combinations of positive changes |
| variant-47 | 310, 337, 107 | New combinations of positive changes |
| variant-48 | 355, 123, 151 | New combinations of positive changes |

Figure 17

| Sequence changes | | | Variants | | | | | | | | | | | | | | | | | |
|---|---|---|---|---|---|---|---|---|---|---|---|---|---|---|---|---|---|---|---|---|
| Position | WT | Mut | 10 | 12 | 13 | 14 | 15 | 19 | 20 | 21 | 22 | 23 | 24 | 25 | 26 | 27 | 29 | 30 | 31 |
| 25 | Y | H | | | | | | | | | | | | H | | | | | |
| 34 | A | S | | | | | | | | | | | | | S | | | | |
| 48 | K | E | | | | | | | | | | | | | | | | | |
| 50 | D | N | | | | | | | N | | | | | | | | | | |
| 55 | N | S | | | | | | | | | | | | S | | | | | |
| 63 | T | S | | | | | | | | | | | | | | | | | |
| 88 | T | I | | | | | | | | | | | | | | | | | |
| 95 | N | C | | | | | | | | | | | | | | | | | |
| 97 | P | S | | | | | | | | | | | | | | | | | |
| 107 | S | D | | | | D | | | | | | | | | | | | D | D |
| 123 | S | A | | A | | | | | | | | | | | | | | | |
| 132 | I | V | | | V | | | | | | | | | | | | | | |
| 138 | E | A | | | | | | | | | | | | | | | | | |
| 145 | M | F | | | F | | | | | | | | | | | | | | |
| 151 | Y | A | | A | A | A | | | | | | A | A | A | | | | A | A |
| 167 | V | I | | | I | | | | | | | I | I | I | | | | | |
| 180 | L | I | | | | I | | | | | | I | I | I | | | | | |
| 194 | Y | S | S | | | S | | | | | | | | S | | | | S | S |
| 199 | A | S | | | | S | | | | | | | | S | | | | | |
| 208 | K | H | | | | | H | | | | | | | | | | | | |
| 209 | N | K | | | | | | | | | | | | | | | | | |
| 233 | S | N | | | | | | | | | | | | | | | | | |
| 236 | A | V | | | | | | | | | | | | | | | | | |
| 237 | R | N | | | | N | | N | N | | | | | | | | | | |
| 265 | P | S | | | | | | | | | S | | | | | | | | |
| 267 | V | I | | | | I | | | | | | | | | I | | | | |
| 273 | S | T | | | T | | T | | | | | | | | T | | | T | T |
| 293 | G | A | | A | | | A | | | | | | | | A | | | | |
| 299 | L | C | | | | | | | | | | | | | | | | | |
| 310 | I | K | | K | | | | | | | | | | | K | | | | |
| 332 | K | R | | R | | | R | | | | | | | | | | R | R | R |
| 337 | S | N | | | N | | | | | | | | | | N | | | | |
| 355 | P | S | | S | | | S | | | | | | | | S | | | | |
| 362 | L | M | | | | | | | M | | | | | | | | | | |
| 363 | A | V | | | | | | | | | | | V | | | | | | |
| 369 | A | V | | | | | | | | | | | | | | | | | |

Figure 18A

| Sequence changes | | | Variants | | | | | | | | | | | | | | | | |
|---|---|---|---|---|---|---|---|---|---|---|---|---|---|---|---|---|---|---|---|
| Position | WT | Mut | 32 | 33 | 35 | 36 | 37 | 38 | 39 | 40 | 41 | 42 | 43 | 45 | 46 | 47 | 48 | 49 | 50 |
| 25 | Y | H | | | | | | | | | | | | | | | | | |
| 34 | A | S | | | | | | | | | | | | | | | | | |
| 48 | K | E | | | | | | | | | | | | | | | | | |
| 50 | D | N | | | | | | | | | | | | | | | | | |
| 55 | N | S | | | | | | | | | | | | | | | | | |
| 63 | T | S | | | | | | | | | | | | | | | | | |
| 88 | T | I | | | | | | | | | | | | | | I | | | |
| 95 | N | C | | | | | | | | | | | | | | | | | |
| 97 | P | S | | | | | | | | | | | | | | | | | |
| 107 | S | D | | | D | | | | | | | D | | | | | | | |
| 123 | S | A | A | A | | A | A | | | | | | A | | | | | | |
| 132 | I | V | | | | | | | | | | | | | | | | | |
| 138 | E | A | | | | | | | | | | | | | | | | | |
| 145 | M | F | | | | | | F | | | | | | | | | | | |
| 151 | Y | A | | | | | | | | | | | A | | | A | A | A | A |
| 167 | V | I | I | I | I | | | I | | | | | | | | I | I | I | I |
| 180 | L | I | | | | I | I | | I | | | | | | | I | I | I | I |
| 194 | Y | S | | | | S | S | S | | | | | | | | | | | |
| 199 | A | S | S | S | | | | | S | | | | | | | | | | |
| 208 | K | H | | | | | | | | | | | | | | | | | |
| 209 | N | K | | | | | | | | | | | | | | | | | |
| 233 | S | N | | | | | | | | | | | | | | | | | |
| 236 | A | V | | | | | | | | | | | | | | | | | |
| 237 | R | N | | | | | | | | | | | | | N | N | | | |
| 265 | P | S | | | | | | | | | | | | | | | | | |
| 267 | V | I | | | | I | | | | | I | I | | | | | | | |
| 273 | S | T | | | | T | | | T | | | | | | | | | | |
| 293 | G | A | A | A | | A | A | | | | A | A | | | | | | | |
| 299 | L | C | | | | | | | | | | | | | | | | | |
| 310 | I | K | | | | | | | | | | | | | K | | | | |
| 332 | K | R | | | | | | | | | R | R | | | | | | | |
| 337 | S | N | N | N | N | | | | | | | | | N | | | | | |
| 355 | P | S | | | | S | S | | | | | | | S | | | | | |
| 362 | L | M | | | | | | | | | | | | | | | | | |
| 363 | A | V | | | | | | V | | | | | | | | | | | |
| 369 | A | V | | | | | | | | | | | | | V | | | | |

Figure 18B

| Sequence changes | | | Variants | | | | | | | | | | | |
|---|---|---|---|---|---|---|---|---|---|---|---|---|---|---|
| Position | WT | Mut | N2 | N3 | N4 | N6 | N7 | N8 | N9 | N10 | N11 | N13 | N14 | N15 |
| 25 | Y | H | | | | | | | | | | | | |
| 34 | A | S | | | | | | | | | | | | |
| 48 | K | E | | | | | | | | | | | | |
| 50 | D | N | | | | | | | | | | | | |
| 55 | N | S | | | | | | | | | | | | |
| 63 | T | S | | | | | | | | | | | | |
| 88 | T | I | | | | | | | | | | | | |
| 95 | N | C | C | | | | | C | C | | | C | | |
| 97 | P | S | | S | | S | | | | | S | | | S |
| 107 | S | D | | | D | D | | | | | | D | | |
| 123 | S | A | | | | A | | | | | A | A | | |
| 132 | I | V | | | V | | | | V | | | | | |
| 138 | E | A | | A | | | A | | A | | | | A | |
| 145 | M | F | F | | | | | | F | | | | | F |
| 151 | Y | A | | | | | | | | | | | A | |
| 167 | V | I | I | | | | | | I | | | | I | |
| 180 | L | I | | I | | I | | | | | | I | | |
| 194 | Y | S | | S | | | | S | | | | S | | |
| 199 | A | S | S | | | | S | | | | | | S | |
| 208 | K | H | | | H | | H | | H | | | | H | |
| 209 | N | K | | | | | | | | | | | | |
| 233 | S | N | | | | | | | | | | | | |
| 236 | A | V | | V | | V | | | V | | | | | |
| 237 | R | N | N | | | N | | | N | | | | | N |
| 265 | P | S | | | S | S | | | | | S | | | |
| 267 | V | I | | I | | | I | | | | | | | |
| 273 | S | T | T | | | | | | T | | | | | T |
| 293 | G | A | | | | | | A | A | | | | | A |
| 299 | L | C | | | C | | C | | | C | | C | | |
| 310 | I | K | | | K | | | | | K | | | | K |
| 332 | K | R | | | | | | R | R | | | | | |
| 337 | S | N | | | N | | | | | N | N | | | |
| 355 | P | S | | | | | S | | S | | | | | |
| 362 | L | M | | | | | | | | | | | | |
| 363 | A | V | | | | | | | | | | | | |
| 369 | A | V | | | | | | | | | | | | |

Figure 18C

| Sequence changes | | | Variants | | | | | | | | | | | | | | | |
|---|---|---|---|---|---|---|---|---|---|---|---|---|---|---|---|---|---|---|
| Position | WT | Mut | N16 | N17 | N18 | N19 | N20 | N21 | N22 | N23 | N24 | N25 | N26 | N27 | N28 | N30 | N33 | N40 | N43 |
| 25 | Y | H | | | | | | | | | | | | | | | | | |
| 34 | A | S | | | | | | | | | | | | | | | | | |
| 48 | K | E | | | | | | | | | | | | | | | | | |
| 50 | D | N | | | | | | | | | | | | | | | | | |
| 55 | N | S | | | | | | | | | | | | | | | | | |
| 63 | T | S | | | | | | | | | | | | | | | | | |
| 88 | T | I | | | | | | | | | | | | | | | | | |
| 95 | N | C | | | C | | | | | | C | C | | | | | | | |
| 97 | P | S | | S | | | | | | S | | | S | S | | | | | |
| 107 | S | D | | | D | | | | D | | | | | | | | D | | |
| 123 | S | A | | | | | A | A | | | | | | | | | A | | |
| 132 | I | V | V | | | | V | | V | | | | | | | | | | |
| 138 | E | A | | | | | A | | A | | | | | | A | | | | |
| 145 | M | F | | | | F | | | F | | | | | | | | F | F | F |
| 151 | Y | A | | A | | | | | | | A | | | | | | | | A |
| 167 | V | I | | | I | | | | | | I | | | | | | | | |
| 180 | L | I | | | I | | | | | I | | | | | | | | I | |
| 194 | Y | S | | | | | S | | | S | | | | S | | | | | |
| 199 | A | S | | S | | | | | | S | | | | | | | | | S |
| 208 | K | H | | | | H | H | | | | | | | | | | | | |
| 209 | N | K | | | | | | | | | | | | | | | | | |
| 233 | S | N | | | | | | | | | | | | | | | | | |
| 236 | A | V | V | V | | | | V | | | | | | | | V | | | |
| 237 | R | N | | | | N | | | | | N | | | | | | | | |
| 265 | P | S | S | | | S | | | | S | | | | | | | | | |
| 267 | V | I | I | | | I | | I | | | | | | | | | | I | |
| 273 | S | T | | | | | T | | | | T | | | | | | | | |
| 293 | G | A | | A | | | | A | | | | | | | | | | | |
| 299 | L | C | | C | | | | C | | | | | C | C | | | | | |
| 310 | I | K | | | K | | | | | K | | | | | | | | K | K |
| 332 | K | R | R | | | R | | | | | R | | | | | | | | R |
| 337 | S | N | | | | N | | | N | | | | | | | | | | |
| 355 | P | S | S | S | | | | | | S | | | | | | | | S | |
| 362 | L | M | | | | | | | | | | | | | | | | | |
| 363 | A | V | | | | | | | | | | | | | | | | | |
| 369 | A | V | | | | | | | | | | | | | | | | | |

Figure 18D

| Sequence changes | | | Variants | | | | | | | | | | | | | | | |
|---|---|---|---|---|---|---|---|---|---|---|---|---|---|---|---|---|---|---|
| Position | WT | Mut | 47 | 48 | 49 | 50 | 51 | 52 | 53 | 54 | 55 | 56 | 57 | 58 | 59 | 60 | 61 | 62 | 63 |
| 25 | Y | H | | | | | | | | | | | | | | | | | |
| 34 | A | S | | | | | | | | | | | | | | | | | |
| 48 | K | E | | | | | | | | | | | | | | | | | |
| 50 | D | N | | | | | | | | | | | | | | | | | |
| 55 | N | S | | | | | | | | | | | | | | | | | |
| 63 | T | S | | | | | | | | | | | | | | | | | |
| 88 | T | I | I | | | | | | | | | | | | | | | | |
| 95 | N | C | | | | | | | | | | | | | | | | | |
| 97 | P | S | | | | | | | | | | | | | | | | | |
| 107 | S | D | | | | | | | | | | | | | | | | | |
| 123 | S | A | | | | | | | | | | | | | | | | | |
| 132 | I | V | | | | | | | | | | | | | | | | | |
| 138 | E | A | | | | | | | | | | | | | | | | | |
| 145 | M | F | | | | | | | | | | | | | | | | | |
| 151 | Y | A | A | A | A | A | | | | | | | | | | | | | |
| 167 | V | I | I | I | I | I | | | | | | | I | I | | | I | I | I |
| 180 | L | I | I | I | I | I | | | | | | | | | | | | | |
| 194 | Y | S | | | | | S | S | S | S | | | | | | | | | |
| 199 | A | S | | | | | S | S | S | S | | | | | | | | | |
| 208 | K | H | | | | | | | | | H | H | | | | | | | |
| 209 | N | K | | | | | | | | | K | | | | | | | | |
| 233 | S | N | | | | | | | | | | | N | | | | | | |
| 236 | A | V | | | | | | | | | | | | | | | | | |
| 237 | R | N | | | | | | | | | | | | | N | N | N | N | N |
| 265 | P | S | | | | | | | | | | | | | | | | | |
| 267 | V | I | | | | | I | I | I | I | I | I | I | I | I | I | | | I |
| 273 | S | T | | | | | | | | | | | | | | | | | |
| 293 | G | A | | | | | | | | | A | A | A | A | A | A | A | A | A |
| 299 | L | C | | | | | | | | | | | | | | | | | |
| 310 | I | K | | | | | | | | | | | | | | | | | |
| 332 | K | R | | | | | | | | | R | R | R | R | R | R | R | R | R |
| 337 | S | N | | | | | | | | | | | N | N | | | | | N |
| 355 | P | S | | | | | | | | | | | | | S | S | S | S | S |
| 362 | L | M | | | | | | | | | | | | | | | | | |
| 363 | A | V | | | | | | | | | | | | | | | | | |
| 369 | A | V | | | | | | | | | | | | | | | | | |

Figure 18E

| Sequence changes | | | Variants | | | | | | | | |
|---|---|---|---|---|---|---|---|---|---|---|---|
| Position | WT | Mut | 65 | 66 | 67 | 69 | 70 | 71 | 72 | 73 | 74 |
| 25 | Y | H | | | | | | | | | |
| 34 | A | S | | | | | | | | | |
| 48 | K | E | | | | | | E | | | |
| 50 | D | N | | | | | | | | | |
| 55 | N | S | | | | | | | | | |
| 63 | T | S | | | | | | | S | | |
| 88 | T | I | | | | | | | | | |
| 95 | N | C | | | | | | | | | |
| 97 | P | S | | | | | | | | | |
| 107 | S | D | | | | | | | | | |
| 123 | S | A | | | | | | | | | |
| 132 | I | V | | | | | | | | | |
| 138 | E | A | | | | | | | | | |
| 145 | M | F | | | | | | | | | |
| 151 | Y | A | | | | | | | | | |
| 167 | V | I | I | I | | I | I | I | I | | |
| 180 | L | I | | | | | | | | | |
| 194 | Y | S | | | | | | | | | |
| 199 | A | S | | | | | | | | | |
| 208 | K | H | | | | | | H | H | H | H |
| 209 | N | K | | | | | | | | | |
| 233 | S | N | | | | | | | | | |
| 236 | A | V | | | | | | | | | |
| 237 | R | N | | | | | | N | N | | |
| 265 | P | S | | | | | | | | | |
| 267 | V | I | I | I | I | I | I | I | I | I | I |
| 273 | S | T | | | | T | T | | | | |
| 293 | G | A | A | A | | | | A | A | A | A |
| 299 | L | C | | | | | | | | | |
| 310 | I | K | | | | | | | | | |
| 332 | K | R | R | R | R | R | R | R | R | R | R |
| 337 | S | N | | | N | N | N | N | N | | |
| 355 | P | S | | | S | | | S | S | | |
| 362 | L | M | | | | | | | | | |
| 363 | A | V | | | | | | | | | |
| 369 | A | V | | | | | | | | V | V |

Figure 18F

| Variant | y1 | y2 | y4 | y5 | y6 | y7 |
|---|---|---|---|---|---|---|
| wt | 0.7526 | 0.8774 | 0.7477 | 1.1850 | 0.6604 | 2 |
| wt | 1.2316 | 1.0877 | 1.2523 | 0.8150 | 1.3396 | 2 |
| wt | 1.0822 | 0.9082 | 1.0894 | 1.0850 | 0.9829 | 2 |
| wt | 0.8904 | 1.1423 | 0.9106 | 0.9158 | 1.0171 | 2 |
| 10 | 0.0263 | 1.7208 | 0.1682 | -0.0125 | 0.0453 | 6 |
| 12 | 0.2211 | 0.1878 | 0.4486 | 0.2320 | 0.0415 | 2 |
| 13 | 0.0158 | 1.9119 | 0.2430 | -0.0376 | 0.0302 | 1 |
| 14 | 0.0158 | 2.3899 | 0.3364 | 0.0251 | 0.0377 | 6 |
| 15 | 1.6789 | 0.0135 | 2.3738 | 1.6176 | 0.0226 |  |
| 15 | 1.3945 | 0.4917 | 1.6260 | 1.2690 | 0.6857 |  |
| 19 | 0.9000 | 0.9476 | 1.0280 | 1.0219 | 0.8528 | 1 |
| 19 | 0.6932 | 1.0442 | 0.6667 | 0.8143 | 0.7238 | 1 |
| 20 | 1.2737 | 0.0593 | 1.5327 | 1.5172 | 0.0755 | 0 |
| 20 | 0.5507 | 0.0484 | 0.5203 | 0.6472 | 0.0267 | 0 |
| 21 | 0.1632 | 0.9251 | 0.0935 | 0.1881 | 0.1509 | 0 |
| 22 | 0.1947 | 0.3294 | 0.1869 | 0.2884 | 0.0642 | 2 |
| 23 | 1.8053 | 0.0878 | 3.0280 | 2.0000 | 0.1585 | 3 |
| 23 | 1.6932 | 0.0900 | 2.0163 | 1.6709 | 0.1524 | 3 |
| 24 | 0.0579 | 0.9777 | 0.0374 | 0.0627 | 0.0566 | 4 |
| 25 | 0.3421 | 1.4891 | 0.6168 | 0.4514 | 0.5094 | 6 |
| 26 | 0.0053 | 10.7547 | 0.2056 | 0.0094 | 0.0566 | 2 |
| 26 | 0.0521 | 0.4391 | 0.0650 | 0.0127 | 0.0229 | 2 |
| 27 | 0.3474 | 1.3905 | 0.3178 | 0.3793 | 0.4830 | 1 |
| 29 | 1.4263 | 0.0079 | 1.6822 | 1.6144 | 0.0113 | 4 |
| 29 | 1.2740 | 0.0150 | 1.7398 | 1.3431 | 0.0190 | 4 |
| 30 | 0.0316 | 0.9560 | 0.0935 | -0.0251 | 0.0302 | 8 |
| 31 | 0.0421 | 1.2547 | 0.1121 | 0.0502 | 0.0528 | 6 |
| 32 | 0.7316 | 1.2792 | 0.6916 | 1.0063 | 0.9358 | 4 |
| 33 | 0.3263 | 1.3530 | 0.5794 | 0.5235 | 0.4415 | 4 |
| 35 | 1.0737 | 0.1546 | 1.7009 | 1.4451 | 0.1660 | 1 |
| 36 | 0.0421 | 0.9858 | 0.2617 | 0.0752 | 0.0415 | 2 |
| 37 | 0.0316 | 0.9560 | 0.0187 | -0.0094 | 0.0302 | 2 |
| 38 | 0.0053 | 9.3208 | -0.0748 | -0.0157 | 0.0491 | 0 |
| 39 | 0.2158 | 1.2416 | 0.2430 | 0.3730 | 0.2679 | 1 |
| 40 | 1.6737 | 1.5444 | 2.5794 | 2.0031 | 2.5849 | 2 |
| 40 | 0.9342 | 1.4557 | 0.9593 | 0.9666 | 1.3600 | 2 |
| 41 | 0.9421 | 1.8906 | 1.1402 | 1.2539 | 1.7811 | 2 |
| 42 | 0.0474 | 1.3543 | 0.0935 | 0.0784 | 0.0642 | 0 |
| 43 | 0.4105 | 0.1287 | 0.5794 | 0.6364 | 0.0528 | 4 |
| 43 | 1.0466 | 0.0109 | 0.9919 | 0.6113 | 0.0114 | 4 |
| 46 | 0.4466 | 1.0919 | 0.3089 | 0.5245 | 0.4876 | 0.5 |
| 47 | 0.6575 | 0.7763 | 0.6016 | 0.8143 | 0.5105 | 7 |
| 48 | 0.9370 | 0.8253 | 0.9919 | 1.1168 | 0.7733 | 4 |
| 51 | 0.0219 | 1.5643 | -0.0488 | 0.0127 | 0.0343 | 1 |
| 55 | 1.0329 | 1.4901 | 1.0569 | 1.2986 | 1.5390 | 5 |

Figure 19A

| Variant | y1 | y2 | y4 | y5 | y6 | y7 |
|---|---|---|---|---|---|---|
| 56 | 1.3178 | 1.3124 | 1.5447 | 1.3198 | 1.7295 | 2 |
| 57 | 1.3123 | 0.9957 | 1.3496 | 1.2986 | 1.3067 | 3 |
| 58 | 0.9699 | 0.4635 | 0.8943 | 1.0237 | 0.4495 | 2 |
| 59 | 0.5260 | 0.0435 | 0.2927 | 0.5753 | 0.0229 | 0.5 |
| 60 | 0.5863 | 0.0325 | 0.3740 | 0.6578 | 0.0190 | 0.5 |
| 61 | 0.8548 | 0.0089 | 0.9268 | 0.9137 | 0.0076 | 0.5 |
| 62 | 0.3041 | 0.0752 | 0.2276 | 0.3574 | 0.0229 | 0.5 |
| 63 | 0.9370 | 0.0447 | 0.9919 | 0.9941 | 0.0419 | 0.5 |
| 65 | 0.3699 | 0.3193 | 0.0976 | 0.3955 | 0.1181 | 2 |
| 66 | 0.9096 | 0.5445 | 0.7480 | 0.9835 | 0.4952 | 2 |
| 67 | 0.2932 | 0.0520 | 0.1626 | 0.3194 | 0.0152 | 2 |
| 69 | 0.2301 | 0.2980 | 0.1951 | 0.1713 | 0.0686 | 2 |
| 70 | 0.5342 | 0.3066 | 0.2927 | 0.6028 | 0.1638 | 3 |
| 71 | 0.2411 | 0.3002 | 0.2114 | 0.2686 | 0.0724 | 0.5 |
| 72 | 0.4466 | 0.0427 | 0.2276 | 0.4611 | 0.0190 | 1 |
| 73 | 0.2219 | 0.7725 | 0.1138 | 0.2390 | 0.1714 | 4 |
| 74 | 0.7233 | 1.1113 | 0.4715 | 0.8164 | 0.8038 | 4 |

| Variation position | Casein hydrolysis (y7) | Thermal tolerance (y6) | AAPL-p-NA pH7.0 (y1) |
|---|---|---|---|
| 107 | D | S | S |
| 123 | A | S | S |
| 151 | A | Y | A |
| 167 | I | V | V |
| 180 | I | L | I |
| 194 | S | Y | Y |
| 199 | S | A | A |
| 208 | K | H | K |
| 267 | V | I | V |
| 273 | T | S | S |
| 293 | G | A | A |
| 332 | R | R | R |

| Gene # | Pos 7 | Pos 15 | Pos 18 | Pos 28 | Pos 32 | Pos 40 | Pos 53 |
|---|---|---|---|---|---|---|---|
| 1 | Q | K | E | N | I | S | E |
| 2 | Q | K | E | H | L | Q | D |
| 3 | Q | E | K | N | I | Q | D |
| 4 | Q | E | K | H | L | S | E |
| 5 | N | K | K | N | L | S | D |
| 6 | N | K | K | H | I | Q | E |
| 7 | N | E | E | N | L | Q | E |
| 8 | N | E | E | H | I | S | D |

Figure 25

Identify all sequences homologous to MX PEP and align using ClustalW

A: Substitutions set
RULE 1a:
- Identify all substitutions seen in 35 homologs from Genbamk
- Consider only these susbtitutions (ie RULE 1a is a filter)

B: Substitutions from homologous sequences
- Reconstruct phylogenetic tree

RULE 1b:
- Calculate evolutionary proximity of the closest homolog in which each substitution occurs (EP)

RULE 2b:
- Calculate site heterogeneity at each substitution position (SH)

RULE 3b:
- Calculate entropy at each substitution position (SE)

RULE 4b:
- Calculate number of times a substitution is seen at a position in the set of homologs (SN)

C: Substitutions from substitution matrices
RULE 1c:
- Calculate favorability of each substitution using a PAM250 matrix (SM).

D: Score
Score = f(EP) x f(SH) x f(SE) x f(SN) x f(SM)

Figure 26

Align RSV-19 heavy chain sequence with human germline ig heavy chain sequences from VBase using ClustalW.

A: Substitutions set
RULE 1a:
- Enumerate and classify the substitutions into 2 categories.
- (i) Substitutions found in the framework region (FW) and
- (ii) substitutions found in the complementarity determining region (CDR).
- Consider only these susbtitutions (ie RULE 1a is a filter), and consider them separately

B: Substitutions from human germline sequences
- Reconstruct phylogenetic tree RULE 1b:
- Calculate evolutionary proximity of the closest homolog in which each substitution occurs (EP)

RULE 2b:
- Calculate site heterogeneity at each substitution position (SH)

RULE 3b:
- Calculate entropy at each substitution position (SE)

RULE 4b:
- Calculate number of times a substitution is seen at a position in the set of homologs (SN)

C: Substitutions from substitution matrices
RULE 1c:
- Calculate favorability of each substitution using a PAM100 matrix (SM).

D: Score

$Score_{FW} = f(EP) \times f(SH) \times f(SE) \times f(SN) \times f(SM)$ $Score_{CDR} = f'(SE) \times f'(SN) \times f'(SM)$

Figure 28

SYSTEMS AND METHODS FOR BIOPOLYMER ENGINEERING

CROSS-REFERENCE TO RELATED APPLICATIONS

This application claims benefit, under 35 U.S.C. §119(e), of U.S. Provisional Patent Application No. 60/491,815 filed on Aug. 1, 2003 which is incorporated herein, by reference, in its entirety. This application also claims benefit, under 35 U.S.C. §119(e), of U.S. Provisional Patent Application No. 60/536,357 filed on Jan. 14, 2004 which is incorporated herein, by reference, in its entirety. This application also claims benefit, under 35 U.S.C. §119(e), of U.S. Provisional Patent Application No. 60/536,862 filed on Jan. 15, 2004 which is incorporated herein, by reference, in its entirety.

1. FIELD OF THE INVENTION

The field of this invention relates to computer systems and methods for designing sets of biopolymer variants and tools for relating the functional properties of such biopolymers to their sequences. These relationships can then be used to determine the relationship between a biopolymer's sequence and commercially relevant properties of that biopolymer. Such sequence-activity relationships may be used to design and synthesize commercially useful biopolymer compositions.

2. BACKGROUND OF THE INVENTION

Because of the immense size of sequence space, there is no effective way to systematically screen all possible permutations of a polymeric biological molecule such as a nucleic acid or protein for a desired property. To test each possible amino acid at each position in a protein, or each possible nucleotide base at each position in a gene, rapidly leads to such a large number of molecules to be tested such that no available methods of synthesis or testing are feasible, even for a polymer of modest length. Furthermore, most molecules generated in such a way would lack any measurable level of the desired property. Total sequence space is very large and the functional solutions in this space are sparsely distributed.

Two primary approaches have to date been used to identify polymeric biological molecules with desired properties: mechanistic and empirical. There are significant limitations to both of these approaches. The mechanistic approach is often hampered by insufficient knowledge of the system to be improved, meaning either that considerable resources must be devoted to characterizing the system (for example by obtaining high quality protein crystal structures and relating these to the properties of interest), or that meaningful predictions cannot be made. In contrast, the empirical approach requires no mechanistic understanding, but relies upon direct measurements of a biopolymer's properties to select those variants that are improved. This strength is also its weakness; large numbers of variants cannot typically be tested under conditions that are identical to those of the final application. High throughput screens are widely used to provide surrogate measurements of the properties of interest, but these are often inadequate: binding of a protein to a receptor in a phage display assay may have little bearing on its ultimate usefulness as a therapeutic protein, the activity of an enzyme in a microtitre plate may be unrelated to its activity in a biocatalytic reactor.

Empirical engineering of nucleic acids, proteins and other biopolymers relies upon creating and testing sets of variants, then using this information to design and synthesize subsequent sets of variants that are enriched for components that contribute to the desired activity. A key limitation for any empirical biopolymer engineering is in developing a good assay for biopolymer function. The assay must measure biopolymer properties that are relevant to the final application, but must also be capable of testing a sufficient number of variants to identify what may be only a small fraction that are actually improved. The difficulty of creating such an assay is particularly relevant when optimizing biopolymers for complex functions that are difficult to measure in high throughput. Examples include proteins or nucleic acids for therapeutic purposes and catalysts for the synthesis or degradation of polymers or chiral molecules.

Large numbers of variants cannot typically be tested under conditions that are identical to those of the final application. High throughput screens are widely used to provide surrogate measurements of the properties of interest, but these are often inadequate. As examples, binding of a protein to a receptor in a phage display assay can have little bearing on its ultimate usefulness as a therapeutic protein and the activity of an enzyme in a microtitre plate can be unrelated to its activity in a biocatalytic reactor.

Limitations in current methods for searching through biopolymer sequences for specific commercially relevant functionalities creates a need in the art for methods that can design and synthesize small numbers of variants for functional testing and that can use the resulting sequence and functional information to design and synthesize small numbers of variants improved for a desired commercially useful activity. Limitations in current methods for choosing surrogate screens appropriate for empirical biopolymer engineering creates a need in the art for methods that can design and create small numbers of variants that can then be tested for specific commercially relevant functionalities.

3. SUMMARY OF THE INVENTION

The systems and methods described here apply novel computational biology and data mining techniques to important molecular design problems. In particular, novel ways to map biopolymer sequence space are described. Such maps are used to direct perturbations or modifications of the biopolymer sequences in order to perturb or modify the activity of the biopolymers in a controlled fashion.

Methods are disclosed for biological engineering using the design and synthesis of a set of sequences containing designed substitutions that are statistically representative of a sequence space, and that contain a high fraction of polymeric biological molecules possessing desired properties. In addition to its functionality, each biopolymer is also designed to maximize the information that the set of biopolymers contains regarding the contribution of substitutions to the desired biopolymer properties and to the contributions resulting from interactions between substitutions. This in essence is a map of the sequence space that can also be used to design perturbations to modify the functionality of the biopolymer as desired.

The information used to create the substitutions that define the sequence space can be derived from one or more of (i) multiple sequence alignments, (ii) phylogenetic reconstructions of ancestral sequences, (iii) analysis of families or superfamilies of biopolymers related by sequence, function or partial function, (iv) analysis of monomer substitution probabilities within classes of biopolymer, (v) three dimensional structures (e.g., molecular models, X-ray crystallographic structures, nuclear magnetic resonance models, molecular dynamic simulations), (vi) immunogenic constraints, (vii) prior knowledge about the structure and/or function of the sequences upon which design of the biopolymer set is to be based, or (viii) any similar information pertaining to a related or homologous biopolymer. In one embodiment of the invention, this process is automated by use of an expert system that acquires domain knowledge and captures it as a knowledge database. This process can provide a score or rank order of substitutions to be incorporated, and a reasoning based on user specified constraints and domain specific data.

Generally speaking, the first step in the design and manufacture of the statistically representative sequence sets of this invention is the definition of the initial sequence space to be searched. This involves defining one or more reference sequences, identifying positions that are likely to tolerate alteration, and identifying substitutions at these positions that are likely to be acceptable or to produce desired changes in the properties of the biopolymer. All possible combinatorial strings of polymeric biological molecules define the total defined sequence space to be searched. Each substitution at each position is typically enumerated in silico and the acceptability defined computationally. Desirability or acceptability of each possible substitution is calculated according to one or more criteria. Such calculations can be performed by a computational system using the knowledge database, user specified constraints, and/or domain and biopolymer specific data.

The present invention also provides a more formal systematic method for selecting substitution positions. The use of a formal system involves quantitative scores and/or filters for assessing the favorability of substitution positions and the substitutions possible at those positions. Formalizing the system for substitution selection allows for the development of an automated system for biopolymer optimization. The parameters, filters and scores can be adjusted based on data from the scientific literature and data from experiments designed or interpreted by the automated system. By adjusting the scores and filters, substitutions that are predicted to be favorable can be aligned with those found experimentally to be favorable. Continuous refinement of these scores and filters based on experimental or computational data provides a way for the biopolymer optimization system to learn and improve. This formalization and learning capability are an aspect of the invention.

The second step in the design and manufacture of the statistically representative sequence sets of this invention is to define a subspace of the total sequence space to be searched in each iteration of the synthesis testing and correlating process. Typically the total allowed space matrix contains $10^5$-$10^{50}$ biopolymers, many orders of magnitude larger than can be synthesized and measured under commercially relevant conditions. Such commercially relevant conditions are presently limited to numbers in the range of $10^1$-$10^3$. The number of biopolymer variants that can be synthesized and tested under appropriate conditions is defined by the availability of resources. The number of variant positions and the number of substitutions that can be tested at each of those positions is then calculated, such that each substitution will be present in a statistically representative fraction of the set of biopolymers to be synthesized. Additionally, when using search methods like Tabu, Ant optimization or similar techniques, the space can be searched on a sequence by sequence basis by using a memory of the space that has been visited previously and the properties encountered.

Typical experimental design methods can introduce more changes in a biopolymer than the biopolymer can tolerate to remain functional. Adaptations of these methods, for example by using covering algorithms to reduce the total number of substitutions in each biopolymer variant, while maximizing the number of different combinations of pairs of substitutions is another aspect of the invention.

The third step in the design and manufacture of the statistically representative sequence sets (or sequence sets relevant for specific optimization techniques) of this invention is to create a set of variant biopolymers. This can be performed by synthesizing the biopolymer sequences defined and designed in the first two steps. The systematic design of such variants is one aspect of the present invention. The biopolymers can be synthesized individually, or in a multiplexed set that is subsequently deconvoluted by sequencing or some other appropriate method. Alternatively, the biopolymers can be created as a library of variants. Many methods have been described in the art for creating such libraries. See, for example, Stemmer, 1994, Proc Natl Acad Sci USA 91: 10747-51; Stemmer, 1994, Nature 370: 389-91; Crameri et al., 1996, Nat Med 2: 100-2; Crameri et al., 1998, Nature 391: 288-291; Ness et al., 1999, Nat Biotechnol 17: 893-896; Volkov et al., 1999, Nucleic Acids Res 27: e18.; Volkov et al., 2000, Methods Enzymol 328: 447-56.; Volkov et al., 2000, Methods Enzymol 328: 456-63.; Coco et al., 2001, Nat Biotechnol 19: 354-9.; Gibbs et al., 2001, Gene 271: 13-20.; Ninkovic et al., 2001, Biotechniques 30: 530-4, 536.; Coco et al., 2002, Nat Biotechnol 20: 1246-50.; Ness et al., 2002, Nat Biotechnol 20: 1251-5.; Aguinaldo et al., 2003, Methods Mol Biol 231: 105-10.; Coco, 2003, Methods Mol Biol 231: 111-27.; and Sun et al., 2003, Biotechniques 34: 278-80, 282, 284 passim. Alternatively, specifically designed biopolymers can be synthesized individually. See, for example, Norinder et al., 1997, J Pept Res 49: 155-62.; Bucht et al., 1999, Biochim Biophys Acta 1431: 471-82.

After synthesis, the designed set(s) of biopolymers are characterized functionally to measure the properties of interest. This requires the development of an assay or surrogate assay faithful to the property or properties of ultimate interest and to test some members of the set of variants for more than one property, including the property of ultimate interest. Data mining techniques are then employed to characterize the functions of the variants and to derive a relationship between biopolymer sequences and properties. Optionally, the characterization data can be used to provide information in a subsequent iteration of the method, aiding in the design of a subsequent set of statistically representative variants that can be synthesized and tested to obtain a molecule with even more desirable properties. The data from additional iterations of this process can also be used to refine the data mining algorithms and models produced from the first set of data. The knowledge created about the sequence space can in turn be incorporated into the knowledge database for evaluating the substitutions in the light of this data and recalculating the scores or rank order of the substitutions. These processes are aspects of the present invention.

Additionally, combinations of the methods described herein can be made with other techniques such as directed evolution, DNA shuffling, family shuffling and/or systematic scanning approaches. These can be performed in any order and for any number of iterations to produce the products described herein. All such combinations are within the scope of the invention.

An embodiment of the present invention provides a method for constructing a variant set for a biopolymer of interest. In the method, a plurality of positions in the biopolymer of interest is identified, using a plurality of rules. For each respective position in the plurality of positions, one or more substitutions for the respective position are identified. The plurality of positions and the one or more substitutions for each respective position in the plurality of positions collectively define a biopolymer sequence space. A variant set is selected from the biopolymer sequence space. That is, the variant set comprises a plurality of variants of the biopolymer of interest such that the variant set is a subset of the biopolymer sequence space. A property is measured for all or a portion of the variants in the variant set. A sequence-activity relationship is modeled between (i) one or more substitutions at one or more positions of the biopolymer of interest represented by the variant set and (ii) the property measured for all or the portion of the variants in the variant set. The variant set is then redefined to comprise variants that include substitutions in the plurality of positions that are selected based on a function of the sequence-activity relationship.

In some embodiments, the method further comprises repeating the measuring, modeling, and, optionally, the redefining, until a variant in the variant set exhibits a value for the property that exceeds a predetermined value. In some embodiments, this predetermined value is a value that is greater than the value for the property that is exhibited by the biopolymer of interest.

In some embodiments, the method further comprises repeating the measuring, modeling, and, optionally, the redefining, until a variant in the variant set exhibits a value for the property that is less than a predetermined value. In some embodiments, this predetermined value is a value that is less than the value for the property that is exhibited by the biopolymer of interest.

In some embodiments, the method further comprises repeating the measuring, modeling, and, optionally, the redefining, a predetermined number of times (e.g., two, three, four, or five times).

In some embodiments, the sequence-activity relationship comprises a plurality of values and each value in the plurality of values describes a relationship between (i) a substitution at a position in the plurality of positions represented by all or the portion of the variants in the variant set and the property, (ii) a plurality of substitutions at a position in the plurality of positions represented by all or the portion of the variants in the variant set and the property, or (iii) one or more substitutions in one or more positions in the plurality of positions represented by all or the portion of the variants in the variant set and the property.

In some embodiments, the modeling comprises regressing:

$$V_{measured} = W_{11}P_1S_1 + W_{12}P_1S_2 + + W_{1N}P_1S_N + + W_{M1}P_MS_1 + W_{M2}P_MS_2 + + W_{MN}P_MS_N$$

wherein, $V_{measured}$ represents the property measured in variants in the variant set;

$W_{MN}$=is a value in said plurality of values;

$P_M$=is a position in said biopolymer of interest in the plurality of positions in the biopolymer of interest; and $S_N$=is a substitution in the one or more positions for a position in the plurality of positions in the biopolymer of interest.

In some embodiments, this regressing comprises linear regression, non-linear regression, logistic regression, multivariate data analysis, or partial least squares projection to latent variables.

In some embodiments, the modeling comprises computation of a neural network, computation of a bayesian model, a generalized additive model, a support vector machine, or classification using a regression tree. In some embodiments, the modeling comprises boosting or adaptive boosting (See, for example, Hastie, *The Elements of Statistical Learning*, Springer, New York, 2003).

In some embodiments, the redefining further comprises (i) computing a predicted score for a population of variants of the biopolymer of interest using the sequence-activity relationship, wherein each variant in the population of variants includes a substitution at one or more positions in the plurality of positions in the biopolymer of interest and (ii) selecting the variant set from among the population of variants as a function of the predicted score received by each variant in the set of variants.

In some embodiments, the method further comprises ranking the population of variants, wherein each variant in the population of variants is ranked based on the predicted score received by the variant based upon the sequence-activity relationship, wherein the selecting comprises accepting a predetermined percentage of the top ranked variants in the population of variants for the variant set (e.g., top 5 percent, top 10 percent, top 20 percent, between top 1 percent and top 20 percent, etc.).

In some embodiments, a respective variant in the population of variants is selected for the variant set when the predicted score of the respective variant exceeds a predetermined value.

In some embodiments, the redefining step further comprises redefining the variant set to comprise one or more variants each having a substitution in a position in the plurality of positions not present in any variant in the variant set selected by the selecting step.

In some embodiments, the modeling of a sequence-activity relationship further comprises modeling a plurality of sequence-activity relationships. Each respective sequence-activity relationship in the plurality of sequence-activity relationships describes the relationship between (i) one or more substitutions at one or more positions of the biopolymer of interest represented by the variant set and (ii) the property measured for all or the portion of the variants in the variant set. Furthermore, the step of redefining the variant set (e) comprises redefining the variant set to comprise variants that include substitutions in the plurality of positions that are selected based on a combination of the plurality of sequence-activity relationships. In some such embodiments, the method further comprises (i) repeating the measuring based upon the redefined variant set, wherein a property of all or a portion of the variants in the redefined variant set is measured and (ii) weighting each respective sequence-activity relationship in the plurality of sequence activity relationships based on an agreement between (1) measured values for the property of variants in the redefined variant set and (2) values for the property of variants in the redefined variant set that were predicted by the respective sequence-activity relationship, wherein a first sequence-activity relationship that achieves better agreement between measured and predicted values than a second sequence-activity relationship receives a higher weight than the second sequence-activity relationship.

In some embodiments, the redefining step further comprises redefining the variant set to comprise one or more variants each having a substitution in a position in the plurality of positions not present in any variant in the variant set selected by the selecting step. In some embodiments, the redefining step further comprises redefining the variant set to comprise one or more variants each having a substitution in a position in the plurality of positions not present in any variant in the variant set selected by the selecting step.

In some embodiments, the contribution of each respective rule in the plurality of rules to the biopolymer sequence space is independently weighted by a rule weight in a plurality of rule weights corresponding to the respective rule. In such embodiments, the method further comprises, prior to the redefining step, the steps of (a) adjusting one or more rule weights in the plurality of rule weights based on a comparison, for each respective variant in the variant set, (1) a value assigned to the respective variant by said sequence-activity relationship, and (2) a score assigned by the plurality of rules to the respective variant, and (b) repeating the identifying step using the rule weights, thereby redefining the plurality of positions and, for each respective position in the plurality of positions, redefining the one or more substitutions for the respective position. Furthermore in such embodiments, the redefining step further comprises redefining the variant set to comprise one or more variants each having a substitution in a position in the redefined plurality of positions not present in any variant in the variant set selected by the initial selecting step.

In some exemplary embodiments, the modeling of a sequence-activity relationship further comprises modeling a plurality of sequence-activity relationships. Each respective sequence-activity relationship in the plurality of sequence-activity relationships in such exemplary embodiments describes the relationship between (i) one or more substitutions at one or more positions of the biopolymer of interest represented by the variant set and (ii) the property measured for all or the portion of the variants in the variant set. Furthermore, in such exemplary embodiments, the redefining the variant set step comprises redefining the variant set to comprise variants that include substitutions in the plurality of positions that are selected based on a combination function of the plurality of sequence-activity relationships. In some instances, the exemplary embodiment further comprise the step of repeating the measuring based upon the redefined variant set, such that a property of all or a portion of the variants in the redefined variant set is measured. Furthermore, each respective sequence-activity relationship in the plurality of sequence activity relationships is weighted based on an agreement between (i) measured values for the property of variants in the redefined variant set and (ii) values for the property of variants in the redefined variant set that were predicted by the respective sequence-activity relationship such that a first sequence-activity relationship that achieves better agreement between measured and predicted values than a second sequence-activity relationship receives a higher weight than the second sequence-activity relationship.

In some embodiments, the biopolymer of interest is a polypeptide, a polynucleotide, a small inhibitory RNA molecule (siRNA), or a polyketide. In some embodiments, the plurality of positions comprises five or more positions, ten or more positions, between five and thirty positions.

In some embodiments, the plurality of rules comprises (i) two or more rules or (ii) five or more rules. In some embodiments, a rule in the plurality of rules assigns a score to a variant of the biopolymer of interest by considering a lineup of a plurality of sequences that are homologous to the biopolymer of interest. In some embodiments, a rule in the plurality of rules assigns a score to a variant of the biopolymer of interest by considering structural variations in one or more three dimensional structures of biopolymers that are homologous to the biopolymer of interest. In some embodiments, a rule in the plurality of rules assigns a score to a variant of the biopolymer of interest by considering variations in a substitution matrix (e.g., a universal substitution matrix) for the biopolymer of interest. In some embodiments, a first rule in the plurality of rules assigns a score to a variant of the biopolymer of interest based upon a binding pocket analysis of a structural model of the biopolymer of interest or a structural model of a homolog of the biopolymer of interest. In some embodiments, the identifying step combines a score from each rule in the plurality of rules for a variant of a biopolymer of interest. This combining can comprise adding (i) a first score from a first rule in the plurality rules and (ii) a second score from a second rule in the plurality rules for the variant of a biopolymer of interest. Alternatively, this combining can comprise multiplying (i) a first score from a first rule in the plurality rules and (ii) a second score from a second rule in the plurality rules for the variant of a biopolymer of interest.

In some embodiments, the variant set consists of between 5 and 200 variants of the biopolymer of interest or between 15 and 50 variants of the biopolymer of interest. In some embodiments, selection of the variant set comprises applying a covering algorithm to the biopolymer sequence space. In some embodiments, selection of the variant set comprises applying complete factorial design, a $2^k$ factorial design, a $2^k$ fractional factorial design, a latin squares approach, a greco-latin squares approach, a Plackett-Burmann design, a Taguchi design, a monte carlo algorithm, a genetic algorithm, or combinations thereof, to the biopolymer sequence space.

In some one aspect of the invention, the measuring comprises synthesizing all or the portion of the variations in said variant set such that the property of a variant in the variant set is an antigenicity of the variant, an immunogenicity of the variant, an immunomodulatory activity of the variant, a catalysis of a chemical reaction by the variant, a specificity of catalysis of one chemical reaction over another chemical reaction by the variant, a catalysis of polymer synthesis by the variant, a catalysis of polymer degradation by the variant, a catalysis of a reaction by the variant that separates or resolves two or more chiral compounds, a specific activity of the variant, a thermostability of the variant, a stimulation or agonism of a signaling pathway by the variant, a specificity of agonism of one signaling pathway over another signaling pathway by the variant, an inhibition or antagonism of a signaling pathway by the variant, a specificity of agonism of one signaling pathway over another signaling pathway by the variant, an expression of the variant in a homologous host, an expression of the variant in a heterologous host, an expression of the variant in a plant cell, a susceptibility of the variant to an in vitro post-translational modification, or a susceptibility of the variant to an in vivo post-translational modification, cell-surface receptor surface density, cell surface receptor internalization rates, cell surface receptor post-translational modifications, binding of cellular growth factor receptors, binding of receptors or mediators of tumor-driven angiogenesis, binding of B cell surface antigens and proteins synthesized by or in response to pathogens, induction of antibody-mediated cell killing, antibody-dependent macrophage activity, histamine release, induction of or cross-reaction with anti-idiotype antibodies, immunogenicity, viral titer, level of expression of the biopolymer in a heterologous host, expression within a plant, susceptibility of the biopolymer to be modified inside a living cell, composition of a complex mixture of compounds whose composition has been altered by the action of the biopolymer, localization of a biopolymer within a cell or a part of a cell, pH optimum, synthesis of a polymer resulting from the action of a biopolymer, degradation of a polymer resulting from the action of a biopolymer, alteration of the properties of a cell for example alteration of the growth, replication or differentiation patterns of a cell or population of cells, therapeutic efficacy of an antibody, and/or modulation of a signaling pathway.

In some embodiments, the sequence-activity relationship has the form:

$$Y = f(w_1 x_1, w_2 x_2, w_i x_i)$$

wherein,

Y is a quantitative measure of said property;

$x_i$ is a descriptor of a substitution, a combination of substitutions, or a component of one or more substitutions, at one or more positions in said plurality of positions;

$w_i$ is a weight applied to descriptor $x_i$; and f( ) is a mathematical function.

In some embodiments, the modeling comprises regressing:

$$Y = f(w_1 x_1, w_2 x_2, w_i x_i).$$

In some instances this regressing comprises linear regression, non-linear regression, logistic regressing, or partial least squares projection to latent variables.

A second aspect of the present invention provides a method of weighting a plurality of selection rules for use in selecting a plurality of positions in a biopolymer of interest and, for each respective position in the plurality of positions, one or more substitutions for the respective positions. In the method, the plurality of selection rules is used to identify a plurality of positions in a biopolymer of interest and, for each respective position in the plurality of positions, one or more substitutions for the respective position such that (i) the plurality of positions and the one or more substitutions for each respective position in the plurality of positions collectively define a biopolymer sequence space and (ii) the contribution of each respective rule in the plurality of rules to the biopolymer sequence space is independently weighted by a rule weight in a plurality of rule weights corresponding to the respective rule. In the method variant set is selected. The variant set comprises a plurality of variants of the biopolymer of interest that is a subset of the biopolymer sequence space. A property of all or a portion of the variants in the variant set is measured. These measurements are used to model a sequence-activity relationship between (i) one or more substitutions at one or more positions of the biopolymer of interest represented by the variant set and (ii) the property measured for all or the portion of the variants in the variant set. Then, one or more rule weights in the plurality of rule weights is adjusted based on a comparison, for each respective variant in the variant set, (i) a value assigned to the respective variant by the sequence-activity relationship, and (ii) a score assigned by the plurality of rules to the respective variant. These steps of identifying, selecting, measuring, modeling, and adjusting are repeated for each biopolymer of interest in a plurality of biopolymers of interest.

In some embodiments, the method further comprises the steps of (i) modeling a sequence-activity relationship between (a) one or more substitutions at one or more positions of the biopolymer of interest represented by the variant set and (b) the property measured for all or the portion of the variants in the variants in the variant set, and (ii) redefining the variant set to comprise variants that include substitutions in the plurality of positions that are selected based on a function of the sequence-activity relationship. In some embodiments, the modeling a sequence-activity relationship further comprises modeling a plurality of sequence-activity relationships such that each respective sequence-activity relationship in the plurality of sequence-activity relationships describes the relationship between (i) one or more substitutions at one or more positions of the biopolymer of interest represented by the variant set and (ii) the property measured for all or the portion of the variants in the variant set. Furthermore, in such embodiments, the redefining the variant set comprises redefining the variant set to comprise variants that include substitutions in the plurality of positions that are selected based on a combination function of the plurality of sequence-activity relationships. Some such embodiments further comprise repeating the measuring using the redefined variant set such that a property of all or a portion of the variants in the redefined variant set is measured and then weighting each respective sequence-activity relationship in the plurality of sequence activity relationships based on an agreement between (i) measured values for the property of variants in the redefined variant set and (ii) values for the property of variants in the redefined variant set that were predicted by the respective sequence-activity relationship, wherein a first sequence-activity relationship that achieves better agreement between measured and predicted values than a second sequence-activity relationship receives a higher weight than said second sequence-activity relationship. In some embodiments, the redefining further comprises redefining the variant set to comprise one or more variants each having a substitution in a position in the plurality of positions not present in any variant in the variant set selected by the selecting step.

In some embodiments in accordance with this second aspect of the invention, the plurality of biopolymers of interest represent a biopolymer class (e.g., protein, deoxyribose nucleic acid (DNA), ribose nucleic acid (RNA), or polyketide, etc.). In some embodiments, the plurality of biopolymers of interest represents a biopolymer subclass (e.g., kinases, proteases, transcription factors, receptors, growth factors, PDGFs, EGFs, FGFs, SCF, HGF, TGFs, TNFs, insulin, IGFs, LIFs, oncostatins, CSFs, immunomodulators, cytokines, integrins, interleukins, adhesion molecules, thrombomodulatory molecules, thrombopoietin, erythropoietin, tissue plasminogen activator, protease inhibitors, angiostatins, defensins, interferons, chemokines, antigens from infectious pathogens, oncogene products, polymerases, depolymerases, phosphatases, cyclins, cyclin-dependent kinases, glycosidases, transferases, glycosyl transferases, methylases, methyl transferases, polyketide synthases, non-ribosomal peptide synthases, insecticidal proteins, cytochrome P450s, lipases, esterases, cutinases, terpene cyclases, transferases, glycosyl transferases, methylases, methyl transferases, antibodies, immunoconjugates, protein stability regulating sequences, promoter sequences, enhancer sequences, nucleic acid stability regulating sequences, introns, type II polyketides, type I polyketides, non-ribosomal peptides or terpenes).

In some embodiments, the plurality of biopolymers of interest represents a biopolymer class and the property is cell-surface receptor surface density, cell surface receptor internalization rates, cell surface receptor post-translational modifications, binding of cellular growth factor receptors, binding of receptors or mediators of tumor-driven angiogenesis, binding of B cell surface antigens and proteins synthesized by or in response to pathogens, induction of antibody-mediated cell killing, antibody-dependent macrophage activity, histamine release, induction of or cross-reaction with anti-idiotype antibodies, immunogenicity viral titer, level of expression of the biopolymer in a heterologous host, expression within a plant, susceptibility of the biopolymer to be modified inside a living cell, composition of a complex mixture of compounds whose composition has been altered by the action of the biopolymer, localization of a biopolymer within a cell or a part of a cell, pH optimum, synthesis of a polymer resulting from the action of a biopolymer, degradation of a polymer resulting from the action of a biopolymer, alteration of the properties of a cell for example alteration of the growth, replication or differentiation patterns of a cell or population of cells, therapeutic efficacy of an antibody and/or modulation of a signaling pathway.

Another embodiment of the present invention provides a computer program product for use in conjunction with a computer system, the computer program product comprising a computer readable storage medium and a computer program mechanism embedded therein. In such embodiments, the computer program mechanism comprises (i) a knowledge base comprising a plurality of rules, (ii) an expert module for constructing a variant set for a biopolymer of interest. The expert module comprises instructions for identifying, using the plurality of rules, a plurality of positions in the biopolymer of interest and, for each respective position in the plurality of positions, one or more substitutions for the respective position, wherein the plurality of positions and the one or more substitutions for each respective position in the plurality of positions collectively define a biopolymer sequence space. The expert module further comprises instructions for selecting a variant set, wherein the variant set comprises a plurality of variants of the biopolymer of interest and wherein the variant set is a subset of the biopolymer sequence space. The expert module further comprises instructions for measuring or receiving a measurement a property of all or a portion of the variants in the variant set. The expert module further comprises instructions for modeling a sequence-activity relationship between (i) one or more substitutions at one or more positions of the biopolymer of interest represented by the variant set and (ii) the property measured for all or the portion of the variants in the variant set. The expert module further comprises instructions for redefining the variant set to comprise variants that include substitutions in the plurality of positions that are selected based on a function of the sequence-activity relationship.

Still another aspect of the present invention provides a computer system comprising a central processing unit and a memory, coupled to the central processing unit. The memory stores a knowledge base and an expert module. The knowledge base comprises a plurality of rules. The expert module is for constructing a variant set for a biopolymer of interest and comprises instructions for identifying, using the plurality of rules, a plurality of positions in the biopolymer of interest and, for each respective position in the plurality of positions, one or more substitutions for the respective position, wherein the plurality of positions the one or more substitutions for each respective position in the plurality of positions collectively define a biopolymer sequence space. The expert module further comprises instructions for selecting a variant set. This variant set comprises a plurality of variants of the biopolymer of interest and represents a subset of the biopolymer sequence space. The expert module further comprises instructions for measuring or receiving a measurement a property of all or a portion of the variants in the variant set and instructions for modeling a sequence-activity relationship between (i) one or more substitutions at one or more positions of the biopolymer of interest represented by the variant set and (ii) the property measured for all or the portion of the variants in the variant set. The expert module further comprises instructions for redefining the variant set to comprise variants that include substitutions in the plurality of positions that are selected based on a function of the sequence-activity relationship.

4. BRIEF DESCRIPTION OF THE DRAWINGS

FIG. 3 illustrates a flowchart for an antibody engineering method using integrated information sources to choose initial substitutions, and sequence-activity relationships to assess them in accordance with an embodiment of the present invention.

FIG. 5 is a schematic representation of a method for selecting amino acid substitutions for the optimization or humanization of antibodies in accordance with an embodiment of the present invention.

FIG. 8 illustrates the amino acid sequence of wild type proteinase K, reported by Gunkel et al., 1989, Eur J Biochem 179: 185-194, modified by (i) replacement of the fungal leader peptide with an *E. coli* leader peptide, amino acids −20 to −1 (SEQ ID No. 1), and (ii) addition of a histidine tag to the C terminus (amino acids 372-377), together with a ValAsp preceding the tag (amino acids 370 and 371) to accommodate cloning sites in the nucleic acid sequence.

FIG. 9 illustrates the nucleotide sequence of proteinase K optimized for expression in *E coli*. The *E coli* leader peptide (amino acids −20 to −1 in FIG. 8) are encoded by nucleotides −60 to −1 in FIG. 9. The proteinase K sequence, beginning with Ala at amino acid 1 and ending with Ala at amino acid 369, is encoded by nucleotides 1-1107. The histidine tag, the two additional amino acids described in FIG. 8 and the termination codon are encoded by nucleotides 1108-1133.

FIG. 10 lists the genetic identifiers of 49 proteinase K homologs obtained by BLAST searching of GENBANK.

Figure 11:
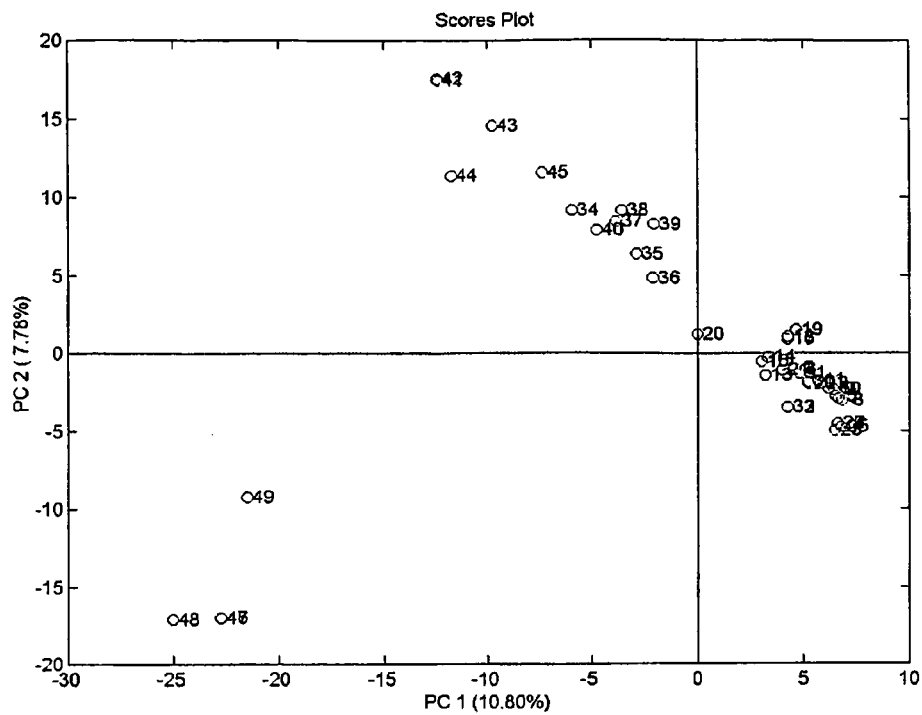

FIG. 11 illustrates a distribution of proteinase K homolog sequences (shown in FIG. 10) in the first two principal components of the sequence space. Sequences 46-49 are derived from thermostable organisms.

Figure 12:
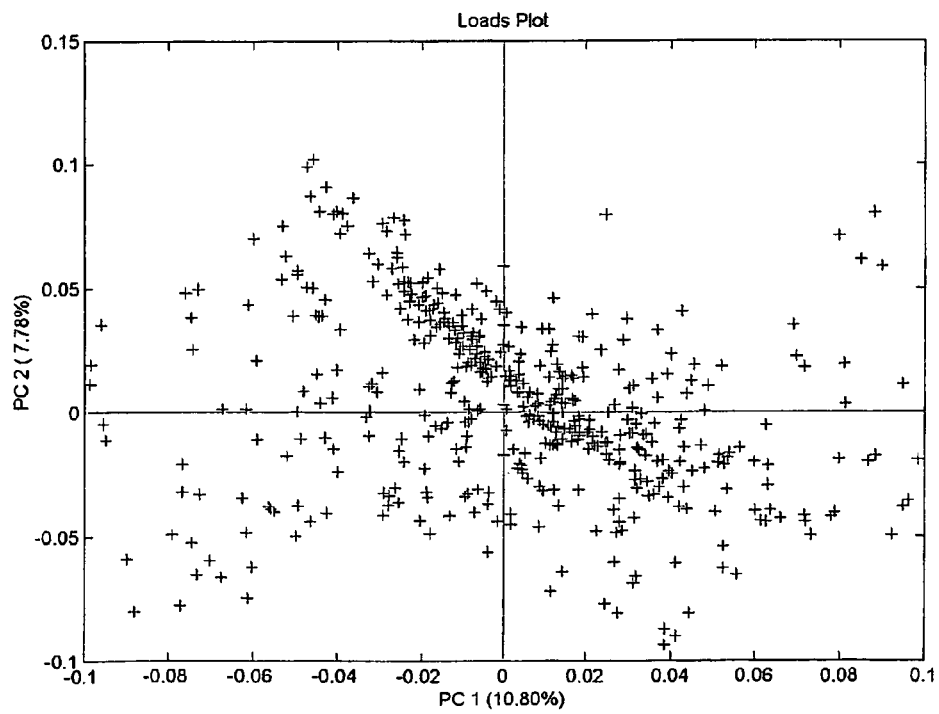

FIG. 12 illustrates a corresponding plot of all loads describing the influence of each variable on the sample distribution of FIG. 11

Figures 13, 14:
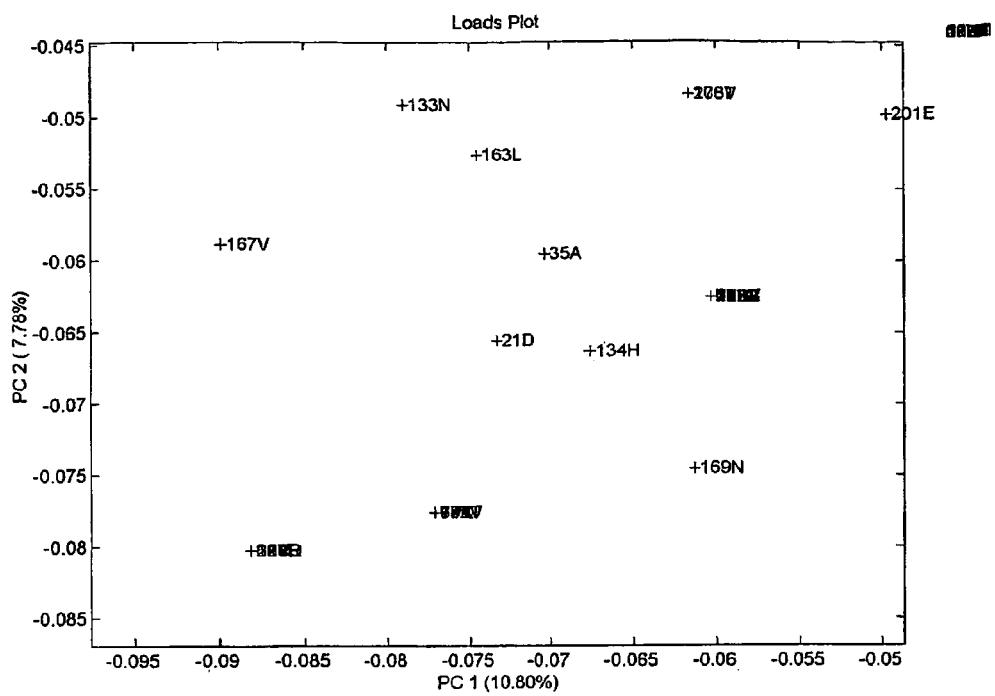

FIG. 13 provides magnified detail of the bottom left quadrant from FIG. 12.

FIG. 14 provides principal component analysis-derived loads for individual amino acids responsible for clustering of thermostable proteinase K homologs.

FIG. 15 illustrates sample output from an Expert System defining the 24 most highly scoring substitutions to be incorporated into a set of variants for initial mapping of proteinase K sequence-activity space in accordance with an embodiment of the present invention.

FIG. 16 illustrates a first designed set of 24 variants for proteinase K. Each variant contains six substitutions from the wild type sequence. The numbers refer to the substitutions identified in FIG. 15.

FIG. 17 illustrates a second designed set of variants for proteinase K.

FIGS. 18A-18F illustrate amino acid changes in a set of synthesized proteinase K variants. Each column shows the changes from the wild type sequence present in one variant. A blank cell indicates the wild type sequence at that position. Amino acid numbering is shown in FIG. 8.

Figures 19B, 20:
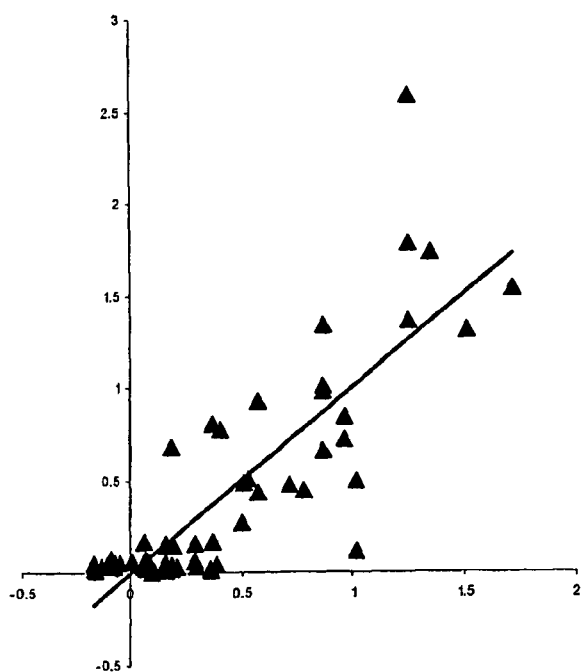

FIGS. 19A and 19B provide activity measurements of proteinase K variants. Proteinase K variants were assessed for six different hydrolytic activities. All activities are normalized to the average performance of the wild type proteinase K. In FIGS. 19A and 19B, y1: hydrolysis of a modified tetrapeptide, N-succinyl-Ala-Ala-Pro-Leu-p-nitroanilide (AAPL-p-NA) by purified proteinase K variants at pH 7.5; y2: thermostability ratio: activity after heat/activity without heat treatment, y6/y1; y4: hydrolysis of a modified tetrapeptide, N-succinyl-Ala-Ala-Pro-Leu-p-nitroanilide (AAPL-p-NA) by purified proteinase K variants at pH 4.5; y5: hydrolysis of a modified tetrapeptide, N-succinyl-Ala-Ala-Pro-Leu-p-nitroanilide (AAPL-p-NA) by purified proteinase K variants at pH 5.5; y6: hydrolysis of a modified tetrapeptide, N-succinyl-Ala-Ala-Pro-Leu-p-nitroanilide (AAPL-p-NA) at pH 7.5 by purified proteinase K variants which have been exposed to a heat treatment of 65° C. for 5 minutes; and y7: hydrolysis of casein measured as clearing zones, in an LB agar plate containing 2% skimmed milk, around a bacterial colony expressing the variant. Duplicate values indicate that a variant's activity was measured on two separate occasions.

FIG. 20 illustrates a comparison between values predicted and values measured for a protein sequence-activity model derived from sequences shown in FIG. 18 and activity data (y6) shown in FIG. 19. Measured activities of proteinase K variant activities towards AAPL-p-NA following a five minute 65° C. heat treatment on the y-axis are compared with those predicted by the model on the x-axis. All activities were measured at 37° C. and pH 7.0 using purified protein.

Figure 21:
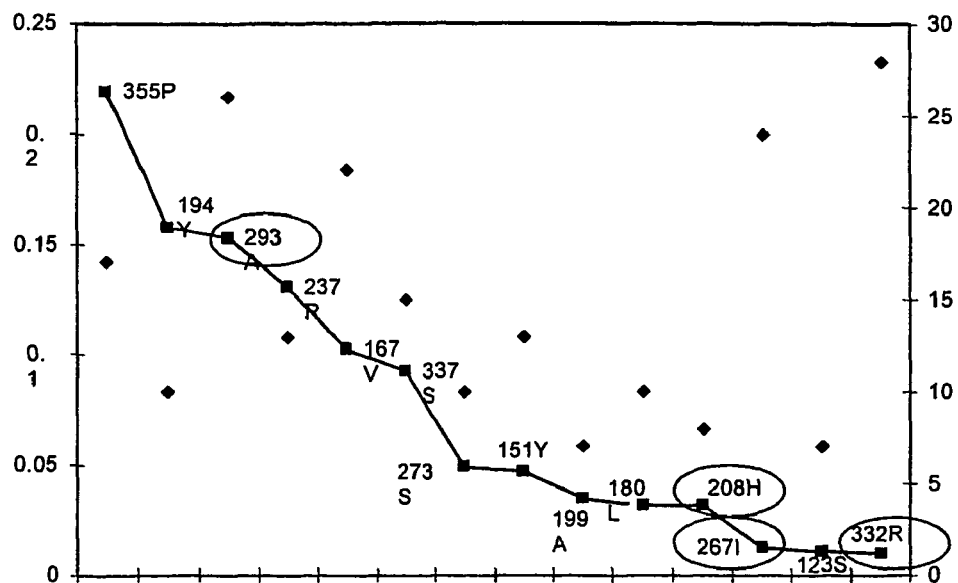

FIG. 21 illustrates the identification of amino acids contributing to a specific function from a sequence-activity model. Regression coefficients (squares, left axis) of variant amino acids were derived from the sequence-activity model relating the sequences of proteinase K sequence variants (with numbers lower than 49) to activity y6. The number of occurrences of each amino acid substitution are also shown (diamonds, right axis). Changes from the wild type sequence are circled.

Figure 22:
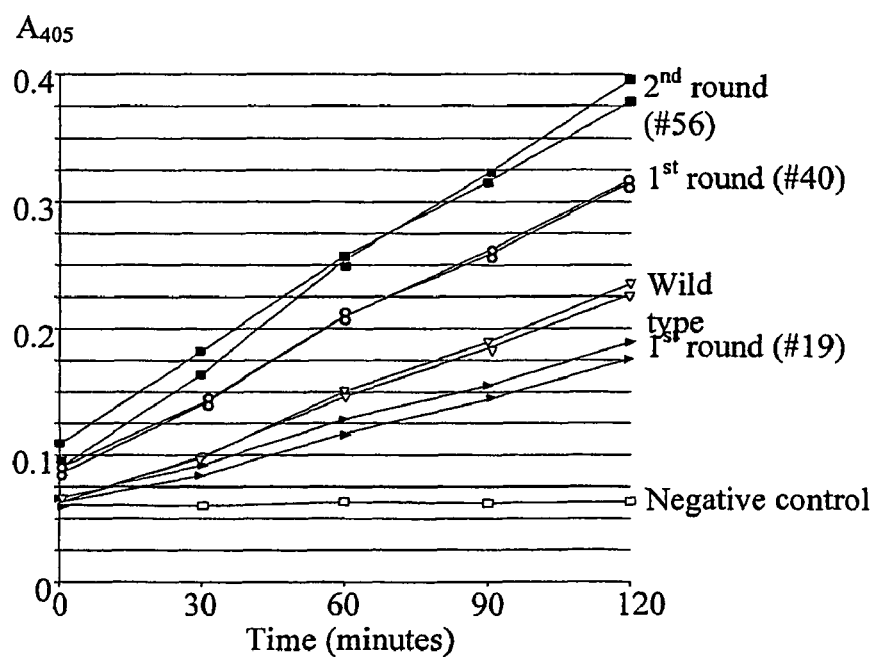

FIG. 22 illustrates the use of sequence-activity modeling to design a new variant with improved activity. Four amino acid substitutions were found to have positive regression coefficients in their contribution to activity following heat-treatment (y6). The variant test set contained one variant with one of these changes (#19) and one with three of these changes (#40). A new variant (#56) was synthesized to contain all four changes. The graph shows the activity of these variants towards AAPL-p-NA following five minute 65° C. heat treatment. Purified proteins were heated to 65° C. then incubated with AAPL-p-NA at pH 7.5. The reaction was followed by measuring the absorbance at 405 nm. Alterations from the wild type sequence are: #19, K208H (filled triangles); #S40, V267I, G293A, K332R (open circles); #56, K208H, V267I, G293A, K332R (filled squares).

Figures 23, 24:
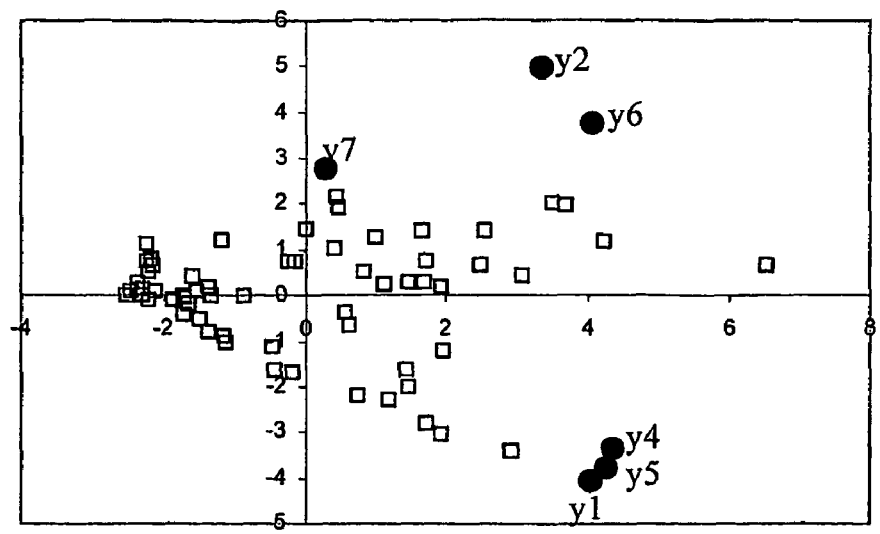

FIG. 23 illustrates principal component analysis of proteinase K variant activities. Six measured proteinase K properties are shown compressed into two principal components using mean-centered auto-scaling. PC1 (horizontal axis) captures 60% of variance, PC2 (vertical axis) captures 22% of variance. Open squares represent each proteinase K variant, filled circles show the positions of each property in principal component space.

FIG. 24 illustrates how different amino acids are important for different functions in proteinase K. Beneficial amino acid substitutions were calculated by sequence-activity modeling for three different proteinase K properties. Changes from the wild type sequence are underlined.

FIG. 25 illustrates a Taguchi matrix for optimally distributing seven 2-state variables.

FIG. 26 is a schematic representation of a method for selecting amino acid substitutions for the optimization of prolyl endopeptidase in accordance with an embodiment of the present invention.

Figure 27:
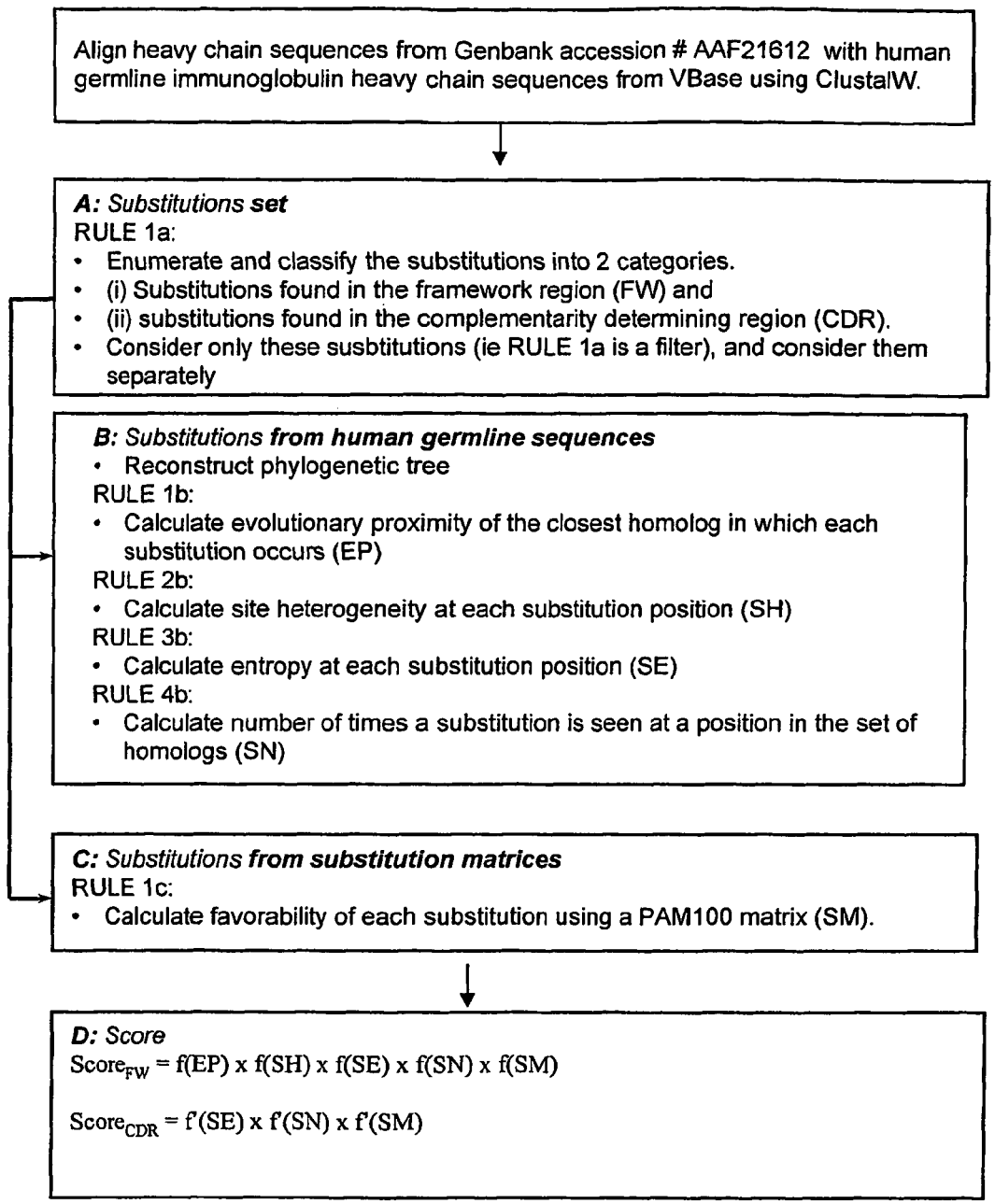

FIG. 27 is a schematic representation of a method for selecting amino acid substitutions for the optimization of antiviral activity of an antibody in accordance with an embodiment of the present invention.

FIG. 28 is a schematic representation of a method for selecting amino acid substitutions for the humanization of an antibody in accordance with an embodiment of the present invention.

5. DETAILED DESCRIPTION OF THE INVENTION

Figure 2:
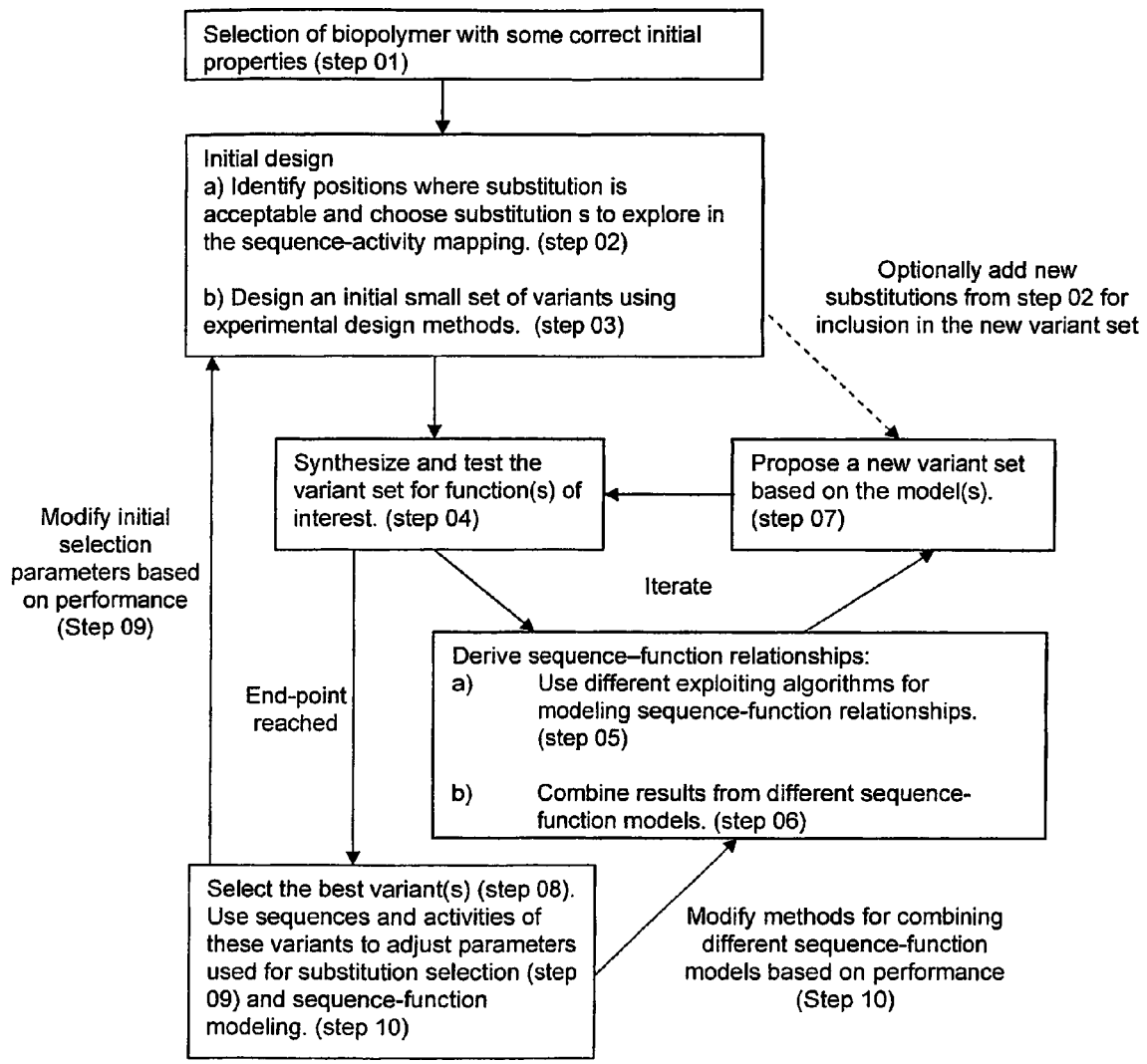
FIG. 2 illustrates a protein engineering method using integrated information sources to choose initial substitutions, and sequence-activity relationships to assess them in accordance with an embodiment of the present invention.

A general biopolymer optimization scheme is shown in FIG. 2, in FIG. 3 this general scheme is shown specifically for optimizing the function of an antibody, which is one class of biopolymers. The steps found in FIG. 2 will be briefly introduced here and described in more detail below.

Step 01. A biopolymer or a plurality of biopolymers that partially achieves the desired property (e.g., function) is used as a starting point (step 01).

Step 02. Substitutions to a sequence of step 01 are identified using a combination of changes to the sequence. Such changes are either in monomer identity or in monomer physico-chemical properties. For example, consider the case in which the biopolymer is a 20-mer peptide. In step 02, a determination can be made that the $2^{nd}$ and $4^{th}$ positions can be changed. Moreover, in some embodiments, a determination is made as to which substitutions can be made at such positions in step 02. For instance, step 02 may not only determine that the $2^{nd}$ position of the 20-mer can be changed, but may also determine that this position should be changed to a glycine, alanine, or leucine.

In typical embodiments, several independent rules are used to determine which positions of the biopolymer of step 01 can be changed. Each such rule scores or ranks individual substitutions based on a different technique. Representative rules include, but are not limited to, rules based on (i) changes found in functional, structural or sequence homologs, (ii) changes predicted to be favorable using substitution matrices, (iii) changes predicted using evolutionary analysis of the homologs, (iv) changes seen in random mutagenesis screening, (v) changes predicted by structural modeling, (vi) changes proposed by an expert on the protein and (vii) changes predicted to be favorable using structural information. Any number of rules can be applied to the one or more biopolymers of step 01.

In some embodiments of the present invention, each independent rule assigns a score for each possible substitution position (e.g. residue) in the biopolymer of step 01. The scores generated by each of the rules are then combined by methods and/or filters to determine the positions in the biopolymer that are suitable for change.

Step 03. Step 02 identified a set of candidate substitution positions in the biopolymer of step 01. In step 03, a variant set incorporating such candidate substitutions is designed such that each candidate substitution is tested in combination with many different other candidate substitutions in order to cover the possible search space as evenly as possible (step 03).

To illustrate, consider the case in which the biopolymer of step 01 is a 20-mer peptide and the $2^{nd}$, $5^{th}$, and $15^{th}$ residue in the 20-mer has been identified as candidate substitution positions in step 03. Assuming that each of these three positions can be independently substituted and considering only the twenty naturally occurring amino acids, there are $20^3-1$ different variant biopolymers that could be constructed. In some instances, step 02 will constrain the types of amino acids that can be substituted at these positions based on the rules described above. Nevertheless, the full biopolymer sequence space proposed in step 02 even after filtering can be large. Step 03 seeks to minimize the number of variants that are constructed in order to evenly search this large sequence space.

Step 04. Variant biopolymers selected in step 03 are individually synthesized and tested for one or more functions (one or more properties) of interest in step 04. When the variant biopolymers are synthesized individually it is easier to keep the number of changes and the number of variants synthesized and tested in each iteration of the process relatively small. In some embodiments, between 5 and 200, more preferably between 10 and 100, and even more preferably between 15 and 50 variants are synthesized and tested in step 04. By minimizing the number of variants synthesized and tested, relatively inaccurate high throughput assay screens can be avoided in step 04. In some embodiments, the property measured in step 04 is said property of a variant in said variant set is an antigenicity of said variant, an immunogenicity of said variant, an immunomodulatory activity of said variant, a catalysis of a chemical reaction by said variant, a specificity of catalysis of one chemical reaction over another chemical reaction by the variant, a catalysis of polymer synthesis by the variant, a catalysis of polymer degradation by the variant, a catalysis of a reaction by the variant that separates or resolves two or more chiral compounds, a specific activity of the variant, a thermostability of the variant, a stimulation or agonism of a signaling pathway by the variant, a specificity of agonism of one signaling pathway over another signaling pathway by the variant, an inhibition or antagonism of a signaling pathway by the variant, a specificity of agonism of one signaling pathway over another signaling pathway by the variant, an expression of the variant in a homologous host, an expression of the variant in a heterologous host, an expression of the variant in a plant cell, a susceptibility of the variant to an in vitro post-translational modification, a susceptibility of the variant to an in vivo post-translational modification, a cell-surface receptor surface density of the variant, a cell surface receptor internalization rate of the variant, a cell surface receptor post-translational modification of the variant, a binding of a cellular growth factor receptor, a binding of receptors or mediators of tumor-driven angiogenesis, a binding of B cell surface antigens and proteins synthesized by or in response to pathogens, an induction of antibody-mediated cell killing, an antibody-dependent macrophage activity, a histamine release, an induction of or cross-reaction with anti-idiotype antibodies, an immunogenicity of the variant, a viral titer, a level of expression of the biopolymer in a heterologous host, an expression within a plant, a susceptibility of the variant to modification inside a living cell, a composition of a complex mixture of compounds whose composition has been altered by the action of the variant, a localization of a biopolymer within a cell or a part of a cell, a pH optimum, a synthesis of a polymer resulting from the action of a biopolymer, a degradation of a polymer resulting from the action of a biopolymer, an alteration of the properties of a cell (e.g., alteration of the growth, replication or differentiation patterns of a cell or population of cells), a therapeutic efficacy of an antibody, and or a modulation of a signaling pathway.

Step 05. Various machine-learning methods or other data-mining techniques are used to model the relationship between the sequences and activities of the variant biopolymer in step 05.

Step 06. The assessments of the affect of each substitution upon the properties (functions) of the biopolymer by each model tested in step 05 are combined in step 06.

Step 07. The assessments of the affect of each substitution upon the properties (functions) of the biopolymers by each tested model that was made in step 06 is used in step 07 to design a new set of variant biopolymers for synthesis and testing Repeating steps 04-07. Steps 04 through 07 are repeated a number of times. Each iteration of steps 04-07 seeks to design a set of high scoring and diverse biopolymers (e.g., proteins, peptides, oligonucleotides) for synthesis and functional testing. Each new set of measurements from an iteration of step 04 is used to refine the sequence-activity model until an end point is reach, at which point the method progresses to step 08.

Step 08. The performance of the methods used to select substitution positions in step 02 and to model the sequence-activity relationships in instances of step 05 are assessed by analyzing the sequences of the best performing variants. In general, the best performing variants are any variants in any iteration of the cycle defined by steps 04-07 that score best in one or more functional assays for the target biopolymer. Step 08 provides a method for tuning the adjustable parameters of the system. Once these parameters have been adjusted, steps 02 through 07, including multiple iterations of the cycle defined by steps 04-07, are repeated. Advantageously, one of the adjustable parameters of the system is the individual weights for each of the methods applied in step 02. For example, those step 02 method that were good at identifying substitution positions associated with high scoring biopolymer variants are up-weighted in the next instance of steps 02 through 07. The modification of weights applied to methods in step 02 based on the results of cycles of steps 04-07 allows the system to learn from previous results thereby improving the accuracy with which the system can identify beneficial substitutions (in step 02) and assess the contribution of substitutions to biopolymer activity (in steps 05 and 06).

5.1 Expert Systems for Defining a Sequence Space

FIG. 1 details an exemplary system that supports the functionality described above. The system is preferably a computer system 10 having:

- a central processing unit 22;
- a main non-volatile storage unit 14, for example a hard disk drive, for storing software and data, the storage unit 14 controlled by storage controller 12;
- a system memory 36, preferably high speed random-access memory (RAM), for storing system control programs, data, and application programs, comprising programs and data loaded from non-volatile storage unit 14; system memory 36 may also include read-only memory (ROM);
- a user interface 32, comprising one or more input devices (e.g., keyboard 28) and a display 26 or other output device;
- a network interface card 20 for connecting to any wired or wireless communication network 34 (e.g., a wide area network such as the Internet);

an internal bus 30 for interconnecting the aforementioned elements of the system; and a power source 24 to power the aforementioned elements.

Operation of computer 10 is controlled primarily by operating system 40, which is executed by central processing unit 22. Operating system 40 can be stored in system memory 36. In a typical implementation, system memory 36 includes:

operating system 40;
file system 42 for controlling access to the various files and data structures used by the present invention;
a user interface 104;
an expert system 100;
case-specific data 110; and
knowledge base 108.

Figure 1:
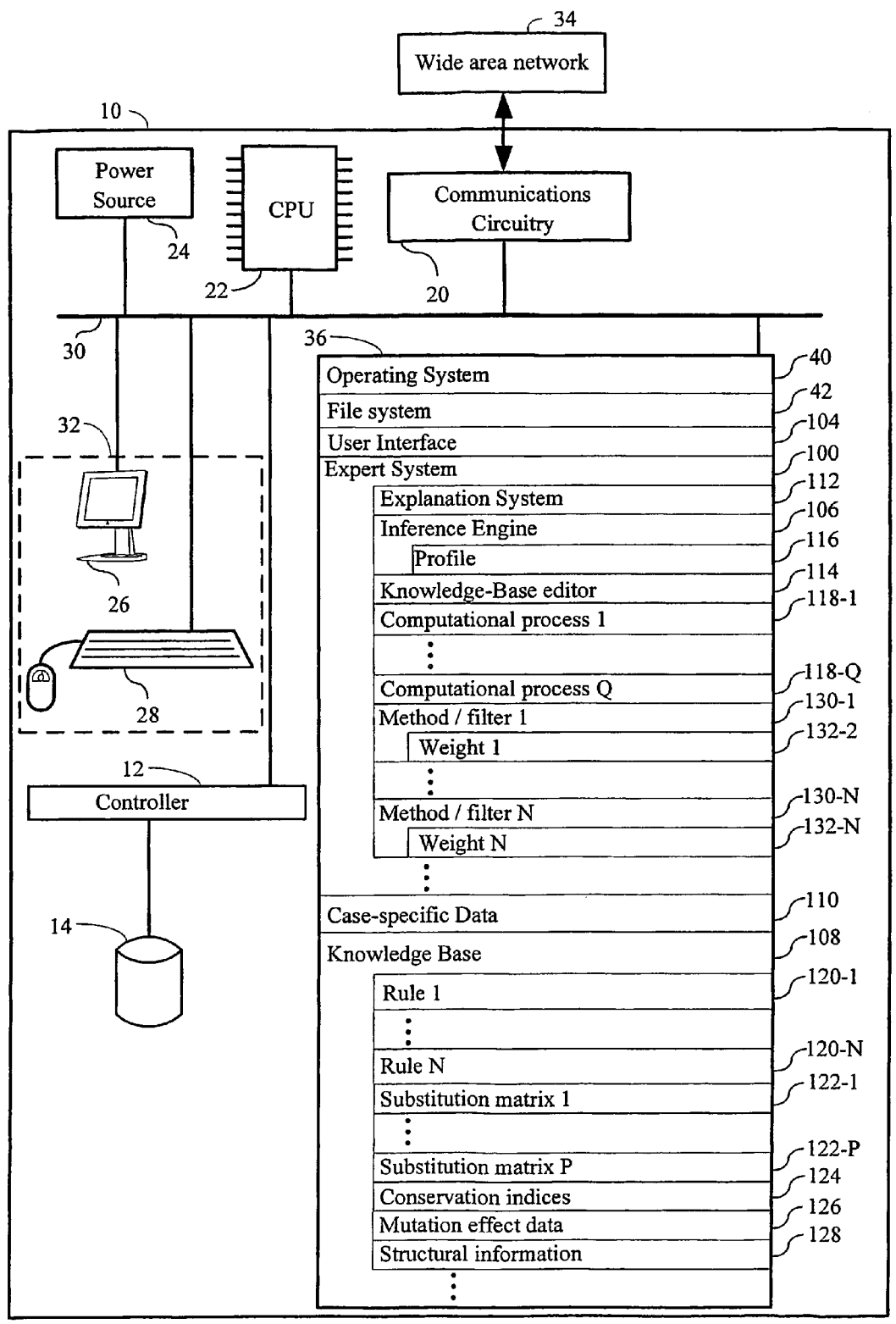
FIG. 1 illustrates an overview of the architecture of an Expert System in accordance with an embodiment of the present invention.

As illustrated in FIG. 1, computer 10 comprises case-specific data 110 and knowledge base 108. Case-specific data 110 and knowledge base 108 each independently comprise any form of data storage system including, but not limited to, a flat file, a relational database (SQL), and an on-line analytical processing (OLAP) database (MDX and/or variants thereof). In some specific embodiments, case-specific data 110 and/or knowledge base 108 is a hierarchical OLAP cube. In some specific embodiments, case-specific data 110 and/or knowledge base 108 comprises a star schema that is not stored as a cube but has dimension tables that define hierarchy. In some embodiments, case-specific data 110 and/or knowledge base 108 is respectively a single database. In other embodiments, case-specific data 110 and/or knowledge base 108 in fact comprises a plurality of databases that may or may not all be hosted by the same computer 10. In such embodiments, some component databases of case-specific data 110 and/or knowledge base 108 are stored on one or more computer systems that are not illustrated by FIG. 1 but that are addressable by wide area network 34.

It will be appreciated that many of the modules illustrated in FIG. 1 can be located on one or more remote computers. For example, some embodiments of the present application are accessible in web service-type implementations. In such embodiments, user interface module 104 and other modules can reside on a client computer that is in communication with computer 10 via network 34. In some embodiments, for example, user interface 104 can be an interactive web page.

In some embodiments, the case-specific data 110 and/or knowledge base 108 and modules (e.g. modules 100, 104, 112, 106, 116, 114, 118, 130, 132) illustrated in FIG. 1 are on a single computer (computer 10) and in other embodiments such data is hosted by several computers (not shown). Any arrangement of case-specific data 110 and knowledge base 108 and the modules illustrated in FIG. 1 on one or more computers is within the scope of the present invention so long as these components are addressable with respect to each other across network 34 or by other electronic means. Thus, the present invention fully encompasses a broad array of computer systems.

Now that an overview of a computer system and the data structures stored in such a computer system has been presented, more details on the inventive data structures and software modules of the present invention will be described.

Expert system 100 is a software module that includes stored knowledge and solves problems in a specific field (for example biopolymer engineering) by emulating some of the decision processes of a human expert(s). The first set of algorithms that chooses the substitutions and the sequence space to explore for biopolymer engineering (steps 02 and 03 of FIG. 2) may require expertise in the domains of polynucleotide structure and function, polyketide structure and function, terpene structure and function, protein science, protein structural analysis and interpretation, protein structure and function, protein and nucleic acid phylogeny and evolution, chemical and enzymatic mechanisms, bioinformatics and related fields. Expert system 100 applies the knowledge to problems specified by a user who is not necessarily an expert in the domain(s). This invention describes the construction and use of expert system 100 for selecting substitutions useful for mapping and engineering biopolymer functions.

Two functions expert system 100 provides in order to define a sequence space to search are (i) the identification of one or more positions in the biopolymer at which substitution is likely to be accepted and where at least some substitutions, insertions, deletions or modifications are likely to result in a functional biopolymer and (ii) the identification of residues or modifications that are likely to result in a functional biopolymer when used to substitute or insert at each of the one or more positions identified in (i). An additional or alternative purpose of expert system 100 is the identification of residues or modifications that are likely to affect the desired properties or functions of the biopolymer. These functions are represented as step 02 in both FIGS. 2 and 3.

Methods for identification of residues that contribute to specific functions are known in the art. See, for example, del Sol Mesa et al., 2003, J Mol Biol 326:1289-302, Casari et al., 1995, Nat Struct Biol. 2:171-8, Gogos et al., 2000, Proteins 40:98-105. One aspect of this invention is the use of these methods to identify positions that can be varied, then to synthesize a set of biopolymers containing these substitutions and to test the biopolymers for one or more property or function, with the aim of deriving relationships between biopolymer sequence and function.

A user can interact with expert system 100 using user interface 104. In some embodiments, user interface 104 comprises menus, natural language or any other style of interaction. Expert system 100 uses inference engine 106 to reason using the expert knowledge stored in knowledge database 108 together with case-specific data 110 relating to the specific biopolymer or class of biopolymers to be mapped and/or engineered. Case-specific data 110 can be acquired as input from the user of expert system 100, presented in knowledge base 108, or acquired from case-specific knowledge generated by the results of experimentation and the analysis facilitated by sequence-activity correlating methods of this invention described in further detail below. These sequence-activity correlating methods are performed in step 05 of FIG. 2, for example. The data from these sequence-activity correlating methods can additionally be used to add to or alter the information contained within knowledge base 108.

Expert knowledge will typically be stored in knowledge base 108 in the form of a set of rules 120. An exemplary rule 120 is:

IF (a protein or polynucleotide has known variants that possess some activity)
THEN {
    assign probabilities for incorporating the variant residues based on their occurrence in some set of other naturally occurring proteins or polynucleotides using a substitution matrix to determine the likelihood of such a substitution occurring in nature
}
Another exemplary rule 120 is:
IF (desired activity is thermostability)
THEN{
    Change weights used to score/rank the substitutions found in known thermostable homologs.
}

Figure 4:
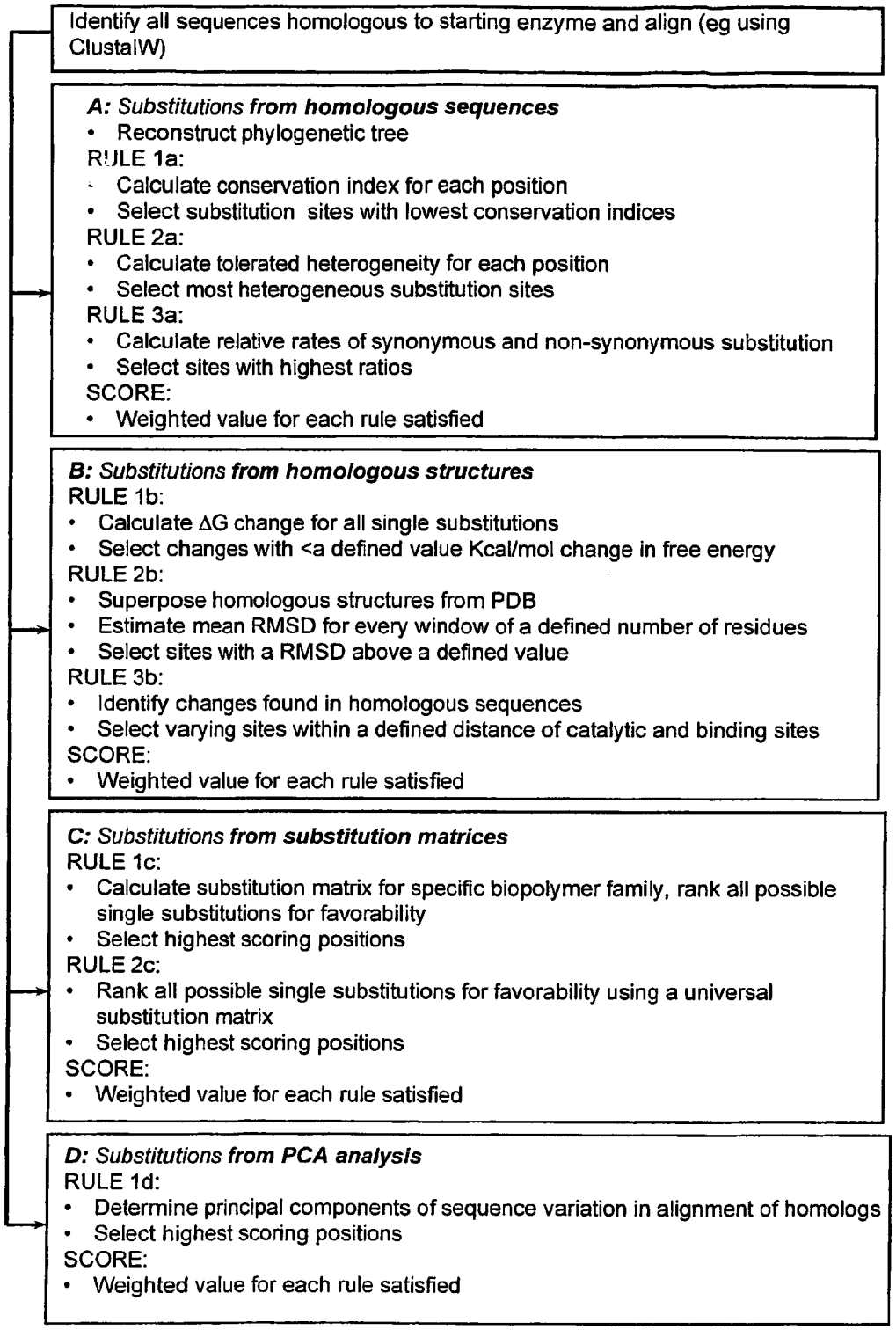
FIG. 4 is a schematic representation of a method for selecting amino acid substitutions for the optimization of protein function in accordance with an embodiment of the present invention.

Additional examples of rules 120 are each of the filters described in FIGS. 4 and 5.

Case-specific data 110 can be precompiled by experts. It can also be obtained as user response to questions contained in a component of expert system 100, for example user interface 104, knowledge base 108 or inference engine 106.

The functionality relied on by rules 120 of expert system 100 can also be obtained, in part, by a set of automatic actions executed using one or more computational processes 118. An example of a computational process 118 is:

Upon input of a target sequence (from Step 01) {
202 Search one or more sequence databases for homologs of the target biopolymer sequence. Store any such homolog sequences in knowledge base 108
204 Identify any functional information provided for any of these target biopolymer sequence homologs by any of these databases. Store any such homolog functional information in knowledge base 108
206 Search one or more structure databases for homologs of the target biopolymer sequence. Store any such homolog structural information in knowledge base 108.
208 Search one or more databases for known variants of the target biopolymer sequence. Store any sequence and functional information in knowledge base 108.
210 Compute the scores for every enumerated substitution found in steps 202 through 208 using select rules 120.

Computational processes 118 can be stored in knowledge base 108 as illustrated in FIG. 1, in expert system 100, or in any data structure that is accessible by expert system 100. Some embodiments of expert system 100 include explanation subsystem 112. Explanation subsystem 112 provides reasons to the user for why particular substitutions are selected by rules 120. Some embodiments of expert system 100 include knowledge base editor 114 to allow an administrator to add, delete, or modify components of knowledge base 108 including, but not limited to, rules 120.

In some embodiments, expert system 100 provides scores for each substitution enumerated along with the contribution to that score from various methods 130 used to evaluate the desirability of each substitution. The weights 132 for the various methods 130 are derived from knowledge base 108 and can be updated by an expert using knowledge base editor 108 and can also be updated automatically using rules in knowledge base 108.

Inference engine 106 is a software module that reasons using information stored in knowledge base 108. One embodiment of inference engine 106 is a rule-based system. Rule-based systems typically implement forward or backward chaining strategies. Inference engine 106 can be goal driven using backward chaining to test whether some hypothesis is true, or data driven, using forward chaining to draw new conclusions from existing data. Various embodiments of expert system 100 can use either or both strategies. For example, some topics that can be posed by expert system 100 in a goal driven/backward chaining strategy can include: (i) how conservative should an approach be; (ii) how many iterations of the process are likely to achieve the activity of interest, (iii) by what factor should the desired activity increase, and (iv) descriptions of any prior experiments that have failed and why they have failed. Answers to these topics allows expert system 100 to access information from experiments and data from the scientific literature or from personal communications that can be relevant for the design of the sequence space of interest.

Inference engine 106 can calculate a probability that a variant residue will provide a desired activity in a biopolymer of interest. The biopolymer can be a peptide, a protein, a polynucleotide having its own activity of interest, a polynucleotide that encodes a polypeptide having an activity of interest, or a polynucleotide that encodes a polypeptide that is responsible for synthesis of a biopolymer having an activity of interest. Biopolymers can further include polynucleotides exhibiting catalytic activity (e.g., ribozymes), polynucleotides exhibiting binding activity (e.g., aptamers), polynucleotides exhibiting promoter activity, or polynucleotides exhibiting any other desired activity, alone or in combination with any other molecule. Biopolymers can also include polysaccharides, polyketides, non-ribosomally synthesized polypeptides and/or the polypeptides involved in the synthesis of polysaccharides, polyketides or non-ribosomally synthesized polypeptides.

A profile 116 can be created by inference engine 106 based on probability scores and weighting factors. In some embodiments, inference engine 106 calculates the probability that defined substitutions will result in a biopolymer having the desired function, for any variant of the reference biopolymer. For example, in some instances, knowledge base 108 can contain information describing residue positions in the reference sequence that exhibit a high degree of variance in homologs. Inference engine 106 may thus give a high probability that substitutions at such positions will be active. One method of calculating the degree of amino acid variance is described by Gribskov, 1987, Proc Natl Acad Sci USA 84, 4355. As another example, in some instances, a sequence alignment can be available in knowledge base 108 to serve as the basis of a Hidden Markov model that can be used to calculate the probability that one specific residue will be followed by a second specific residue. These models also include probabilities for gaps and insertions. See, Krogh, "An introduction to Hidden Markov models for biological sequences," in *Computational Methods in Molecular Biology*, Salzberg et al., eds, Elsevier, Amsterdam. Such models can be used by inference engine 106 to calculate the probability that a particular substitution will possess a desired function.

In some embodiments of the present invention, a variety of different substitution matrices 122 stored in knowledge base 108 can be used by expert system 100 to identify suitable replacement residues for positions likely to accept substitutions. In addition, the availability of a replacement residue that is likely to be functional can itself determine whether or not a position is likely to accept substitutions. Substitution matrix 122 choices will impact the probability calculated for likely functionality of a variant. Thus, if mutations based on sequence alignment are desired, a substitution matrix 122 derived from the set of sequences should be chosen. Alternatively, if mutations that depend on general mutability are desired, a substitution matrix 122 reflecting this need should be chosen. Substitution matrices 122 can be calculated based on the environment of a residue, e.g., inside or accessible, in alpha-helix or in beta-sheet. See, for example, Overington et al., 1992, Protein Sci 1:216.

Methods to identify solvent accessible residues and to compute their solvent availability are known in the art. See, for example, Hubbard, Protein Eng 1:159 (1987). Such calculated solvent availability can be used to determine which substitution matrix 122 is used. More complex substitution matrices 122 that consider secondary structure, solvent accessibility, and the residue chemistry are also suitable for use in probability matrices. See, for example, Bowie & Eisenberg, Nature 356:83 (1992).

Conservation indices 124 stored in knowledge base 108 can be also be used by inference engine 106 to calculate probabilities that a substitution will result in a biopolymer with desired properties. In this capacity, one can avoid mutating residues that are highly conserved, or conversely, focus mutations on conserved regions of the biopolymer. Algorithms for calculating conservation indices 124 at each position in a multiple sequence alignment are known in the art. See, for example, Novere et al., 1999 Biophys. Journal 76:2329-2345.

Inference engine 106 can also use knowledge of the effects of single mutations as a factor in calculating the probability that a substitution will possess a desired function when mutation effect data 126 is stored in knowledge base 108. Mutation effect data 126 can originate, for example, from mutagenesis scans or from those substitutions found in naturally occurring variants that affect the function of interest.

Inference engine 106 can also use structural information 128 (e.g., crystal structure, homology model of biopolymer, de novo modeled biopolymer, etc.) stored in knowledge base 108. For example, inference engine 106 can assign higher probabilities that amino acid residues in a polypeptide that are close to the active site of an enzyme will affect enzyme activity and/or specificity than more distant residues. Similarly, proximity to an epitope, proximity to an area of structural conflict, proximity to a conserved sequence, proximity to a binding site, proximity to a cleft in the protein, proximity to a modification site, etc. can be calculated from structural information 128 and used to calculate the probability that a substitution will result in a functional biopolymer. To calculate the distance of a residue from a region of functional interest, physical distances obtained using a known crystal structure of the reference sequence can be used. Alternatively, molecular modeling approaches can be used. For example, the structure of the reference sequence can be predicted based on its homology to a known structure, and then used to calculate distances. Or the entire structure of the reference sequence can be predicted and distances then calculated from the predicted structure.

In some embodiments structural information 128 is energy minimized. For example, the behavior of a biopolymer can be modeled using molecular dynamic simulations. In a specific example, a crystal structure or a predicted structure can be subjected to molecular dynamic simulation in order to model the effect of various external conditions such as the presence of solvent, the effect of temperature and ionic strength, upon the determined or predicted structure.

In addition to the examples of elements of information that can be used as a part of a knowledge base 108 described above, other information that can contribute to a biopolymer knowledge base 108 that can then be used by inference engine 106 of an expert system 100 to calculate the probability that a substitution will possess a desired function include, but are not limited to, individual sequence analysis (including sequence complexity, sequence content and composition, internal base-pairing and secondary structure predictions) sequence comparisons (including structure-based sequence alignments, homology-based sequence alignments, phylogenetic comparisons based on multiple pairwise comparisons, phylogenetic comparisons based on principal component analysis of sequence alignments, Hidden Markov models), evolutionary molecular analysis, structural analysis (including those using X-ray crystallographic data, nuclear magnetic resonance studies, structure threading algorithms, molecular dynamic simulations, active site geometry, determination of surface, internal and active site residues), known or predicted data relating sequence or structure to functional mechanisms, chemical and biophysical properties of functional groups, known or predicted functional effects of changes (for example information derived from the Protein Mutant Resource database, from an evolutionary comparison of sequence and activity data or from a comparison of reactions or half-reactions catalyzed by the biopolymer with reactions or half-reactions catalyzed by other biopolymers or sets of biopolymers), substitution matrices derived from sequence comparisons, mutations that are known or that can be predicted to affect physical properties of proteins (including stability, thermostability, pH optima), known or predicted properties (including plasticity and tolerance to substitutions) of homologous or related biopolymers (including other members of structurally, mechanistically or functionally related superfamilies or suprafamilies of proteins or other biopolymers), known or predicted immunological effects and constraints for specific sequence residues or motifs, known or predicted sequence effects on in vivo or in vitro post-translational or post-transcriptional modifications, known or predicted effects of the functional environment (including other proteins, nucleic acids or other molecules contained within a cell; for example, knowing the gene sequences expressed within a cell may assist in selecting siRNA sequences), measured or predicted biochemical or biophysical properties (including crystallization), effects of sequences on the expression of nucleic acids or proteins (including known or predicted RNA splice sites, protein splice sites, promoter sequences, transcriptional enhancer sequences, transcription and translation terminator sequences, sequences that affect the stability of a protein or nucleic acid, codon usage tables, nucleic acid GC content). Sources of this information can include, without limitation, text mined from scientific literature, data mined from genomic sequences, expressed sequences, structural databases and in second and subsequent iterations of the process, case specific data from the first points of the sequence space mapped.

In some embodiments of the present invention, knowledge base 108 is optionally preprocessed for information by knowledge base editor 114. For example, knowledge base 108 can contain many protein or polynucleotide sequences. During preprocessing by knowledge base editor 114, such sequences can be, for example, (i) aligned and distributed on a phylogenetic tree, (ii) grouped by principal component analysis (PCA), (iii) grouped by nonlinear component analysis (NLCA) (iv) grouped by independent component analysis (ICA), used to create sequence profiles (see, for example Gribskov, 1987, Proc Natl Acad Sci USA 84, 4355), (v) used to create Hidden Markov models or (vi) used to calculate structures prior to interrogation by the user. PCA, NLCA, and ICA is described in, for example, Duda et al., *Pattern Classification*, Second Edition, John Wiley & Sons, Section 10.13, which is hereby incorporated by reference.

In one embodiment, the output from an expert system 100 will describe the various substitutions recommended by methods 130 based on assignment of scores, confidences, ranks, or probabilities (hereinafter "scores") using rules 120 in knowledge base 108. In preferred embodiments, these scores are cumulative. That is, every rule 120 used by a method 130 will assign a score to the substitution under consideration and these scores can be higher if more rules are satisfied.

In the example of a proline endopeptidase (GENBANK A38086) there are many homologs and structures of homologs available. A detailed evaluation of various substitutions using three different methods 130 identified substitution F416Y as favorable. The scores from the various methods 30 are (i) the scores derived from favororability based on natural occurring substitutions using the PAM100 matrix is 5.29 (rank 1), (ii) the scores based on substitution found in a homolog expressed in the evolutionary distance of the homologs from the reference is 0.25 (rank 2), (iii) scores from positional variability of the sequence expressed in number of different types of amino acids found in that location is 3 (rank 7).

For example, FIG. 5 shows a series of steps that can be executed by expert system 100 in order to identify substitutions that are likely to increase the ability of an antibody to bind to a specific target antigen. Five independent methods 130 are shown for assessing the suitability of a substitution: (i) substitutions from homologous sequences in frameworks and complementarity determining regions (CDR), (ii) substitutions from homologous structures, (iii) substitutions from substitution matrices, (iv) substitutions from principal component analysis (PCA) and (v) substitutions from binding pocket analysis. For each method 130, one or more rules (filters) 120 defined in knowledge base 108 are used. For example, method (ii), substitutions from homologous structures, uses two rules 120. The first rule 120 is an estimate of the mean root mean square deviation (RMSD) from the target structure for every five residue window of the homolog structure, and select framework sites that deviate from the target structure by more than three Å. The second rule 120 identifies amino acid substitutions that are found in homologous sequences and select framework sites that are within five A of the complementarity determining region. In FIG. 5 rules 120 are applied as filters: a substitution that satisfies one of the rules is considered to have passed through that filter and receives a score. For example, in FIG. 5, this score is 1. The rules 120 used (applied) by the four other methods 130 for assessing the suitability of substitutions shown in FIG. 5 are also applied as filters. The score for each method can then be combined, for example by summing them. All possible substitutions can then be ranked in order of their cumulative scores. Although there are many variants, in some embodiments of the present invention, a component of step 02 of FIG. 2 uses the following algorithm in order to identify suitable substitutions:

for each residue position j of the biopolymer identified in step 01
{
  for each possible substitution k of residue j
  {
  initialize $score_{jk}$;
  for each method m (method 130) in a suite of methods
    {
    initialize $score_m$
    for each filter n (rule 120) in method m
      {
      compute filter n based on substitution k at position j;
      $score_m = score_m + $ result of filter n;
      }
    $score_{jk} = score_{jk} + score_m$
    }
  }
}
rank all $scores_{jk}$ Those substitutions that have satisfied more of the rules will have been assigned higher cumulative scores ($score_m$), and those with the highest scores will be selected for incorporation into a set of biopolymer variants.

There are many variations of ways to combine scores produced by two or more rules 120. Variations are possible (i) in the methods of assigning scores, (ii) in the methods of combining scores, and (iii) in the methods of assigning different weights to scores produced by different rules 120. Rules 120 can also be combined on a case by case basis, using expert knowledge. These rules 120 can be stored in a knowledge base 108 and can be executed by inference engine 106 using user input acquired by questioning the user for requirements and knowledge via the user interface 104.

5.1.1 Variations in the Method of Assigning Scores

In preferred embodiments, each rule 120 produces a reproducible quantitative value that can be used as a measure of the suitability of a substitution. However, there are many different ways in which quantitative scores can be obtained, and these ways can differ between different rules 120. A rule 120 can be used to produce an absolute quantitative score. This absolute quantitative score can be used directly, or it can be used to create a rank order list or a filter. As an example consider rule 1b of FIG. 4. Rule 1b calculates the difference in free energy between a target biopolymer and a biopolymer containing a substitution. This value can then be used in several different ways to compare the favorability of different substitutions. For example, (i) the absolute value of the free energy difference (caused by the substitution) can be used, (ii) the free energy differences of all possible substitutions can be ranked in order of favorability, then a subset of substitutions that are predicted to be the most favorable can be selected and assigned a score, (iii) the score can be a single value assigned to all of the substitutions belonging to the subset of the most favorable, (iv) the score can be a measure of the rank order of the substitution, so that the most favorable substitutions receive a higher score than those that are calculated to be less favorable, (v) a rule can also be used to rank all possible substitutions in order of predicted favorability and then eliminate a subset of these substitutions that are predicted to be the least favorable. In option (v), substitutions that were eliminated would receive a score of zero.

A way in which the predicted free energy change of a substitution can be used as a rule to obtain quantitative measures of the favorability of a substitution has been described. An absolute quantitative value obtained by any method for favorability can also be transformed by use of a function. In the case of free energy change, instead of using the free energy change itself the exp(free energy change) or step functions that can reflect (iii) above can be used. One of skill in the art will appreciate that there are other rules that can be applied to assess the effect of a substitution in order to produce absolute quantitative scores and all such other rules are included within the scope of the present invention.

5.1.2 Variations in the Method of Combining Scores

The scores produced by individual rules can be combined in a variety of ways. In some embodiments they are added together in the manner illustrated in the algorithm illustrated in Section 5.1 above. In some embodiments, the scores are multiplied together. For example, for each residue position j of the biopolymer identified in step 01
{
  for each possible substitution k of residue j
  {
  initialize $score_{jk}$;
  for each method m (method 130) in a suite of methods
    {
    initialize $score_m$
    for each filter n (rule 120) in method m
      {
      compute filter n based on substitution k at position j;
      $score_m = score_m \times $ result of filter n;
      }
    $score_{jk} = score_{jk} + score_m$
    }
  }
}
rank all $scores_{jk}$ In some embodiments, one or more rules 120 can be used as a filter, so that only substitutions passing the one or more filter are used, regardless of their scores from the other rules. For example,

```
for each residue position j of the biopolymer identified in step 01
{
   for each possible substitution k of residue j
   {
   initialize score_jk;
   set abort false
   for each method m (method 130) in a suite of methods
   {
      initialize score_m
      for each filter n (rule 120) in method m
      {
         compute filter n based on substitution k at position j;
         if result of filter n is negative {
            set abort true
            break;
         }
         score_m=score_m+result of filter n;
      }
      if abort
      {
         set score_jk=0
         break;
      }
      else
      {
         score_jk=score_jk+score_m
      }
   }
}
rank all scores_jk
```

In some embodiments, a cumulative score can be produced by any mathematical function of the scores produced by two or more individual rules. For example,

```
for each residue position j of the biopolymer identified in step 01
{
   for each possible substitution k of residue j
   {
   initialize score_jk;
   for each method m (method 130) in a suite of methods
   {
      initialize score_m
      for each filter n (rule 120) in method m
      {
         compute filter n based on substitution k at position j;
         score_m=score_m+weight_n×(result of filter n);
      }
      score_jk=score_jk+score_m
   }
}
rank all scores_jk
```

In the exemplary algorithm above weight$_n$ is some rule 120 specific weight that is independently assigned to a rule. Such weights can be stored in knowledge base 108 and adjusted by an expert using knowledge-base editor 114 (FIG. 1).

In addition, prior to combination, scores produced by individual rules can be scaled or normalized to facilitate their combination. For example, in the case of proline endopeptidase discussed earlier, the mutation F416Y was identified as the most favorable substitution by combining the scores from three methods 130. The distance, expressed in fraction of amino acid differences, was transformed and a Poisson correction (−log [1−fraction]) applied and multiplied by the product of the absolute scores obtained from the other two methods 130. The resulting scores for all substitutions were ranked and F416Y (combination score 126) was ranked 1.

5.1.3 Variations in the Method of Assigning Weights to Scores from Different Rules As indicated in Section 5.1.2, the scores produced by individual rules 120 can be assigned different weights prior to being combined. For example, if the total score for a substituting monomer x at position i ($S_{ix}$) is obtained by adding the scores obtained by applying n different rules, the score can be expressed by Equations (1) or (2):

$$S_{ix}=W_1 i_x R_1+W_2 i_x R_2+W_3 i_x R_3+W_4 i_x R_4+W_5 i_x R_5++ W_n i_x R_n \quad \text{(Eq. 1)}$$

where,
$i_x R_n$ is the score given by rule n for substituting monomer x at position i; and
$W_n$ is a weight applied to the score given by rule n.

$$S_{ix}=f(W_1 R_1(i_x), W_2 R_2(i_x), W_j R_j(i_x)) \quad \text{(Eq. 2)}$$

where,
$R_j(i_x)$ is the score given by rule j for substituting monomer x at position i;
$W_j$ is a weight applied to scores given by rule j; and
f is some mathematical function Rules (and weights) can be (i) specific for a substitution of monomer x at a specific location, (ii) specific for position for any and/or a group of monomer substitution(s), (iii) specific for any and/or a group of positions for a specific monomer x, (iv) specific for any substitutions derived from a particular and/or a group of homologs, (v) or specific for any position derived from a particular and/or a group of homologs.

The use of weights to modify scores obtained using different rules has a number of benefits.

Firstly, the use of weights to modify scores obtained using different rules 120 allows different rules 120 to have different degrees of influence over the final score for a substitution. For example if Rule 4 is the most important in determining the suitability of a substitution in a particular biopolymer, then this rule can be made to dominate the total score for the substitutions by making $W_4$ much higher than the other weights.

Secondly, the use of weights to modify scores obtained using different rules 120 allows different rules 120 to have different degrees of influence over the final score for a substitution depending upon the class or subclass of biopolymers being considered. For example a rule 120 considering the structural effect of a substitution can be most important for engineering an antibody, while a rule 120 considering the statistical likelihood of a substitution using a substitution matrix can be most important for engineering a protease. In this case, by first determining to which class of biopolymer the target biopolymer belongs, expert system 100 can then be used to assign weights to the scores from different rules 120 that will result in the most accurate assessment of the favorability of substitutions. Moreover, as previously described, expert system 100 can assign different weights to different methods, to produce more control over how substitutions scores are computed.

Thirdly, the use of weights to modify scores obtained using different rules 120 allows expert system 100 to incorporate information obtained from previous experiments. For example, another aspect of the invention involves the use of sequence-activity relationships to empirically measure the contribution of substitutions to one or more activity of a biopolymer. This aspect of the invention is described more fully in Section 5.5. This sequence-activity determination effectively creates a feedback loop by which weights assigned to the scores from different rules 120 applied by expert system 100 can be adjusted. As an example, consider the case in which 20 substitutions within a biopolymer (represented by $S_1$-$S_{20}$) receive final combined scores $C_1$-$C_{20}$ from expert system 100. A set of biopolymers that contain these substitutions are synthesized, and a sequence-activity relationships derived using wet lab assays. The sequence-activity relationships are used to determine actual scores that measure the fitness of each substitution for the desired activity of the biopolymer ($F_1$-$F_{20}$). The weights applied to each rule 120 and/or method 130 can then be adjusted so that the observed fitness of each substitution, $F_1$-$F_{20}$, correlate more closely with scores $C_1$-$C_{20}$ produced by expert system 100. In some embodiments, this correlation is the correlation between the absolute values of the scores for each substitution from expert system and the observed fitness of each substitution derived from the sequence-activity relationship. In some embodiments, the correlation can be a correlation between the rank order of effect of substitutions predicted by expert system 100 and the rank order of substitutions observed or derived from the sequence-activity relationship. The weights applied to each rule 120 can also be adjusted so that the correlation between the observed fitness of substitutions and the scores produced by expert system 100 is maximized for more than one set of substitutions, in one or more different target biopolymers.

Different classes of biopolymers can optionally be used to provide different sets of substitutions for comparing observed fitness and scores produced by expert system 100. This allows different weights to be calculated to apply to the scores produced by different rules 120 as a function of biopolymer class. One skilled in the art will appreciate that there are many possible variations of using experimental results to adjust weights applied to rule 120 scores. All such variants, whose predictive scoring functions can be adjusted based upon experimental data, are within the scope of the expert systems 100 of the present invention and can thus be considered systems capable of learning.

Because of the capacity for expert systems 100 of the present invention to learn by, for example, adjustment of rule 120 weights, in some instances it can be desirable to select substitutions that are favored strongly by different rules 120. Such selection can facilitate the establishment of the appropriate weights to be applied to rules 120 used by expert system 100.

The score for a substitution based on two or more rules can be calculated independently or using conditional probabilities. An expert system 100 can produce scores for at least 2, 3, 4, 5, 6, 7, 8, 9, 10, 11, 12, 13, 14, 15, 16, 17, 18, 19, 20, 25, 30, 35, 40, 45, 50, 60, 70, 80, 90 or 100 positions in the reference sequence up to the entire sequence, and can include contiguous residues or noncontiguous residues or mixtures thereof. The expert system 100 can include at least 2, 3, 4, 5, 6, 7, 8, 9, 10, 11, 12, 13, 14, 15, 16, 17, 18, 19, 20, 25, 30, 35, 40, 45 or 50 different residues. Naturally occurring residues can be included in the expert system, as well as unnatural residues for synthetic methods, and combinations thereof.

In another embodiment of the invention, the above calculations can be performed by an expert with access to the relevant knowledge base 108, for example, by using user interface 104.

Examples of the ways in which such expert system 100 can be used to automatically select substitutions to make in a biopolymer (in this case a protein) will now be described in the following sections with reference to FIGS. 4 and 5. The following exemplary process is intended to illustrate one possible embodiment of the invention. One skilled in the art will recognize that there are many possible variations on this theme, and the following is not intended to limit the present invention. The selection process refers to the scheme shown in FIG. 4.

FIG. 4 shows a series of independent rules 120, each of which can be used to produce a score for any possible amino acid substitution in a protein. In one embodiment of the invention, all possible single substitutions can be enumerated computationally and then scored according to one or more of the rules executed by expert system 100.

5.1.4 Rules Based on Substitutions from Homologous Sequences

One source of information that can be used to construct rules 120 that assess the likely effect of amino acid substitutions upon one or more activities of a protein is the sequence of one or more homologous proteins. See, for example, FIG. 4, rule 3a. Homologous sequences are generally analogous functionally and structurally, although having been subjected separately to different selective pressures they are also likely to be optimized differently. Amino acids that differ between homologous sequences thus provide a guide to substitutions that are likely to yield functional though different proteins. Alignment of homologous sequences can therefore be used to identify candidate substitution positions thus:

In one approach, homologous protein sequences are aligned (e.g., by using clustalw; Thompson et al., 1994, Nucleic Acids Res 22: 4673-80) and then a phylogenetic tree is reconstructed. Conservation indices can then be calculated for each site (e.g., Dopazo, 1997, Comput Appl Biosci 13: 313-7) and the information content calculated for each site (e.g., Zhang, 2002, J Comput Biol 9: 487-503). These scores can be exhaustively calculated for every position in the protein. The scores reflect the extent of tolerance to substitutions in the protein at each position. The scores can be normalized using the phylogenetic tree to eliminate bias in the homolog sequences found in databases (for e.g. ease of access to certain template DNAs results in sequences from certain class of organisms dominates the database.) Scores for a given alignment can also be normalized to have an average value of 0.0 and a standard deviation of 1.0, or other standard procedures can be used to compare and combine scores from multiple methods. These values can then be used directly as a score, as outlined above and in Equation (1) or Equation (2). In some embodiments, all sites with a score above a certain threshold value can be selected. For example, a cutoff (threshold) of 0.0 can be chosen (which is set to be the average score). In still other embodiments, all sites with a score below a certain threshold value can be eliminated. In some embodiments, the most variable (e.g., least conserved) sites can be selected by ranking the sites in order of these scores. For example the most highly scoring site can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 most highly scoring sites can be selected. In some embodiments the least variable (e.g., most conserved) sites can be eliminated by ranking the sites in order of these scores. For example, the least highly scoring site can be eliminated, or the 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, 800, 900 or 1000 least highly scoring sites can be eliminated (FIG. 4, Rule 1a).

Amino acid diversity and tolerance at each site can be measured as a fitness property of each amino acid at every location. The most fit residue for that position carries a higher value (e.g., Koshi et al., 2001, Pac Symp Biocomput 191-202; O. Soyer, M. W. Dimmic, R. R. Neubig, and R. A. Goldstein; Pacific Symposium on Biocomputing 7:625-636 (2002). Sites can be grouped into site-classes or treated independently. Sites and site classes most fit to change based on the substitution rate and the substitutions most favorable based on the fitness can be selected (FIG. 4, Rule 2a). In some embodiments, these values of fitness can then be used directly as a score, as outlined above and in Equation (1) or Equation (2). In some embodiments all sites with a score above a certain threshold value can be selected. For example, a cutoff (threshold) of 0.0 can be chosen (when the normalization of scores sets the wild type residue found in the reference to be 0.0. In some embodiments, all sites with a score below a certain threshold value can be eliminated. Threshold values of 0.0 or below can be eliminated, thereby only including amino changes that have a higher fitness value that the reference wild type amino acid found in that position. In some embodiments, the sites most tolerant to change can be selected by ranking the sites in order of these scores. For example, the most highly scoring site can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 most highly scoring sites may be selected. In some embodiments, the sites least tolerant to change can be eliminated by ranking the sites in order of these scores. For example, the least highly scoring site can be eliminated, or the 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, 800, 900 or 1000 least highly scoring sites can be eliminated.

For example, in the study of G-protein coupled receptors (GPCR) by Soyer et. al. (O, Soyer, M. W. Dimmic, R. R. Neubig, and R. A. Goldstein; Pacific Symposium on Biocomputing 7:625-636 (2002)), using the 8-site class model the class #8 was identified to have the highest substitution rate and the property correlating with fitness of amino acids at these positions was identified to be "charge transfer" propensity of the amino acid. In the present invention, amino acids in the sites that carry a higher relative fitness compared to the wild type amino acid found in that position are identified as suitable for substitution. The scores for these residues will be higher and can be combined with other methods 130.

In some embodiments, evolutionary relationships between homologous sequences can be derived in the form of phylogenetic trees. Using evolutionary models, ancestral sequences can probabilistically reconstructed. See, for example, Koshi and Goldstein, 1996, Mol. Evol. 42, 313-320. Coupled with knowledge of functions of proteins, evolutionary analysis will also identify amino acid changes that occur in functionally distinct groups. See, for example, Zhang and Rosenberg, 2002, PNAS 99, 5486-5491. Comparison of the rates of synonymous ($K_s$) versus non-synonymous substitutions ($K_a$) can also be used to quantify (e.g., using $K_a/K_s$ ratio) the type and degree of evolutionary constraint on substitutions. See, for example, Benner et al., 2000, *Res Microbiol* 151, 97-106. Here, $K_a/K_s>1$ means adaptive evolution and $K_a/K_s<0.1$ is observed for purifying selection. Methods to detect positive selection at single amino sites in order to infer residues critical for adaptation to new functions can also be applied. See, for example, Suzuki and Gojobori, 1999, Mol. Biol. Evol. 16, 1315-1328. Together these analyses allow for the identification of functionally important conservations and changes, even those distant from an active site. See, for example, FIG. 4, rule 2c.

Consider the case in which the function of a protein is dependent on the fact that the identity of a residue at a particular position in the protein is not altered. In such instances, the codon for this residue in the gene for the protein will tend to encode the same amino acid throughout the phylogenetic tree (synonymous substitutions, high $K_s$). On the other hand, when the function of a protein is capable of tolerating different amino acids at a particular position, then alterations of the corresponding codon in the gene will more frequently encode different amino acids throughout the phylogenetic tree (non-synonymous substitutions, $K_a$ comparable with $K_s$). Thus, the ratio of frequency with which a site is replaced by a synonymous codon to the frequency with which it is replaced by a non-synonymous codon in a reconstructed phylogenetic tree provides a measure of the selective pressure (on the function of the protein) acting to conserve the identity of the amino acid at that position. Often these ratios are calculated as averages for entire sequences. However, such ratios can also be limited to specific sites or groups of positions. These ratios can also be used to weight substitutions identified by other methods from a specific homolog. These values can then be used directly as a score, as outlined above and in Equation (1) or Equation (2).

In alternative embodiments, all sites with a tolerance for change above a certain threshold value can be selected. The threshold value can be determined by the user or knowledge base 114. For example, for identifying changes that do affect the specific function of the protein, only the substitutions present in positions where the ratio Ka/Ks>0.5 along any or a particular branch of the tree are accepted (and/or substitutions from homologs under any branch of the tree whose average Ka/Ks<0.5 are identified and eliminated). In other embodiments, all sites with a tolerance for change below a certain threshold value can be eliminated. The threshold value can be determined by the user or knowledge base 114. For example, for identifying changes that do not affect the specific function of the protein, only the substitutions present in positions where the ratio Ka/Ka<0.5 are identified (and/or substitutions from homologs whose average K/Ks>0.5 are identified and eliminated). In still other embodiments, the sites at which changes that are most adaptive can be selected by ranking the sites in order of these scores. For example, the most highly scoring site can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 most highly scoring sites can be selected. In still other embodiments, the sites that have low Ka/Ks are important to retain function and therefore changes that have high Ka/Ks can be eliminated by ranking the sites in order of these scores. For example, the highly scoring site can be eliminated, or the 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, 800, 900 or 1000 highly scoring sites can be eliminated.

5.1.5 Rules Based on Substitutions from Homologous Structures

Another source of information that can be used to construct rules 120 that assess the likely effect of amino acid substitutions upon one or more activities of a protein is the structure that protein or the structures of one or more homologous proteins. See, for example, FIG. 4, Rule 3b. The structures of many proteins and their variants are also available in the RCSB protein data bank ((2002) *Acta Cryst. D* 58 (6:1), pp. 899-907); and Structural Bioinformatics (2003); P. E. Bourne and H. Weissig, Hoboken, N.J., John Wiley & Sons, Inc. pp. 181-198. The availability of structures can help identify amino acid changes that affect protein function. One way in which they can be used to do so is to avoid changes to the biopolymer of interest that will not be structurally tolerated by the biopolymer. Changes computed in-silico using energy functions and force fields correlate with experimentally measured free energy changes in the stabilities of proteins. See, for example, Privalov et al., 1988, Adv Protein Chem 39: 191-234; Lee, 1993, Protein Sci 2: 733-8; Freire, 2001, Methods Mol Biol 168: 37-68; and Guerois et al., 2002, J Mol Biol 320: 369-87). Therefore, candidate amino acid changes can modeled into the structure(s) computationally and changes in the free energy computed. These computationally calculated changes in free energies resulting from the substitutions can then be used directly as a score, as outlined above and in Equation (1) or Equation (2). Alternatively, all changes can be selected that increase the free energy of the protein by less than a certain value. For example, all changes that would increase the free energy by less than 1 kCal/mol can be selected, all changes that would increase the free energy by less than 1.5 kCal/mol can be selected, all changes that would increase the free energy by less than 2 kCal/mol can be selected, or all changes that would increase the free energy by less than 2.5 kCal/mol can be selected. In some embodiments, all changes can be eliminated that increase the free energy of the protein by more than a certain value. For example, all changes that would increase the free energy by more than 1 kCal/mol can be eliminated, all changes that would increase the free energy by more than 1.5 kCal/mol can be eliminated, all changes that would increase the free energy by more than 2 kCal/mol can be eliminated, all changes that would increase the free energy by more than 2.5 kCal/mol can be eliminated. In some embodiments, the best tolerated substitutions can be selected by ranking the sites in order of the predicted increase in free energy. For example, the substitution with the lowest increase in free energy can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 substitution with the lowest increase in free energy may be selected. In some embodiments, the substitutions with the greatest increases in free energy can be eliminated by ranking the sites in order of these scores. For example, the 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, 800, 900, 1000, 2000, 3000, 4000, 5000, 6000, 7000, 8000, 9000, 10000, 12000, 14000, 16000, 18000 or 20000 substitutions with the greatest increases in free energy can be eliminated (FIG. 4, Rule 1*b*).

In alternative embodiments, multiple changes can be modeled into the structure(s) computationally and changes in the free energies resulting from the substitutions computed. These free energy values can be used to identify changes that are "valid" independently, but not together. Amino acid changes that are independent can be selected preferentially. Amino acid clashes that yield a higher free energy when compared to the free energies produced by modeling changes separately can be eliminated.

Regions of the protein that differ structurally between homologs are more likely to tolerate change, while those regions that are structurally conserved are likely to be less tolerant. Structures can be directly obtained from the database or predicted using various structure modeling software packages. Structures of homologs and mutants can be superposed on the wild type structure. See, for example, May et al., 1994, Protein Eng 7: 475-85; and Ochagavia et al., 2002, Bioinformatics 18: 637-40). Structural conservation can be calculated as the root mean squared (RMS) deviations of the backbones of the superposed chains. This can be computed as the deviations of individual residues, or more preferably as the deviations of a running average over a between two and ten residue stretch of the backbone between the target protein and one or more homologous proteins. These computationally calculated RMS deviations for every position between homologous structures can then be used directly as a score, as outlined above and in Equation (1) or Equation (2). In some embodiments, RMS deviations between the alpha carbons (or backbone atoms) in the structure of the target protein and one or more homologous proteins that are greater than a threshold value can be considered structurally labile and these sites can be selected. This threshold RMS deviation between homologous structures can be greater than 2 Å, 2.5 Å, 3 Å, 3.5 Å, 4 Å, 4.5 Å, 5 Å.

In some embodiments, RMS deviations between the alpha carbons in the structure of the target protein and one or more homologous proteins that are less than a threshold value can be considered structurally conserved and these sites can be eliminated. This threshold RMS deviation between homologous structures can be less than 2 Å, 2.5 Å, 3 Å, 3.5 Å, 4 Å, 4.5 Å, or 5 Å.

In some embodiments sites can be ranked in order of the calculated RMS deviations between the alpha carbons in the structure of the target protein and one or more homologous proteins and those with the highest calculated RMS deviations selected. For example, the site with the highest calculated RMS deviations between homologous structure can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 sites with the highest calculated RMS deviations between homologous structure may be selected.

In some embodiments, sites can be ranked in order of the calculated RMS deviations between the alpha carbons in the structure of the target protein and one or more homologous proteins and those with the lowest calculated RMS deviations eliminated. For example, the site with the lowest calculated RMS deviations between homologous structures can be eliminated or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 sites with the lowest calculated RMS deviations between homologous structure can be eliminated (FIG. 4, Rule 2*b*).

Changes near catalytic and binding sites are highly likely to influence the activity of the protein and are good candidates for substitution. All amino acid substitutions that are found in one or more homologs can be tested for proximity to a binding or catalytic or regulatory site of the protein. In some embodiments, the distance between an amino acid substitution that is found in one or more homologs from a binding or catalytic or regulatory site can be used directly as a score, as outlined above and in Equation (1) or Equation (2). Alternatively, in some embodiments, all amino acid substitutions that are found in one or more homologs and that are within a threshold distance of a binding or catalytic or regulatory site in the protein can be selected. This threshold distance can be less than 2 Å, 2.5 Å, 3 Å, 3.5 Å, 4 Å, 4.5 Å, 5 Å, 5.5 Å, 6 Å, 6.5 Å, 7 Å. In still other embodiments, all amino acid substitutions that are found in one or more homologs and that are beyond a threshold distance of a binding or catalytic or regulatory site in the protein can be eliminated. This threshold distance can be more than 2 Å, 2.5 Å, 3 Å, 3.5 Å, 4 Å, 4.5 Å, 5 Å, 5.5 Å, 6 Å, 6.5 Å, or 7 Å. In still other alternative embodiments, all amino acid substitutions that are found in one or more homologs can be ranked in order of proximity to a binding or catalytic or regulatory site in the protein and those that are closest to the binding or catalytic or regulatory site selected by a rule 120. For example, the substitution closest to the binding or catalytic or regulatory site can be selected, or between 2 and 20, between 10 and 100, or the top 200 substitutions closest to the binding or catalytic or regulatory site can be selected. In still other alternative embodiments, all amino acid substitutions that are found in one or more homologs can be ranked in order of proximity to a binding or catalytic or regulatory site in the protein and those that are farthest from the binding or catalytic or regulatory site eliminated. For example, the substitution farthest from the binding or catalytic or regulatory site can be eliminated. In some embodiments, between 2 and 20, between 10 and 100, or the top 200 substitutions farthest from the binding or catalytic or regulatory site can be eliminated.

5.1.6 Rules Based on Substitutions from Substitution Matrices

Another source of information that can be used to construct rules 120 that assess the likely effect of amino acid substitutions upon one or more activities of a protein is the frequency with which one amino acid is observed to substitute for another amino acid in different proteins. The matrix can be expressed in terms of probabilities or values derived from probabilities by mathematical transformation involving probabilities of transitions or substitutions (Pij) and observed frequencies of amino acids (Fi). Matrices using such transformation include scoring matrices like PAM100, PAM250, and BLOSUUM etc. See, for example, FIG. 4, rule 1c. Substitution matrices are derived from pairwise alignments of protein homologs from sequence databases. They constitute estimates of the probability that one amino acid will be changed to another while conserving function. Different substitution matrices are calculated from different sets of sequences. For example, they can be based on the structural environment of a residue (Overington, 1992, Genet Eng (NY) 14: 231-49.; and Overington et al., 1992, Protein Sci 1: 216-26.) or on additional factors including secondary structure, solvent accessibility, and residue chemistry (Luthy et al., 1992, Nature 356: 83-5.

A substitution matrix that best captures the observed sequences in the protein family of interest can be calculated using the Bayesian method developed by Goldstein et al. (Koshi et al., 1995, Protein Eng 8: 641-645) and used to score all candidate substitutions.

In some embodiments these values can then be used directly as a score, as outlined above and in Equation (1) or Equation (2). The scores can expressed as Pij: the probability of substituting residue i with j. Any transformations of Pij can also be used. Pij can be computed for a specified evolutionary distance. In alternative embodiments, all substitutions with a probability above a certain threshold value may be selected. Threshold values of 0.00001, 0.00001, 0.0001, 0.01 or 0.1 can be used for probabilities and/or threshold values of −5, −4, −3, −2, −1, 0, 1, 2, 3, 4 or 5 for any PAM matrix. In still other embodiments, all substitutions with a probability below a certain threshold value may be eliminated. Threshold values of 0.00001, 0.00001, 0.0001, 0.01 or 0.1 can be used for probabilities and/or threshold values of −5, −4, −3, −2, −1, 0, 1, 2, 3, 4, or 5 for any PAM matrix. In still other embodiments, the most favorable substitutions can be selected by ranking substitutions in order of their substitution matrix probability scores. For example, the most highly scoring substitution can be selected, or the top 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, up to 50, up to 60, up to 70, up to 80, up to 90, up to 100, up to 110, up to 120, up to 130, up to 140, up to 150, up to 160, up to 170, up to 180, up to 190, up to 200, up to 210, up to 220, up to 230, up to 240, up to 250, up to 260, up to 270, up to 280, up to 290, up to 300, up to 310, up to 320, up to 330, up to 340, up to 350, up to 360, up to 370, up to 380, up to 390, up to 400, up to 500, up to 600, up to 700, up to 800, up to 900, up to 1000, up to 2000, up to 3000, up to 4000, up to 5000, up to 6000, up to 7000, up to 8000, up to 9000, up to 10000, up to 12000, up to 14000, up to 16000, up to 18000 or up to 20000 most highly scoring substitutions can be selected. In still other embodiments, the least favorable substitutions can be eliminated by ranking substitutions in order of their substitution matrix probability scores. For example, the least substitution with the lowest substitution matrix probability may be eliminated, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, up to 50, up to 60, up to 70, up to 80, up to 90, up to 100, up to 110, up to 120, up to 130, up to 140, up to 150, up to 160, up to 170, up to 180, up to 190, up to 200, up to 210, up to 220, up to 230, up to 240, up to 250, up to 260, up to 270, up to 280, up to 290, up to 300, up to 310, up to 320, up to 330, up to 340, up to 350, up to 360, up to 370, up to 380, up to 390, up to 400, up to 500, up to 600, up to 700, up to 800, up to 900, up to 1000, up to 2000, up to 3000, up to 4000, up to 5000, up to 6000, up to 7000, up to 8000, up to 9000, up to 10000, up to 12000, up to 14000, up to 16000, up to 18000 or up to 20000 substitutions with the lowest substitution matrix probability can be eliminated.

A substitution or a scoring matrix can be calculated by considering homologous proteins from many different protein families (e.g., Benner et al., 1994, Protein Eng 7: 1323-1332; and Tomii et al., 1996, Protein Eng 9: 27-36) can be used to score all candidate substitutions. Matrices derived from a variety of protein are often used to evaluate and confirm homology of protein sequences and represent an approximation of protein evolution in general. In some embodiments, these values can then be used directly as a score, as outlined above and in Equation (1) or Equation (2). In some embodiments, all substitutions with a probability above a certain threshold value can be selected. Threshold values of 0.00001, 0.00001, 0.0001, 0.01 or 0.1 can be used for probabilities and/or threshold values of −5, −4, −3, −2, −1, 0, 1, 2, 3, 4, 5 for any PAM matrix can be used. In still other embodiments, all substitutions with a probability below a certain threshold value can be eliminated. Threshold values of 0.00001, 0.00001, 0.0001, 0.01 or 0.1 can be used for probabilities and/or threshold values of −5, −4, −3, −2, −1, 0, 1, 2, 3, 4, 5 can be used for any PAM matrix. In still other embodiments, the most favorable substitutions can be selected by ranking substitutions in order of their substitution matrix probability scores. For example the most highly scoring substitution may be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, up to 50, up to 60, up to 70, up to 80, up to 90, up to 100, up to 110, up to 120, up to 130, up to 140, up to 150, up to 160, up to 170, up to 180, up to 190, up to 200, up to 210, up to 220, up to 230, up to 240, up to 250, up to 260, up to 270, up to 280, up to 290, up to 300, up to 310, up to 320, up to 330, up to 340, up to 350, up to 360, up to 370, up to 380, up to 390, up to 400, up to 500, up to 600, up to 700, up to 800, up to 900, up to 1000, up to 2000, up to 3000, up to 4000, up to 5000, up to 6000, up to 7000, up to 8000, up to 9000, up to 10000, up to 12000, up to 14000, up to 16000, up to 18000 or up to 20000 most highly scoring substitutions can be selected. In still other embodiments, the least favorable substitutions can be eliminated by ranking substitutions in order of their substitution matrix probability scores. For example, the least substitution with the lowest substitution matrix probability may be eliminated, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, up to 50, up to 60, up to 70, up to 80, up to 90, up to 100, up to 110, up to 120, up to 130, up to 140, up to 150, up to 160, up to 170, up to 180, up to 190, up to 200, up to 210, up to 220, up to 230, up to 240, up to 250, up to 260, up to 270, up to 280, up to 290, up to 300, up to 310, up to 320, up to 330, up to 340, up to 350, up to 360, up to 370, up to 380, up to 390, up to 400, up to 500, up to 600, up to 700, up to 800, up to 900, up to 1000, up to 2000, up to 3000, up to 4000, up to 5000, up to 6000, up to 7000, up to 8000, up to 9000, up to 10000, up to 12000, up to 14000, up to 16000, up to 18000 or up to 20000 substitutions with the lowest substitution matrix probability can be eliminated.

In the example of a proline endopeptidase (GENBANK A38086) there are many homologs and structures of homologs available. Every possible substitution enumerated was assigned a score based on the PAM100 matrix. For example, substitutions for position 416: F416Y ranks number 1 and has a score of 5.24, F416L ranks 565 with a score of 1.2 and F416I ranks 1765 with a score of −0.83.

5.1.7 Rules Based on Substitutions from Principal Component Analysis of Sequence Alignments Protein sequences can be mathematically represented in terms many variables, each variable representing the type of amino acid at a specific location. For example the sequence AGWRY can be represented by 5 variables, where variable 1 assumes a value of "A" corresponding to position 1, variable 2 is "G" corresponding to position 2 and so on. Each variable can assume 1 of 20 possibilities. Alternatively each variable can also represent multiple positions (say 2) and assume 1 of 400 values (for 2 positions) corresponding to 20×20=400 combination of possible amino acid pairs. Alternatively, each position can assume a value corresponding to a physico-chemical property of the amino acid instead of amino acid identity. Alternatively, each variable can be a combination of variables representing properties of amino acids. Alternatively, each variable can be represented in a binary form corresponding to presence or absence of a particular amino acid. Alternatively, each variable can be represented in a binary form corresponding to presence or absence of a defined group of amino acids.

Typical proteins contain many hundred variables. A set of proteins are various points in the variables space and relationship between various proteins can be represented in terms of the values of the variables corresponding to those proteins. In such a high-dimension space (due to high degree of variables) proteins can be clustered and classified using statistical techniques like the principal components analysis, k-means clustering, SVM etc.

Using such methods, particularly but not limiting to Principal Component Analysis (PCA), we can classify sequences and identify residues that differentiate various related protein sequences and their functions. Typical protein sequence alignments contain many amino acid positions at which differences occur, leading to a high number of dimensions required to represent the sequence space. A sequence alignment can be subjected to principal component analysis to identify new composite dimensions that describe and visualize a significant fraction of the variation between a set of sequences. The new dimensions (the principal components) can also be described in terms of the contributions of each monomer variation within the original sequence alignment to that dimension (the "loads"). Typically a single principal component contains contributions from tens or hundreds of different monomer differences within a set of biopolymer sequences. One powerful application of principal component analysis is that it can be used to suggest a relationship between biopolymer sequence and function. Biopolymer sequence can be represented in terms of the principal components of that sequence. Principal components can then be identified in which biopolymers are grouped functionally. The loads of those principal components can then be used to identify the monomers that are most responsible for the grouping of the biopolymers within sequence space. These monomers are thus good candidates for substitutions likely to affect function.

Thus for proteins, amino acid substitutions that are most important in differentiating and grouping sequences are often also those that functionally differentiate the proteins. Identification of such amino acids using dimension-reducing techniques such as principal component analysis has been described (e.g., Casari et al., 1995, *Nat Struct Biol* 2: 171-178; Gogos et al., 2000, *Proteins* 40: 98-105; and del Sol Mesa et al., 2003, J Mol Biol 326: 1289-1302). PCA can identify sequence features and substitutions corresponding to the desired phenotype of the protein and scores "loads" for these features in the direction of desired phenotype are used as absolute scores or as filters to identify substitutions.

An example of the use of principal component analysis for identification of favorable substitutions is also shown in FIGS. 10-14. FIG. 10 shows the 49 proteases whose sequences are homologous to proteinase K. A property of interest in this example is activity during or after exposure of the protein to heat. The 49 sequences were subjected to principal component analysis, and the distribution of the sequences in the first two principal components is shown in FIG. 11. Proteases 46, 47, 48 and 49 were all obtained from thermostable organisms and can thus be expected to possess desirable thermostability properties. As shown in FIG. 11, these four proteases are grouped together in the first two principal components of the sequence space, characterized by strongly negative scores in both principal components 1 and 2. FIG. 12 shows the contributions (the "loads") of all amino acid differences within the alignment of the 49 proteases, to the new dimensions principal components 1 and 2. FIG. 13 shows an expanded detail of the lower left corner of FIG. 12 in which the identities of each amino acid contributing to the principal components are now shown. These amino acids are those most responsible for giving a protein sequence a strong negative score in principal component 1 and principal component 2. These contributions are quantitated in FIG. 14. Because these scores are also those seen for proteases from thermophilic organisms, the amino acids that are primarily responsible for conferring these scores upon proteins are very good candidates for amino acids that may confer desirable properties, in this case thermostability.

Any sequence principal component can be used that contributes to differentiating between two sets of biopolymers and that is likely to reflect some functional differences of interest. In some embodiments, the "load" contributed by a substitution to one or more such principal component of sequence can be used directly as a score, as outlined above and in Equation (1) or Equation (2). These scores assume a range of values and a distribution profile can be calculated. In some embodiments, all substitutions with a "load" above a certain threshold value for one or more principal components can be selected. Threshold values can be determined from the distribution profile and can be set to value based on the distribution of scores. For example, the threshold value can be set such that top 10% of the loads in a particular principal component are above the threshold. In some embodiments, all substitutions with a "load" below a certain threshold value can be eliminated. For example, the threshold value can be set such that bottom 10% of the loads in a particular principal component are below the threshold. In still other embodiments, the substitutions with the highest loads can be selected by ranking substitutions in order of their loads. For example, the substitution with the highest "load" can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 substitutions with the highest "loads" can be selected. In still other embodiments, the substitutions with the lowest loads can be eliminated by ranking substitutions in order of their loads. For example, the substitution with the lowest "load" can be eliminated, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, up to 50, up to 60, up to 70, up to 80, up to 90, up to 100, up to 110, up to 120, up to 130, up to 140, up to 150, up to 160, up to 170, up to 180, up to 190, up to 200, up to 210, up to 220, up to 230, up to 240, up to 250, up to 260, up to 270, up to 280, up to 290, up to 300, up to 310, up to 320, up to 330, up to 340, up to 350, up to 360, up to 370, up to 380, up to 390, up to 400, up to 500, up to 600, up to 700, up to 800, up to 900, up to 1000, up to 2000, up to 3000, up to 4000, up to 5000, up to 6000, up to 7000, up to 8000, up to 9000, up to 10000, up to 12000, up to 14000, up to 16000, up to 18000 or up to 20000 substitutions with the lowest "loads" may be eliminated.

5.1.8 Other Exemplary Rules Based Upon Principal Component Analysis of Sequence Alignments All of the scores obtained as described in subsections 5.1.4 through 5.1.7 are just examples of ways in which such values can be calculated. These values can then be combined in one of the ways described in Section 5.1. One skilled in the art will readily appreciate that there are many variations on methods for obtaining quantitative measures of the predicted fitness of a substitution in a biopolymer in such a way that these values may subsequently be combined. All such variations are included as aspects of the invention.

By combining the scores obtained from the rules used in methods 132 of expert system 100, a set of substitutions can be identified for testing. These may be the substitutions with the highest aggregate scores, they may be the substitutions with the highest score for each individual rule 120, or they may be derived in some other way using the scores produced by the rules 120 used by methods 130 of expert system 100. In some embodiments, the number of substitutions selected by step 03 of FIG. 2 in one cycle of the optimization process is less than 1000 substitutions, more preferably less than 250 substitutions, more preferably less than 100 substitutions and more preferably less than 50 substitutions.

5.2 Design of a Biopolymer Variant Set

The rules discussed in Section 5.1 above and shown in FIG. 4 are one example of the way in which an initial sequence space can be defined. The sequence space is defined in terms of an initial target biopolymer sequence, and substitutions to be made in that target sequence. Each substitution is defined in terms of a position in the target biopolymer, and the identity of a monomer with which the monomer at that position in the target biopolymer is to be replaced. Selection of the target biopolymer corresponds to step 01 in FIG. 2. Definition of the sequence space corresponds to step 02 in FIG. 2. This section is directed to step 03 of FIG. 2.

Once an initial set of substitutions has been selected in accordance with Section 5.1, a set of variants incorporating these changes can be designed (the designed biopolymer variant set). This process corresponds to step 03 in FIG. 2. In preferred embodiments, this designed biopolymer variant set includes only a subset of the total number of possible variants that could be generated. For example, the total number of possible variant proteins in a sequence space defined by a target protein containing all possible combinations of 24 substitutions is $2^{24}>16,000,000$. However the methods of the present invention allow the interrogation of this sequence space by designing and synthesizing only a very small fraction of the total number of biopolymers that are included in the sequence space defined by the initial target biopolymer and the substitutions. In some embodiments, the number of variants in the designed biopolymer variant set is less than 1000 variants, more preferably less than 250 variants and more preferably less than 100 variants. This is possible because, although the designed biopolymer variant set includes only a subset of the total number of possible variants (e.g. the possible combinations of substitutions), care is taken to test all biopolymer substitutions in many different sequence contexts. An example is shown in FIG. 16, where a set of 24 variants were designed to interrogate the sequence space defined by a target protein sequence and 24 substitutions illustrated in FIG. 15. Here, each variant contains six substitutions, each substitution occurs six times within the designed biopolymer variant set, and each occurrence of each substitution takes place within a quite different context, that is it is combined with a different set of other substitutions each time.

The aim when designing a set of biopolymer variants to interrogate a sequence space defined by a target biopolymer sequence and a set of substitutions is to obtain a designed biopolymer variant set where the substitutions are distributed in such a way that a large amount of information can subsequently be extracted from sequence-activity relationships. In this respect the design of biopolymer variant sets has common elements with the design of experimental datasets from a diverse range of other disciplines including agriculture and engineering. Methods to optimize experimental datasets (experimental design or design of experiment: DOE) are described by Sir R. A. Fisher in 1920 (Fisher, The Design of Experiments, MacMillan Publishing Company; 9th edition, 1971). Plackett and Burman developed the idea further with the introduction of screening designs (e.g., Plackett et al., 1946, Biometrika 33: 305-325), and Taguchi subsequently introduced the orthogonal matrix (Taguchi, 1986, *Introduction to Quality Engineering*, Asian Productivity Organization, Distributed by American Supplier Institute Inc., Dearborn, Mich.). An example of the application of a Taguchi orthogonal matrix to the design of eight variants that capture all pairwise combinations of seven amino acid substitutions is shown in FIG. 25. Any number of experimental design techniques can be used to maximize the information content of the designed biopolymer variant set including, but not limited to, complete factorial design, $2^k$ factorial design, $2^k$ fractional factorial design, central composite, latin squares, greco-latin squares, Plackett-Burmann designs, Taguchi design, and combinations thereof. See, for example, Box et al., 1978, *Statistics for Experimenters*. New York, Wiley, for examples of such techniques that can be used to construct a designed biopolymer variant set from the initial set of biopolymer substitutions selected in accordance with Section 5.1 that tests a maximum number of combinations in a minimal number of biopolymer variants.

The methods described above were designed to maximize the amount of information that could be obtained from a specified limited number of experiments that could be performed. This is conceptually comparable to the resource limitation seen in biopolymer optimization, where functional tests are complex and time, cost or other resource-limited. However, a significant difference between biopolymer optimization and other applications of experimental design is that for biopolymer optimization there is an additional constraint. In designing biopolymer variants, the simultaneous introduction of many changes can adversely affect functional properties of the biopolymer. In contrast to traditional experimental design strategies, it is advantageous in the present invention to reduce the number of previously untested substitutions present in each variant to ten or less, preferably to five or less, more preferably to between 3 and 10. For instance, in some specific embodiments, the number of previously untested substitutions present in each variant is 10, 9, 8, 7, 6, 5, 4 or 3. In other words, in subsequent cycles of steps 01 through 07 of FIG. 2, less than 10, 9, 8, 7, 6, 5, 4 or 3 new variants are chosen. Here, a variant references to a biopolymer that has a sequence that is identical to the sequence of the biopolymer selected in step 01 of FIG. 2 with the exception that there are one or more substitutions in the sequence. Here, a substitution refers to a mutation at a particular position in the biopolymer from the residue found at that position in the biopolymer selected in step 01 of FIG. 2 to some other residue.

To design a biopolymer variant set that will yield useful sequence-activity information upon analysis of the functional properties and sequences of the biopolymer variants, any method can be appropriate provided that the number of substitutions in each variant set is relatively small so that the majority of biopolymers are active. For instance, in preferred embodiments, the number of previously untested substitutions present in each variant is preferably 9, 8, 7, 6, 5, 4, 3 or 2. Furthermore, it is desirable that each selected substitution be tried an approximately equal number of times in the designed biopolymer variant set. It is further desirable that each substitution be tested in many different sequence contexts. In other words each substitution appears in a number of different biopolymer variants, in each case being combined with a different set of other substitutions. For example, in FIG. 16, the substitution L180I appears in variant 3 with P97S, E138A, Y194S, A236V, V267I and in variant 18 with N95C, S107D, V167I, G293A, I310K.

A variation of the above method is to require (i) that each substitution identified be tried an approximately equal number of times in the designed biopolymer variant set, and (ii) that as many different combinations of two substitutions (e.g. substitution pairs) as possible be tested. For example, to test forty substitutions in a biopolymer it may be desirable to incorporate a maximum of five changes per variant. For forty substitutions there are (40×39/2) 780 possible pairs of substitutions. In one variant with five substitutions there are ten pairs of substitutions. So in forty variants there will be a maximum of 400 substitution pairs. The aim is then to maximize the number of different substitution pairs that are tested and to try to represent each substitution five times. The substitution pairs can be scored with the initial selection algorithm, and the top scoring 400 substitution pairs tested. The solution to such a problem of finding variants with the constraints mentioned here is known as a coverage problem. The coverage problem is NP-hard. Therefore greedy and other forms of approximate solutions are used to solve the NP-hard problems in the present invention. For instance, in some embodiments, the algorithms described in Gandhi et al., 2001, Lecture Notes in Computer Science 2076: 225 are used.

As in example, in some embodiments, the desired set of sequences can be evolved using monte carlo algorithms and genetic algorithms to maximize the number of pairs in the variant set. Genetic algorithms are described in Section 7.5.1 of Duda et al., 2001, *Pattern Classification*, Second Edition, John Wiley & Sons, Inc., New York, which is hereby incorporated by reference. Further, similar algorithms can be used to expand the coverage problem to maximize the number of triplets, quadruplets and so on.

An exemplary code for maximizing the substitution pairs using an evolutionary coverage algorithm is shown below:

Let m be the number of identified substitutions, n be the number of variants to be synthesized, and k be the number of substitutions per variant.

Create n initial variants with k substitutions, each occurring n×k/m times among variants. This can be done randomly or sequentially. This set is not optimal. Then, for 10000 iterations
{
  i. Choose two random variants;
  ii. Choose two random positions;
  iii. Count the number of distinct substitution pairs seen among variants;
  iv. Swap the substitutions (if any) at the two positions between the two chosen variants;
  v. Check if the number of substitutions per variant is k;
  vi. Check if number of times a given substitution occurs among all variants equals n×k/m;
  vii. Count the number of distinct substitution pairs seen among variants;
  viii. If the count from vii) is greater than count from iii) and v) and vi) are true, accept the changes to the variants from step iv), else, dismiss the changes and retain original values.
}

Alternatively, the set of substitutions can be divided into two or more groups. Such groups can be used to design variants in which each variant contains substitutions from a particular group. The substitutions in such variants can be subjected to the coverage algorithms using the constraints described above. Each group can also be combined with other groups of substitutions in order to design initial variants. Then a coverage algorithm can be applied to combinations of substitution groups. Groups of substitutions can be arrived at using knowledge of protein domain and/or functional and structural properties of amino acid residues in the protein. For example, in a multi-domain protein, all substitutions based on the techniques described in Section 5.1 can be identified, top scoring variants can be selected, and such top scoring variants can then be classified into groups of substitutions based on which domain of the protein the substitutions are presented. Alternatively, substitutions can be classified based on their location in the protein structure (e.g surface position versus interior positions). Substitution locations can be determined using experimentally determined structures or structure prediction algorithms. Alternatively, substitutions can be classified based on their proximity to the active sites (e.g residues <5 Å from active site belong to one class and residues >5 Å from active site to another). Constraints on the number of substitutions from each substitution group can be imposed on the variant set. For example, two substitutions from the group close to the active site and three substitutions from the group representing the surface of the protein can be chosen.

The methods described above differ from typical experimental design or design of experiment (DOE) methods in the fact that no more than a predetermined number of changes in a variant (e.g., 5) is allowed and the occurrence of the selected pairs is maximized by scoring. Other DOE methods for distributing 40 substitutions would require as many as between 18 and 22 changes in a biopolymer, which would have a high likelihood of being detrimental to biopolymer function.

Alternatively or additionally, a biopolymer variant set can be created stochastically by library synthesis methods such as parallel site-directed mutagenesis, DNA shuffling or other methods for incorporating defined substitutions into a biopolymer such as those described in Section 5.8. In these instances the variant set contains substitutions distributed at random, so precisely defined variants are not synthesized. Instead, the introduction of substitutions is controlled so that the average number of substitutions incorporated into each variant is between 1 and 10, more preferably the average number of substitutions incorporated into each variant is between 1 and 5. Variants can then be selected at random and the distribution of substitutions can be determined by determining the sequence of the biopolymer. In some embodiments of the invention less than 1000 variants created by library synthesis methods are synthesized and sequenced, preferably less than 500 variants created by library synthesis methods are synthesized and sequenced, more preferably less than 250 variants created by library synthesis methods are synthesized and sequenced, even more preferably less than 100 variants created by library synthesis methods are synthesized and sequenced. In some embodiments that use libraries, the creation of a library can be simulated using computational modeling of shuffling and other methods. See, for example, Moore, 2001, Proc Natl Acad Sci USA 13, 3226-3231; Moore and Maranas, 2000, J Theor Biol. 205, pp. 483-503.

Once the biopolymer variant set has been designed, the variants are synthesized using methods known in the art. Representative, but nonlimiting synthetic methods are described in Section 5.8, below. Then the biopolymers are tested for relevant biological properties. Such relevant biological properties include, but are not limited to biopolymer solubility and activity. Nonlimiting examples of how such biopolymer activity can be tested are described in Section 5.9 below. Together the synthesis and testing of the biopolymer variants represent step 04 in FIG. 2.

5.3 Methods for Mapping a Sequence Space to a Function Space

Once substitutions have been selected using expert system 100 (FIG. 2, step 04), and variants have been designed, synthesized and tested for one or more activity or function, it is desirable to use the sequence and activity information from the designed biopolymer variant set to assess the contributions of substitutions to the one or more biopolymer activity or function. This process is represented as step 05 in FIG. 2.

Assessment of the contributions of substitutions to one or more biopolymer function can be performed by deriving a sequence-activity relationship. Such a relationship can be expressed very generally, for example as shown in Equation 3

$$Y=f(x_1,x_2,x_i) \quad (Eq\ 3)$$

where,

Y is a quantitative measure of a property of the biopolymer (e.g., activity), $x_i$ is a descriptor of a substitution, a combination of substitutions, or a component of one or more substitutions in the sequence of the biopolymer, and f( ) is a mathematical function that can take several forms. A model of the sequence-activity relationship can be described as a functional form whose parameters have been trained for the input data (Y and $x_i$). Protein sequences can be mathematically represented in terms of many variables (descriptors, predictors), each variable representing the type of amino acid at a specific location (linear form in terms of the position of the amino acid). For example, the sequence AGWRY can be represented by five variables, where variable one assumes a value of "A" corresponding to position 1, variable two is "G" corresponding to position two and so on. Each variable can assume 1 of 20 possibilities. Alternatively, each variable can also represent multiple positions (say two) and assume 1 of 400 values (for 2 positions) corresponding to 20×20=400 combination of possible amino acid pairs. For example, a variable can describe position one and two and assume a value of "AG" (thereby creating a variable that in non-linear in terms of position of the amino acid). Alternatively, each position can assume a value corresponding to a physico-chemical property of the amino acid instead of amino acid identity. For example, the position can be described in terms of the mass of the amino acid at that location. For the sequence AGWRY, a variable for position one can assume the value 71.09 and position two 57.052 and so on. Alternatively, each position can be described by one or several principal components derived to represent many physico-chemical properties of the amino acid present in that position. Alternatively, each variable can be a combination of variables representing properties of amino acids. Alternatively, each variable can be represented in a binary form corresponding to presence or absence of a particular amino acid. For example, consider two variants AGWRY and AKWRY, Position two can be "1 if G is present at that position and "0 if it is absent and the descriptor for that position can have the value "0 or "1." Alternatively, each variable can be represented in a binary form corresponding to presence or absence of a defined group of amino acids.

In equation 3, the functional form f( ) correlates descriptors of a protein sequence ($x_i$) to its activity. In a simple embodiment of the invention, the function f can be a linear combination of $x_i$:

$$Y=w_1x_1+w_2x_2,+w_ix_i \quad (Eq.\ 5)$$

where $w_i$ is a weight (or coefficients of $x_i$).

In some embodiments, to derive a sequence-activity relationship, a set of descriptors ($x_i$) that can describe all of the substitutions within the biopolymer variant set is identified. Values of Y for each member of the biopolymer variant set are measured. Values for each weight ($w_i$) are then calculated such that the differences between values predicted for each value of Y by Equation 3 and those observed experimentally are minimized for the biopolymer variants set, or for a selected subset of such biopolymer variants.

The minimization step above can also use weights for different activity predictions and, in general, can use a loss function. In on embodiment this loss function can be squared error loss, where weights that minimize the sum of squares of the differences between predicted and measured values for the dataset are computed.

In some embodiments statistical regression methods are used to identify relationships between dependent ($x_i$) and independent variables (Y). Such techniques include, but are not limited to, linear regression, non-linear regression, logistic regression, multivariate data analysis, and partial least squares regression. See, for example, Hastie, *The Elements of Statistical Learning,* 2001, Springer, New York; Smith, *Statistical Reasoning,* 1985, Allyn and Bacon, Boston. In one embodiment, regression techniques like the PLS (Partial Least Square) can be used to solve for the weights ($w_i$) in the equation X. Partial Least Squares (PLS) is a tool for modeling linear relationships between descriptors. The method is used to compress the data matrix composed of descriptors (variables) of variant sequences being modeled into a set of latent variable called factors. The number of latent variable is much smaller than the number of variables (descriptors) in the input sequence data. For example, if the number of input variable is 100, the number of latent variables can be less than 10. The factors are determined using the nonlinear iterative partial least squares algorithm. The orthogonal factor scores are used to fit a set of activities to the dependent variables. Even when the predictors are highly collinear or linearly dependent, the method finds a good model. Alternative PLS algorithms like the SIMPLS can also be used for regression. In such methods, the contribution to the activities from every variable can be deconvoluted to study the effect of sequence on the function of the protein.

In some embodiments, modeling techniques are used to derive sequence-activity relationships. Such modeling techniques include linear and non-linear approaches. Linear and non-linear approaches are differentiated from each other based on the algebraic relationships used between variables and responses in such approaches. In the system being modeled, the input data (e.g., variables that serve as descriptors of the biopolymer sequence), in turn, can be linearly related to the variables provided or non-linear combinations of the variables. It is therefore possible to perform different combinations of models and data-types: linear input variables can be incorporated into a linear model, non-linear input variables can be incorporated into a linear model and non-linear variables can be incorporated into a non-linear models.

Many functional forms of f( ) (Eqn. 3) can be used and the functional form can be combined using weights defined in the knowledge base 108 for analysis. For example, Function f( ) can assume non-linear form. An example of non-linear functional form is:

$$Y = w_{12}*x_1*x_2 + w_{123}*x_1*x_3 + w_{nn}*x_n*x_n$$

Non-linear functions can also be derived using modeling techniques such as machine learning methods. For example, the sequence($x_i$)-activity(Y) data to predict the activities of any sequence given the descriptors for a sequence can be determined using neural networks, bayesian models, generalized additive models, support vector machines, classification using regression trees.

The data describing variants of the initial biopolymer can be represented in many forms. In some embodiments, all or a portion of the data is represented in a binary format. For example, representing the presence or absence of a specified residue at a particular position by a "1 or a "0 constitutes a linear binary variable. In another example, representing the presence of a specified residue at one position AND a second specified residue at a second position by a "1" constitutes a non-linear binary variable. In some embodiments, all or a portion of the data is represented as Boolean operators. In some embodiments, all or a portion of the data is represented as principal component descriptors derived from a set of properties. See, for example, Sandberg et al., 1998, J Med Chem. 41, 2481-91. Biopolymer input sequence data can also use descriptors based on comparison with a sequence profile (e.g., a hidden Markov model, or principal component analysis of a set of sequences). For example in FIG. 11, PC1 and PC2 values of the sequences can be used as descriptors for the sequences in that figure. In addition, any number of principle components can be used as descriptors. See, for example, Casari et al., 1995, Nat Struct Biol. 2:171-8; and Gogos et al., 2000, Proteins 40:98-105.

To initiate step 05 (FIG. 2), the biopolymer sequence data in the designed set and the results of the assays performed on the designed set are converted to a form that can be used in pattern classification and/or statistical techniques in order to identify relationships between the results of the assays and the substitutions present in the designed set. In general, such conversion involves a step in which independent variables and dependent variables are enumerated. Here, the independent variables are the various substitutions (mutations) that are present in the designed set. The dependent variables are the results of assays, such as those described in Section 5.9.

Each substitution can be considered independently. The presence or absence of a substitution or residue at a specific position can be used to describe one or more of the independent variables. The presence or absence of two or more substitutions or residues at two or more specific positions can be used to describe one or more of the independent variables. One or more physico-chemical descriptors of a substitution or residue at a specific position can be used to describe one or more of the independent variables. One or more physico-chemical descriptors of two or more substitutions or residues at two or more specific positions can be used to describe one or more of the independent variables. Then, pattern classification and/or statistical techniques are used to identify relationships between particular substitutions, or combinations of substitutions, and the assay data.

In some embodiments, supervised learning techniques are used to identify relationships between mutations in the designed set and biopolymer properties identified in assays results such as assays performed in Section 5.9. Such supervised learning techniques include, but are not limited to, Bayesian modeling, nonparametric techniques (e.g., Parzen windows, $k_n$-Nearest-Neighbor algorithms, and fuzzy classification), neural networks (e.g., hopfield network, multilayer neural networks and support vector machines), and machine learning algorithms (e.g., algorithm-independent machine learning). See, for example, Duda et al., *Pattern Classification*, $2^{nd}$ edition, 2001, John Wiley & Sons, Inc. New York; and Pearl, *Probabilistic Reasoning in Intelligent Systems: Networks of Plausible Inference*, Revised Second Printing, 1988, Morgan Kaufmann, San Francisco. For example, the sequence ($x_i$)-activity (Y) data can be said to predict the activities of any sequence given the descriptors for a sequence using a neural network. The input for the network is the descriptors and the output is the predicted value of Y. The weights and the activation function can be trained using supervised decision based learning rules. The learning is performed on a subset of variants called the training set and performance of the network is evaluated on a test set.

In some embodiments, unsupervised learning techniques are used to identify relationships between mutations in the designed set and biopolymer properties identified in assays results such as assays performed in Section 5.9. Such unsupervised learning techniques include, but are not limited to stochastic searches (e.g., simulated annealing, Boltzmann learning, evolutionary methods, principal component analysis, and clustering methods). See, for example, Duda et al., *Pattern Classification*, $2^{nd}$ edition, 2001, John Wiley & Sons, Inc. New York. For example, the weights in equation 5 can be adjusted by using monte carlo and genetic algorithms. The optimization of weights for non-linear functions can be complicated and no simple analytical method can provide a good solution in closed form. Genetic algorithms have been successfully used in search spaces of such magnitude. Genetic algorithms and genetic programming techniques can also be used to optimize the function form to best fit the data. For instance, many recombinations of functional forms applied on descriptors of the sequence variants can be applied.

In some embodiments, boosting techniques are used to construct and/or improve models developed using any of the other techniques described herein. A model of the sequence-activity relationship can be described as a functional form whose parameters have been trained for the input data (Y and $x_i$). Many algorithms/techniques to build models have been described. Algorithms applied on a specific dataset can be weak in that the predictions can be less accurate or "weak" (yielding poor models). Models can be improved using boosting techniques. See, for example, Hastie et al., *The Elements of Statistical Learning,* 2001, Springer, New York. The purpose of boosting is to combine the outputs of many "weak" predictors into a powerful "committee." In one embodiment of the invention, boosting is applied using the AdaBoost algorithm. Here, the prediction algorithm is sequentially applied to repeatedly modified versions of the data thereby producing a sequence of models. The predictions from all of these models are combined through a weighted majority vote to produce the final prediction. The data modification at each step consists of applying weights ($W^b_i$) to each of the i training observations. Initially weights are set to 1/N, where N is the number of training observation (sequence-activity data). The weights are modified individually in each successive iteration. Training observations that were predicted poorly by a particular model have their weights increased and training observations that were predicted more accurately have their weights decreased. This forces each successive model to concentrate on those training observations that are issued by the previous model. The step of combining the models to produce a "committee" assigns a weight to each model based on the overall prediction error of that model.

The various modeling techniques and algorithms described herein can be adapted to derive relationships between one or more desired properties or functions of a biopolymer and therefore to make multiple predictions from the same model. Modeling techniques that have been adapted to derive sequence-activity relationships for biopolymers are within the scope of the present invention. Some of these methods derive linear relationships (for example partial least squares projection to latent structures) and others derive non-linear relationships (for example neural networks). Algorithms that are specialized for mining associations in the data are also useful for designing sequences to be used in the next iteration of sequence space exploration. These modeling techniques can robustly deal with experimental noise in the activity measured for each variant. Often experiments are performed in replicates and for each variant there will be multiple measurement of the same activity. These multiple measurements (replicate values) can be averaged and treated as a single number for every variant while modeling the sequence-activity relationship. The average can be a simple mean or another form of an average such as a geometric or a harmonic mean. In the case of multiple measurements, outliers can be eliminated. In addition, the error estimation for a model derived using any algorithm can incorporate the multiple measurements through calculating the standard deviation of the measurement and comparing the predicted activity from the model with the average and estimate the confidence interval within which the prediction lies. Weights for observations to be used in models can also be derived from the accuracy of measurement, for example, through estimating standard deviation and confidence intervals. This procedure can put less emphasis on variants whose measurements are not accurate. Alternatively, theses replicate value can be treated independently. This will result in duplicating the sequences in the dataset. For example, if sequence variant i represented by descriptor values $\{x_j\}^{i1}$ has been measured in triplicates ($Y_{i1}, Y_{i2}, Y_{i3}$), the training set for modeling will include descriptor value $\{x_j\}^{i2}$ with activity $Y_{i2}$ and $\{x_j\}^{i3}$ with activity $Y_{i3}$ in addition to $\{x_j\}^{i1}$ with activity $Y_{i1}$, where $\{x_j\}^{i1}=\{x_j\}^{i2}=\{x_j\}^{i3}$.

A representative modeling routine in accordance with one embodiment of the invention comprises the following steps.

Step 302. Relevant descriptors of the monomeric variables are identified. These descriptors can convey physico-chemical properties relevant to the interaction between biomolecules or classify the monomers (residues) as discreet entities represented in binary form as described earlier. The former is preferred for residue positions in the protein sequence where the number of different amino acid substitutions is four or more or where the variables can assume one of four possible values for those positions and the physico-chemical properties values are well distributed (e.g.) different from each other. The latter is preferred for positions that have four or less possible values for the relevant variable, and/or the values are clustered (e.g.) are not very different from each other. To create non-linear variables, new variables are formed that are combination of monomeric variables. For example, consider two variants AGWRY and AKYRY. The linear binary form of the variable (descriptor) for position 2 assumes a value of "1 if G is present at that position and "0 if it is absent. Alternatively, a non-linear variable can be created in addition to the linear variables describing each position. In the above example, a new non-linear variable representing position "2 and "3 can assume four values in numeric form. In one form, the variable can assume a value of 11 for "GW", 10 for "GY", 01 for "KW" and 00 for "KY". In other representations of binary non-linear variable, four variables can describe position 2 and 3, where variable one assumes a value of "1 if the sequence at position 2 and 3 is "GW" and "0 otherwise and the second variable takes the values of "1 or "0 if the sequence is "GY" or otherwise and so on.

In some embodiments it is advantageous to identify regions and thereby variables based on factors including, but not limited to, structures, domains, motifs and exons, optionally using expert system 100 to do so, in order to weigh different variables and their contribution to the model or to build sequence activity models based on these factors. For example, we can assign a weight of 1 for variables in domain A of the protein and 0 for variables in domain B of the protein when modeling activity $Y_1$ and assign a weight of 0 for variables in domain A and 1 for domain B when modeling activity $Y_2$. This weighting can also incorporate constraints such as immunogenicity and other functional considerations that may or may not be measured in experiments, but which can be fully or partially be predicted using computational techniques. For example, a negative weight can be assigned to appearance of a T-cell epitope in a variant, or removal of glycosylation sites.

Step 304. In step 304 the parameters for the functional form of the sequence-activity relationship are optimized to obtain a model by minimizing the difference between the predicted values and real values of the activity of the biopolymer. Such optimization adjusts the individual weights for each descriptors identified in preceding steps using a refinement algorithm such as least squares regression techniques. Other methods that use alternative loss functions for minimization can be used to analyze any particular dataset. For example, in some biopolymer sequence-activity data sets, the activities may not be distributed evenly throughout the measured range. This will skew the model towards data points in the activity space that are clustered. This can be disadvantageous because datasets often contain more data for biopolymer variants with low levels of activity, so the model or map will be biased towards accuracy for these biopolymers which are of lower interest. This skewed distribution can be compensated for by modeling using a probability factor or a cost function based on expert knowledge. This function can be modeled for the activity value or can be used to assign weights to data points based on their activity. As an example, for a set of activities in the range of 0 to 10, transforming the data with a sigmoidal function centered at five will give more weight to sequences with activity above five. Such a function can optionally also be altered with subsequent iterations, thereby focusing the modeling on the part of the dataset with the most desired functional characteristics. This approach can also be coupled with exploring techniques like a Tabu search, where undesired space is explored with lower probabilities.

In some embodiments, algorithms that optimizes the sequence-activity model for the dataset by randomly starting with a solution (e.g., randomly assigning weights w) and using methods like hill-descent and/or monte-carlo and/or genetic algorithm approaches to identify optimal solutions.

In embodiments directed to biopolymer engineering, robustness of the models used is a significant criterion. Thus, obtaining several sub-optimal solutions from various initial conditions and looking at all the models for common features can be a desirable methodology for ensuring the robustness of the solution. Another way to obtain robust solutions is to create bootstrap data sets based on the input data, than estimate a p-value or confidence on the various coefficients of the model. In addition boosting techniques like AdaBoost can be used to obtain a "committee" based solution.

Step 306. Many mathematical modeling techniques for deriving a sequence-activity correlation are evaluated. Preferred mathematical modeling techniques used to identify and capture the sequence-activity correlation handle (i) very large numbers of variables (e.g 20 or more) and correlations between variables, (ii) linear and non-linear interactions between variables, and (iii) are able to extract the variables responsible for a given functional perturbation for subsequent testing of the mathematical model (e.g., models should be easily de-convoluted to assign the effect of variables describing the amino acids substitution with activities).

Step 308. In step 308 the coefficients (parameters) of the model(s) are deconvoluted to see which amino acid substitutions (variables/descriptors of the variants) influence the activity of the biopolymer. It can be important to identify which descriptor of the biopolymer are important for the activity of interest. Some of the techniques, such as partial least squares regression (SIMPLS) that uses projection to latent structures (compression of data matrix into orthogonal factors) may be good at directly addressing this point because contributions of variables to any particular latent factors can be directly calculated. See, for example, Bucht et al., 1999, Biochim Biophys Acta. 1431:471-82; and Norinder et al., 1997, J Pept Res 49:155-62. Other methods such as neural networks can learn from the data very well and make predictions about the activity of entire biopolymers, but it may be difficult to extract information, such as individual contributing features of the biopolymer from the model. Modeling techniques/methods that directly correlate the amino acid variations to the activity are preferred because we can derive the sequence-activity map (relationship) to construct new variants not in dataset that have preferentially higher activities. These methods can be adapted to provide a direct answer and output in desired forms.

Step 310. In step 310 the models developed using various algorithms and methods in the previous step can be evaluated by cross validation methods. For example, by randomly leaving data out to build a model and making predictions of data not incorporated into the model is a standard technique for cross validation. In some instances of biopolymer engineering, data may be generated over a period of months. The data can be added incrementally to the modeling procedure as and when such data becomes available. This can allow for validation of the model with partial or additional datasets, as well as predictions for the properties of biopolymer sequences for which activities are still not available. This information may then be used to validate the model.

Figure 6:
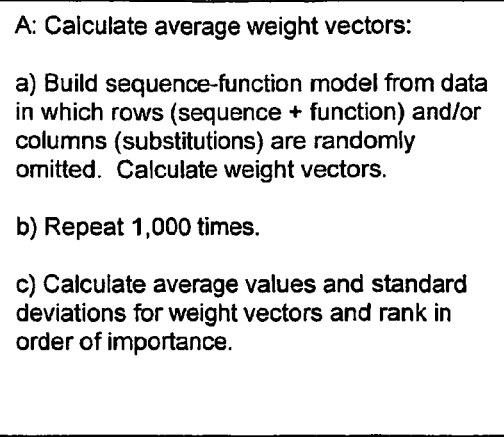
FIG. 6 illustrates a method for calculation of weights (e.g. contributions to activity) for each amino acid substitution in accordance with an embodiment of the present invention.
Figure 7:
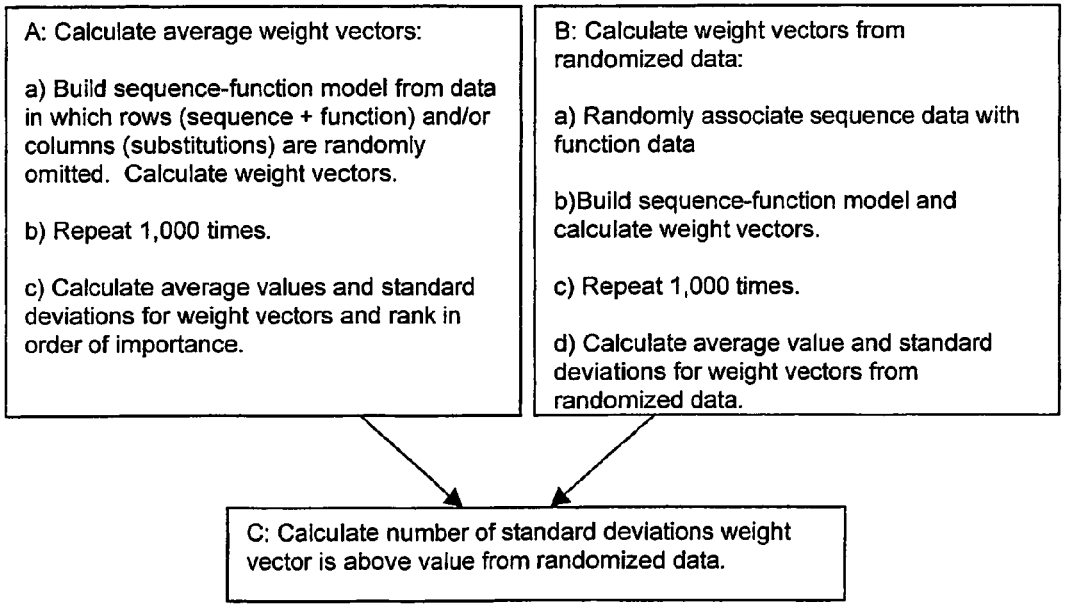
FIG. 7 illustrates a method for calculation of weights (e.g., contributions to activity) for each substitution in accordance with an embodiment of the present invention. This method provides information about the confidence of each weight by comparison with weights obtained from randomized data.

An example of internal model validation methods is shown in FIGS. 6 and 7. In these schemes a confidence score for each regression coefficient or weight vector can be generated for any biopolymer sequence-activity model.

For example, in one embodiment of the present invention, average values for weight functions can be obtained by omitting a part of the available data. Either individual sequences and their associated activities or individual substitution positions can be left out. A sequence-activity relationship can then be constructed from this partial data. This process can be repeated many times, each time the data to leave out is selected randomly. Finally an average and range of values for each weight function is calculated. The weight functions can then also be ranked in order of their importance to activity.

To assess the probability that a substitution is associated with an activity by random chance, the same weight function calculations can be performed when the sequences and activities are randomly associated (FIG. 7). In this case there should be no relationship between sequence and function, so weight functions arise only by chance. A measure of the confidence for the weight function can then be calculated. It is related to the number of standard deviations by which the value calculated when sequences and activities are correctly associated exceeds the value calculated when they are randomly associated. The above methods on model assessment, model inference and averaging are discussed in detail by Hastie et al., 2001, Springer Verlag, series in statistics.

Step 312. In step 312 new biopolymer sequences that are predicted to possess one or more desired property are derived. Alternatively it can be desirable to rank order the input variables for detailed sequence-activity correlation measures. The model can be used to propose sequences that have high probabilities of being improved. Such sequences can then be synthesized and tested. In one embodiment, this can be achieved if the effects of various sequence features of the biopolymers on their functions are known based on the modeling. Alternatively, for methods like neural networks, $10^3$ or $10^6$ or $10^9$ or $10^{12}$ or $10^{15}$ or $10^{18}$ or as many as $10^{80}$ sequences can be evaluated in silico. Then those predicted by the model to possess one or more desired properties are selected.

Step 314. The statistical quality of the model fit to the input data is evaluated in step 314. Validation of sequence-activity correlation can be internal, using cross-validation of the data, or preferably external, by forecasting the functional perturbation of a set of new sequences derived from the model. Sequences with predicted values of their functional perturbations are then physically made and tested in the same experimental system used to quantify the training set. If the sequence-activity relationship of the dataset is satisfactory quantified using internal and external validation, the model can be applied to a) predict the functional value of other related sequences not present in the training set, and b) design new sequences within the described space that are likely to have a function value that is outside or within the range of function given by the training set.

The initial set of data can be small, so models built from it can be inaccurate. Initial models may not contain terms to account for amino acid interactions. Others have found that amino acid changes within a protein are approximately additive and few interaction terms are required to describe the effects of mutations on protein function. See, for example, Aita et al. (2000) Biopolymers 54: 64-79.; Aita et al. (2001) Protein Eng 14: 633-8.; Choulier et al. (2002) Protein Eng 15: 373-82.; and Prusis et al. (2002) Protein Eng 15: 305-11.

However such interactions can be important and can result in a variant that incorporates all beneficial changes having low activity (Aita et al., 2002, Biopolymers 64: 95-105.). Improving the modeled relationship further depends upon obtaining better values for weights whose confidence scores are low. To obtain this data, additional variants designed as described in Section 5.4 below will provide additional data useful in establishing more precise sequence-activity relationships.

The output from each method for modeling a sequence-activity relationship can be one or more of: (i) a regression coefficient, weight or other value describing the relative or absolute contribution of each substitution or combination of substitutions to one or more activity of the biopolymer, (ii) a standard deviation, variance or other measure of the confidence with which the value describing the contribution of the substitution or combination of substitutions to one or more activity of the biopolymer can be assigned, (iii) a rank order of preferred substitutions, (iv) the additive & non-additive components of each substitution or combination of substitutions, (v) a mathematical model that can be used for analysis and prediction of the functions of in silico generated sequences, (vi) a modification of one or more inputs or weights used by an expert system 100 to select substitutions or (vii) a modification of the methods used by expert system 100 to design a biopolymer variant set.

5.3.1 Methods for Combining the Results from Two or More Sequence-Activity Relationship Modeling Methods.

It will be appreciated by one skilled in the art that each different method for deriving relationships between biopolymer sequences and activities can differ in the precise values of their outputs. In some embodiments of the invention it is therefore desirable to combine the outputs from two or more such methods for subsequent uses. This corresponds to step 06 in FIG. 2. There are a variety of ways in which such outputs can be combined. In some embodiments, each output can be independently applied to the subsequent design of biopolymer variants (FIG. 2, step 07) or the modification of parameters or weights used by expert system 100 for the selection of substitutions (FIG. 2 step 02) or the design of biopolymer variant sets (FIG. 2 step 03). In some embodiments, average values (or some other mathematical function of two or more values derived by two or more sequence-activity models) can be calculated for the regression coefficient, weight or other value describing the relative or absolute contribution of each substitution or combination of substitutions to one or more activity of the biopolymer (e.g., as defined in Equation 4 below). In some embodiments, the standard deviation, variance or other measure of the confidence with which the value describing the contribution of the substitution or combination of substitutions to one or more activity of the biopolymer can be assigned (e.g., as defined in Equation 4 below). In some embodiments, the rank order of preferred substitutions is used to combine the methods. In some embodiments, the additive (linear variables) and non-additive components (non-linear variables) of each substitution or combination of substitutions is combined:

$$V_{ix} = f(M_1(i_x), M_2(i_x), \ldots, M_j(i_x)) \quad \text{(Eq. 4)}$$

where, $V_{ix}$ is a combined measure of one of the descriptors measuring the performance of a biopolymer in which monomer x is substituted at position i;

$M_j(i_x)$ is a measure of one of descriptors measuring the performance of a biopolymer in which monomer x is substituted at position i, determined by sequence-activity correlating method j ($M_j(i_x)$ is the contribution of $i_x$ as determined by Model j); and f( ) is some mathematical function.

In one embodiment f( ) can be a linear combination of contribution of $i_x$ from many models.

In some embodiments, independent values can be obtained for the functional values of in silico generated sequences derived from two or more mathematical models by using the model generated in the prior steps to predict/calculate the value of the new sequence represented in terms of the same variables that are used to build the model. In some embodiments, average values (or some other mathematical function of two or more values derived by two or more sequence-activity models) can be obtained for the functional values of in silico generated sequences derived from two or more mathematical models.

The methods used to derive sequence-activity relationships can be chosen or modified such that they better predict the performance of individual substitutions within a combination of other substitutions in a biopolymer, as described in more detail in Subsection 5.4.4.

5.4 Use of Sequence-Activity Relationships to Design Optimized Variants or Additional Variant Sets There are many ways to use the results of sequence-activity correlations described in Section 5.3 in the design of a subsequent set of variants. This corresponds to step 07 of FIG. 2. Conceptually, this step is similar to the processes corresponding to steps 02 and 03 in FIG. 2. It involves defining a sequence space in terms of a biopolymer sequence and a set of substitutions, then designing a set of biopolymer variants that incorporate those substitutions in different combinations.

5.4.1 Definition of the Sequence Space to Represent Additional Variant Sets

A few methods for defining a sequence space for an optimized variant or additional variant set, using a biopolymer sequence and a set of substitutions are enumerated here by way of examples not intended to limit the scope of the present invention.

In one embodiment the sequence space can be defined in terms of the original target biopolymer sequence and substitutions that have already been tested. In preferred embodiments of the invention, this method for defining the sequence space is used if the desired degree of further increase in one or more activity of the biopolymer is less than 10-fold, preferably less than 5-fold, more preferably less than 2-fold.

In another embodiment, the sequence space can be defined in terms of the original target biopolymer sequence and a combination of substitutions that have already been tested and those that have not yet been tested. In preferred embodiments of the invention, this method for defining the sequence space is used if the desired degree of further increase in one or more activity of the biopolymer is greater than 2-fold, preferably greater than 5-fold, and more preferably greater than 10-fold.

In still another embodiment, the sequence space can be defined purely in terms of the original target biopolymer sequence and substitutions that have not yet been tested. This method for defining the sequence space is generally most appropriate for the initial variant set as represented in FIG. 2 step 02.

5.4.2 Assessment of Previously Tested Substitutions for Incorporation into Optimized Variants or Additional Variant Sets The methods for selecting substitutions that have not previously been tested have been described in Section 5.1. Methods for selecting or eliminating substitutions that have previously been tested use one or more of the outputs from the methods for correlating biopolymer sequences with their activities. A few methods for defining a sequence space for an optimized variant or additional variant set, using a biopolymer sequence and a set of substitutions are enumerated here by way of examples. In the following examples, the term "substitution" can also mean a pair or larger group of substitutions (for example, when the descriptors of proteins are represented in non-linear form as described in section 5.3), since sequence-activity relationships can produce regression coefficients, weights or other measurements of contribution to function and confidences for these measurements that apply not to individual substitutions but to specific combinations of these substitutions.

(i) A substitution can be selected if it has a positive regression coefficient, weight or other value describing its relative or absolute contribution to one or more activity of the biopolymer.

(ii) A substitution can be selected if it has a positive regression coefficient, weight or other value describing its relative or absolute contribution to one or more activity of the biopolymer, and it is at least one standard deviation, preferably two standard deviations or more preferably three standard deviations above neutrality.

(iii) A substitution can be selected if it has a positive regression coefficient, weight or other value describing its relative or absolute contribution to one or more activity of the biopolymer, and it has also been tested at least once, preferably at least twice, more preferably at least three times, more preferably at least four times, even more preferably at least five times.

(iv) A substitution can be selected if it has a positive regression coefficient, weight or other value describing its relative or absolute contribution to one or more activity of the biopolymer, and it is at least one standard deviation, preferably two standard deviations or more preferably three standard deviations above neutrality, and it has also been tested at least once, preferably at least twice, more preferably at least three times, more preferably at least four times, even more preferably at least five times.

(v) A substitution can be selected from a rank ordered list of substitutions. For example the most favorable substitution may be selected, or the 2, 3, 4, 5, 6, 7, 8, 9, 10, 11, 12, 13, 14, 15, 16, 17, 18, 19 or 20 most favorable substitutions can be selected.

(vi) A substitution can be selected from a rank ordered list of substitutions. For example, the most favorable substitution can be selected, or the 2, 3, 4, 5, 6, 7, 8, 9, 10, 11, 12, 13, 14, 15, 16, 17, 18, 19 or 20 most favorable substitutions can be selected, and it is at least one standard deviation, preferably two standard deviations or more preferably three standard deviations above neutrality.

(vii) A substitution can be selected from a rank ordered list of substitutions. For example, the most favorable substitution can be selected, or the 2, 3, 4, 5, 6, 7, 8, 9, 10, 11, 12, 13, 14, 15, 16, 17, 18, 19 or 20 most favorable substitutions can be selected, and it has also been tested at least once, preferably at least twice, more preferably at least three times, more preferably at least four times, even more preferably at least five times.

(viii) A substitution can be selected from a rank ordered list of substitutions. For example, the most favorable substitution may be selected, or the 2, 3, 4, 5, 6, 7, 8, 9, 10, 11, 12, 13, 14, 15, 16, 17, 18, 19 or 20 most favorable substitutions can be selected, and it is at least one standard deviation, preferably two standard deviations or more preferably three standard deviations above neutrality, and it has also been tested at least once, preferably at least twice, more preferably at least three times, more preferably at least four times, even more preferably at least five times.

(ix) A substitution can be selected if it has a negative regression coefficient, weight or other value describing its relative or absolute contribution to one or more activity of the biopolymer, and it is less than three standard deviations, preferably less than two standard deviations or more preferably less than one standard deviation below neutrality.

(x) A substitution can be selected if it has a negative regression coefficient, weight or other value describing its relative or absolute contribution to one or more activity of the biopolymer, and it has also been tested no more than five times, preferably no more than four times, more preferably no more than three times, more preferably no more than twice, even more preferably no more than once.

(xi) A substitution can be selected if it has a negative regression coefficient, weight or other value describing its relative or absolute contribution to one or more activity of the biopolymer, and it is less than three standard deviations, preferably less than two standard deviations or more preferably less than one standard deviation below neutrality, and it has also been tested no more than 5 times, preferably no more than 4 times, more preferably no more than three times, more preferably no more than twice, even more preferably no more than once.

(xii) A substitution can be eliminated if it has a negative regression coefficient, weight or other value describing its relative or absolute contribution to one or more activity of the biopolymer.

(xiii) A substitution can be eliminated if it has a negative regression coefficient, weight or other value describing its relative or absolute contribution to one or more activity of the biopolymer, and it is at least one standard deviation, preferably two standard deviations or more preferably three standard deviations above neutrality.

(xiv) A substitution can be eliminated if it has a negative regression coefficient, weight or other value describing its relative or absolute contribution to one or more activity of the biopolymer, and it has also been tested at least once, preferably at least twice, more preferably at least three times, more preferably at least four times, even more preferably at least five times.

(xv) A substitution can be eliminated if it has a negative regression coefficient, weight or other value describing its relative or absolute contribution to one or more activity of the biopolymer, and it is at least one standard deviation, preferably two standard deviations or more preferably three standard deviations above neutrality, and it has also been tested at least once, preferably at least twice, more preferably at least three times, more preferably at least four times, even more preferably at least five times.

5.4.3 Methods for Designing Biopolymer Variant Sets Incorporating Previously Tested Substitutions Biopolymer variants that combine or eliminate previously tested substitutions can serve at least two purposes. First, they can be used to obtain biopolymer variants that are improved for one or more property, activity or function of interest. Generally, though not exclusively, substitutions selected according to criteria (i)-(viii) in subsection 5.4.2 are most likely to be appropriate for this purpose. Second, they can be used to obtain additional information relating the sequence to the activity of a biopolymer, thereby improving the accuracy with which predictions can be made concerning the effect of substitutions upon one or more property, activity or function of a biopolymer. Generally, though not exclusively, substitutions selected according to criteria (i)-(xi) in subsection 5.4.2 are most likely to be appropriate for this purpose.

The following methods can be used to design biopolymer variants containing combinations of substitutions selected by one or more of the methods described in subsection 5.4.2.

Method 1. A biopolymer that has previously been tested for the one or more property, activity or function of interest is selected. In preferred embodiments the selected biopolymer has one of the 100 highest experimentally measured scores for the property, activity or function of interest, more preferably one of the 50 highest experimentally measured scores, even more preferably one of the 25 highest experimentally measured scores, even more preferably one of the 10 highest experimentally measured scores.

The substitutions in the selected biopolymer are combined with one or more substitutions selected by one or more of the methods described in subsection 5.4.2. In preferred embodiments less than 10 selected substitutions are used, more preferably less than 5 selected substitutions are used, even more preferably less than 3 selected substitutions are used.

Method 2. A biopolymer that has previously been tested for the one or more property, activity or function of interest is selected. In preferred embodiments the selected biopolymer has one of the 100 highest experimentally measured scores for the property, activity or function of interest, more preferably one of the 50 highest experimentally measured scores, even more preferably one of the 25 highest experimentally measured scores, even more preferably one of the 10 highest experimentally measured scores.

The substitutions in the selected biopolymer are combined with one or more substitutions selected by one or more of the methods described in subsection 5.4.2. In preferred embodiments less than 10 selected substitutions are used, more preferably less than 5 selected substitutions are used, even more preferably less than 3 selected substitutions are used. In addition, these substitutions are combined with one or more substitutions selected by one or more method described in Section 5.1 (i.e., by the methods used in step 03 of FIG. 2). In preferred embodiments, less than 10 of these last selected substitutions are used, more preferably less than 5 of these last selected substitutions are used, even more preferably less than 3 of these last selected substitutions are used.

Method 3. Two or more substitutions identified by one or more of the methods described in subsection 5.4.2 are selected. In preferred embodiments less than 100 selected substitutions, more preferably less than 50, and even more preferably less than 25 are used. One or more biopolymer variants containing these substitutions are designed using the methods described in Section 5.2.

Method 4. One or more substitutions selected by one or more of the methods described in subsection 5.4.2 are selected. In preferred embodiments less than 100 selected substitutions, more preferably less than 50, and even more preferably less than 25 are used. One or more substitutions are selected using one or more of the methods described in Section 5.1. In preferred embodiments, less than 100, and more preferably less than 50 of these selected substitutions are used. Then, one or more biopolymer variants are designed using the methods described in Section 5.2.

Method 5. One or more substitutions selected by one or more of the methods described in subsection 5.4.2 that contribute most positively to the property (e.g., function, activity of interest) are selected. In preferred embodiments, between 1 and 20 most positive substitutions are selected. One or more biopolymer variant that has already been tested for the property is selected. In preferred embodiments, the between 1 and 20 most active biopolymers are selected. One or more of the selected substitutions is added to each of the one or more selected biopolymers. In preferred embodiments, the number of substitution positions to be added to each biopolymer variant sequence is between 1 and 10, more preferably between 1 and 6, and even more preferably between 1 and 3.

Method 6. Substitutions whose regression coefficients, weights or other values describing the relative or absolute contribution to one or more activity of the biopolymer are positive are selected. Those substitutions whose regression coefficients, weights or other values describing the relative or absolute contribution to one or more activity of the biopolymer have confidences within a threshold distance from the randomized average weight for that substitution are eliminated. In preferred embodiments, this threshold distance is within 1 standard deviation, more preferably within 2 standard deviations. The substitutions with positive weights and high confidences are combined into a single variant. Alternatively, the selected substitutions are used to design a set of biopolymer variants as described in Section 5.2.

Method 7. Substitutions are ranked in the order in which confidences can be assigned to regression coefficients, weights or other values describing the relative or absolute contribution to one or more activity of the biopolymer. The substitutions with lowest confidence scores are selected. From the sequences of biopolymer variants whose activities have already been measured, those that have high values for the property of interest are selected. In preferred embodiments, between 1 and 20 tested biopolymer variant sequences with highest activities are selected. One or more of the selected substitutions is added to each selected variant. In preferred embodiments, the number of substitutions to be added to each biopolymer variant sequence is between 1 and 10, more preferably between 1 and 6, and even more preferably between 1 and 3.

Method 8. One or more biopolymer variants that have already been tested for the property of interest are selected. In preferred embodiments, between 1 and 20 most active biopolymers are selected. One or more substitutions for which a contribution to the property has been calculated are selected. For each of the one or more selected biopolymers, the following process is performed. One of the selected substitutions is added or removed and the predicted activity of the resultant biopolymer is calculated using one or more models for sequence-activity relationship as described in the section 5.3. Exemplary models include, but are not limited to (i) regression techniques that provide regression coefficients for the descriptors, (ii) models that generate weights or other value describing the relative or absolute contribution of each substitution or combination of substitutions to one or more activity of the biopolymer, (iii) models that provide standard deviation, variance or other measures of the confidence with which the value describing the contribution of the substitution or combination of substitutions to one or more activity of the biopolymer can be assigned, (iv) models that rank order preferred substitutions, (v) models that provide additive and non-additive components of each substitution or combination of substitutions, (vi) analytical mathematical models that can be used for analysis and prediction of the functions of in silico generated sequences (vii) supervised and unsupervised machine learning techniques like neural networks that can predict the activity of new biopolymer sequences expressed in terms of the descriptors that are used in modeling.

If the predicted activity of the new biopolymer is greater than the predicted value of the biopolymer before the change, the change is incorporated. Otherwise, the process reverts to the sequence of the biopolymer before the change. This process continues for a certain number of steps (preferably more than 10 steps, more preferably more than 100 steps, even more preferably more than 1000 steps) or until the predicted activity of the biopolymer converges to a value. Either the final biopolymer sequence in the series of iterations of the method, or the biopolymer sequence in the series with the highest predicted activity is selected. This process can optionally be performed more than once starting from each initial biopolymer sequence.

Method 9. As an optional addition to any of the design methods including methods 1, 2, 5, and 7, one or more substitutions determined to be detrimental to the desired property (e.g., by any of the criteria described in subsection 5.4.2 including criteria (xii)-(xv)) are eliminated.

Method 10. As an optional addition to any design method, newly designed variants that can be reached by making a certain number of substitutions to a biopolymer sequence whose activity has already been measured are discarded and not synthesized. In preferred embodiments newly designed variants that can be reached by making 10 or fewer substitutions to a biopolymer sequence whose activity has already been measured are not synthesized. More preferably, newly designed variants that can be reached by making 5 or fewer substitutions to a biopolymer sequence whose activity has already been measured are not synthesized. More preferably, newly designed variants that can be reached by making 3 or fewer substitutions to a biopolymer sequence whose activity has already been measured are not synthesized. Even more preferably, newly designed variants that can be reached by making 2 or fewer substitutions to a biopolymer sequence whose activity has already been measured are not synthesized. Most preferably, newly designed variants that can be reached by making 1 to a biopolymer sequence whose activity has already been measured are not synthesized.

One skilled in the art will appreciate that there are many possible ways of using sequence-activity information to design improved biopolymer variants. The schemes outlined above are intended to illustrate a few of the design possibilities.

5.4.4 Methods for Modifying the Choice and Combinations of Methods Used to Determine Sequence-Activity Relationships The performances of different sequence-activity modeling methods can be quantitatively compared. Such comparisons can be used to modify variable parameters within each method, or to select methods of combining the results of two or more sequence-activity correlating methods as outlined in Subsection 5.3.1.

The outputs of methods that determine sequence-activity relationship are outlined in Section 5.3. These outputs can be combined to calculate the predicted activity of a biopolymer and the confidence with which that activity can be predicted. These predictions can be compared with activity values obtained experimentally for newly designed and synthesized biopolymer variants, and the method or methods of deriving sequence-activity relationships may be chosen or modified in one or more of the following ways.

1. The weights applied to the scores produced by the one or more sequence-activity correlating methods, for example as shown in Equation 4 or as described in Subsection 5.3.1 can be modified such that one or more of the following are true.
   (i) The activity value predicted for the most active newly designed and synthesized biopolymer variant most closely matches the experimentally determined activity for that variant.
   (ii) The rank order of activity values predicted for some number of the most active newly designed and synthesized biopolymer variants most closely match the experimentally determined rank order of activity for those variants. In preferred embodiments the rank order of activity values predicted for the 5 most active newly designed and synthesized biopolymer variants most closely matches the experimentally determined rank order of activity for those variants, more preferably the rank order of activity values predicted for the 10 most active newly designed and synthesized biopolymer variants most closely matches the experimentally determined rank order of activity for those variants, even more preferably the rank order of activity values predicted for the 15 most active newly designed and synthesized biopolymer variants most closely matches the experimentally determined rank order of activity for those variants.
   (iii) The fewest newly designed and synthesized biopolymer variants predicted to be more active than the initial target biopolymer possess experimentally determined activity that is lower than the initial target biopolymer.
   (iv) The fewest newly designed and synthesized biopolymer variants predicted to be more active than the most active previously tested biopolymer possess experimentally determined activities that are lower than the most active previously tested biopolymer.

2. The sequence-activity correlating method is chosen such that one or more of the following are true.
   (i) The activity value predicted for the most active newly designed and synthesized biopolymer variant most closely matches the experimentally determined activity for that variant.
   (ii) The rank order of activity values predicted for some number of the most active newly designed and synthesized biopolymer variants most closely match the experimentally determined rank order of activity for those variants. In preferred embodiments the rank order of activity values predicted for the 5 most active newly designed and synthesized biopolymer variants most closely matches the experimentally determined rank order of activity for those variants, more preferably the rank order of activity values predicted for the 10 most active newly designed and synthesized biopolymer variants most closely matches the experimentally determined rank order of activity for those variants, even more preferably the rank order of activity values predicted for the 15 most active newly designed and synthesized biopolymer variants most closely matches the experimentally determined rank order of activity for those variants.
   (iii) The fewest newly designed and synthesized biopolymer variants predicted to be more active than the initial target biopolymer possess experimentally determined activities that are lower than the initial target biopolymer.
   (iv) The fewest newly designed and synthesized biopolymer variants predicted to be more active than the most active previously tested biopolymer possess experimentally determined activities that are lower than the most active previously tested biopolymer.

3. In some embodiments, the process of steps 1 or 2 can be performed using regression techniques, machine learning or other multivariate data analysis tools to calculate or minimize the differences between the values predicted by the sequence-activity relationship, and those observed experimentally.

4. In some embodiments, the process of steps 1 or 2 can be performed using values predicted by the sequence-activity relationship, and those observed experimentally for more than one set of biopolymers.

5. In some embodiments the process of step 4 can be performed using two or more datasets from biopolymers that fall into the same class and subclass. For example, two or more sets of optimized antibodies, two or more sets of transcription factors, two or more sets of receptors, two or more sets of growth factors (e.g., any of the PDGFs, EGFs, FGFs, SCF, HGF, TGFs, TNFs, insulin, IGFs, LIFs, oncostatins, and CSFs), two or more sets of immunomodulators, two or more sets of cytokines, two or more sets of integrins, two or more sets of interleukins, two or more sets of adhesion molecules, two or more sets of thrombomodulatory molecules, two or more sets of protease inhibitors, two or more sets of angiostatin, two or more sets of defensins, two or more sets of interferons, two or more sets of chemokines, two or more sets of antigens including those from infectious viruses and organisms, two or more sets of oncogene products, two or more sets of proteases, two or more sets of polymerases, two or more sets of depolymerases, two or more sets of kinases, two or more sets of phosphatases, two or more sets of cyclins, two or more sets of cyclin-dependent kinases, two or more sets of glycosidases, two or more sets of polyketide synthases, two or more sets of non-ribosomal peptide synthases, two or more sets of insecticidal proteins, two or more sets of cytochrome P450s, two or more sets of lipases, two or more sets of esterases, two or more sets of cutinases, two or more sets of terpene cyclases, two or more sets of transferases, two or more sets of glycosyl transferases, two or more sets of methylases, two or more sets of methyl transferases. Weights for expert system rules 120 that are modified using two or more datasets from biopolymers of the same class and subclass can be stored, for example in knowledge base 108 or case-specific data 110. These weights or choices for sequence-activity determining methods can then be used by expert system 100 when a subsequent target biopolymer sequence and activity dataset of that class and subclass is presented.

6. In some embodiments the process of step 4 can be performed using two or more datasets from biopolymers that fall into the same class. For example two or more sets of proteins, two or more sets of peptides, two or more sets of polynucleotides, two or more sets of polyketides, two or more sets of non-ribosomal peptides. Weights for expert system 100 rules 120 that are modified using two or more datasets from biopolymers of the same class can be stored, for example in knowledge base 108 or case-specific data 110. These weights for expert system 100 rules 120 can then be used by expert system 100 when a subsequent target biopolymer sequence and activity dataset of that class and subclass is presented.

5.5 Use of Sequence-Activity Relationships to Train an Expert System for Substitution Identification The endpoint of a process of biopolymer optimization is reached when one or more biopolymers are obtained with one or more properties at the levels defined by a user, these activity levels being appropriate to allow the use of the biopolymer in performing a specific task. This corresponds to FIG. 2 step 08.

In addition to designing improved biopolymer variants, information from sequence-activity relationships can be used to provide information to improve the initial selection of substitutions, for example by modifying the weights applied to the scores produced by the expert system 100 as described in Section 5.1. As an example, the weights can be modified according to the following process.

1. As described in Section 5.3, the sequence-activity relationship can be used to calculate (i) a regression coefficient, weight or other value describing the relative or absolute contribution of each substitution or combination of substitutions to one or more activity of the biopolymer, (ii) a standard deviation, variance or other measure of the confidence with which the value describing the contribution of the substitution or combination of substitutions to one or more activity of the biopolymer can be assigned, and/or (iii) a rank order of preferred substitutions.

2. The results of applying two or more rules 120 of expert system 100 are combined and can be used to obtain (i) a score describing the predicted effect of a substitution upon one or more biopolymer property, (ii) a probability or confidence describing the predicted effect of a substitution upon one or more biopolymer property, activity or function, or (iii) a predicted rank order of preferred substitutions. Different values for each of these predictions can result from modifications of the weights applied to the scores produced by expert system 100 as described in Section 5.1, for example as shown in equations (1) or (2).

3. The weights applied to the scores produced by expert system 100 can be modified such that one or more of the following are true.

(i) The regression coefficient, weight or other value describing the relative or absolute contribution of each substitution or combination of substitutions to one or more activity of the biopolymer that is derived from the sequence-activity relationship more closely corresponds (or correlates) with the score describing the predicted effect of a substitution upon one or more biopolymer property, activity or function that is derived from expert system 100.

(ii) The standard deviation, variance or other measure of the confidence with which the value describing the contribution of the substitution or the combination of substitutions to one or more activity of the biopolymer can be assigned that is derived from the sequence-activity relationship more closely corresponds (or correlates) with the probability or confidence describing the predicted effect of a substitution upon one or more biopolymer property, activity or function that is derived from expert system 100.

(iii) The rank order of preferred substitutions that is derived from the sequence-activity relationship more closely corresponds (or correlates) with the predicted rank order of preferred substitutions that is derived from expert system 100.

4. In some embodiments, the process of steps 1 to 3 can be performed using regression techniques, machine learning or other multivariate data analysis tools to minimize the differences between the values obtained from the sequence-activity relationship, and those predicted by expert system 100.

5. In some embodiments, the process of steps 1 to 3 can be performed using expert system 100 predictions and sequence-activity relationships for more than one set of biopolymers.

6. In some embodiments the process of step 5 can be performed using two or more datasets from biopolymers that fall into the same class and subclass. For example, two or more sets of optimized antibodies, two or more sets of transcription factors, two or more sets of receptors, two or more sets of growth factors (any of the PDGFs, EGFs, FGFs, SCF, HGF, TGFs, TNFs, insulin, IGFs, LIFs, oncostatins, and CSFs), two or more sets of immunomodulators, two or more sets of cytokines, two or more sets of integrins, two or more sets of interleukins, two or more sets of adhesion molecules, two or more sets of thrombomodulatory molecules, two or more sets of protease inhibitors, two or more sets of angiostatins, two or more sets of defensins, two or more sets of interferons, two or more sets of chemokines, two or more sets of antigens including those from infectious viruses and organisms, two or more sets of oncogene products, two or more sets of proteases, two or more sets of polymerases, two or more sets of depolymerases, two or more sets of kinases, two or more sets of phosphatases, two or more sets of cyclins, two or more sets of cyclin-dependent kinases, two or more sets of glycosidases, two or more sets of polyketide synthases, two or more sets of non-ribosomal peptide synthases, two or more sets of insecticidal proteins, two or more sets of cytochrome P450s, two or more sets of lipases, two or more sets of esterases, two or more sets of cutinases, two or more sets of terpene cyclases, two or more sets of transferases, two or more sets of glycosyl transferases, two or more sets of methylases, two or more sets of methyl transferases. Weights for expert system 100 rules 120 that are modified using two or more datasets from biopolymers of the same class and subclass can be stored, for example in knowledge base 108 or case-specific data 110. These weights for expert system rules 120 can then be used by expert system 100 when a subsequent target biopolymer of that class and subclass is presented.

7. In some embodiments the process of step 5 can be performed using two or more datasets from biopolymers that fall into the same class. For example, two or more sets of proteins, two or more sets of peptides, two or more sets of polynucleotides, two or more sets of polyketides, two or more sets of non-ribosomal peptides. Weights for expert system 100 rules 120 that are modified using two or more datasets from biopolymers of the same class can be stored, for example in knowledge base 108 or case-specific data 110. These weights for rules 120 can then be used by expert system 100 when a subsequent target biopolymer of that class is presented.

By using a formal system for substitution selection, predictions made by expert system 100 can be improved so that preferences (e.g. higher weights) are given to selection methods 130 that have performed well in previous iterations.

Different algorithms and methods for identifying productive substitutions and for deriving sequence activity relationships may be better suited to different types of biopolymer, including different protein families, different nucleic acid regulatory motifs or functional molecules and different polyketide classes.

By using feedback loops of this nature, where quantitative scoring or ranking protocols are developed, a learning, automated computational system for biopolymer optimization can be developed. This system could include generic information applicable to all biopolymer classes and specific information applicable to a more limited subset of biopolymers.

Such a computational system could be made available directly, via the internet and/or on a subscription basis.

5.6 Utility of the Variants of this Invention

Other useful products produced by the method of the invention include biopolymers incorporating substitutions identified through construction and characterizing sets of variant biopolymers. Where the biopolymer is a polynucleotide this also includes vectors (including expression vectors) comprising such polynucleotides, host cells comprising such polynucleotides and/or vectors, and libraries of biological polymers, and libraries of host cells comprising and/or expressing such libraries of biological polymers.

While the utility of the variants of this invention will be evident to one of skill in the art, the variants will be particularly useful in preparation of polynucleotides, polyketides, proteins including antibodies, immunoconjugates, transcription factors, receptors, growth factors (any of the PDGFs, EGFs, FGFs, SCF, HGF, TGFs, TNFs, insulin, IGFs, LIFs, oncostatins, and CSFs), immunomodulators, peptide hormones, cytokines, integrins, interleukins, adhesion molecules, thrombomodulatory molecules, protease inhibitors, angiostatins, defensins, cluster of differentiation antigens, interferons, chemokines, antigens including those from infectious viruses and organisms, oncogene products, thrombopoietin, erythropoietin, tissue plasminogen activator, proteases, polymerases, depolymerases, kinases, phosphatases, cyclins, cyclin-dependent kinases, glycosidases, transferases, glycosyl transferases, methylases, methyl transferases, polyketide synthases, non-ribosomal peptide synthases, insecticidal proteins, cytochrome P450s, lipases, esterases, cutinases, terpene cyclases, enzymes, antigens, ligands, immunomodulators, receptors or therapeutic proteins with increased activity, polynucleotides encoding any of the above, polyketides, enzymes, antigens, ligands, immunomodulators, receptors or therapeutic proteins with modified activity, enzymes, antigens, ligands, immunomodulators, receptors or therapeutic proteins with increased stability, removal or addition of immunogenic epitopes from proteins, improving expression levels of polynucleotides, polyketides and polypeptides and improving the therapeutic utility of polynucleotides, polyketides and polypeptides.

5.7 Definitions

It is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Unless defined otherwise herein, all technical and scientific terms used herein have the same meaning as commonly understood by one of ordinary skill in the art to which this invention belongs. Singleton et al., *Dictionary Of Microbiology And Molecular Biology*, $2^{nd}$ ed., John Wiley and Sons, New York (1994), and Hale & Marham, *The Harper Collins Dictionary Of Biology*, Harper Perennial, NY (1991) provide one of skill with a general dictionary of many of the terms used in this invention. Bioinformatic terms referring to expert systems are used in the same sense that they appear in Jackson, *Introduction To Expert Systems*, $3^{rd}$ ed., Addison-Wesley, NY (1999). Although any methods and materials similar or equivalent to those described herein can be used in the practice or testing of the present invention, the preferred methods and materials are described. Unless otherwise indicated, nucleic acids are written left to right in 5' to 3' orientation; amino acid sequences are written left to right in amino to carboxy orientation, respectively. The headings provided herein are not limitations on the invention, but exemplify the various aspects of the invention. Accordingly, the terms defined immediately below are more fully defined by reference to the specification as a whole.

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

Where the polynucleotides are to be used to express encoded proteins, nucleotides which can perform that function or which can be modified (e.g., reverse transcribed) to perform that function are used. Where the polynucleotides are to be used in a scheme which requires that a complementary strand be formed to a given polynucleotide, nucleotides are used which permit such formation.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-.beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidi-ne) to form isocytosine (1-.beta.-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described in U.S. Pat. No. 5,780,610 to Collins et al. Other nonnatural base pairs may be synthesized by the method described in Piccirilli et al. (1990) Nature 343:33-37 for the synthesis of 2,6-diaminopyrimidine and its complement (1-methylpyrazolo-[4,3] pyrimidine-5,7-(4H,6H)-dione. Other such modified nucleotidic units which form unique base pairs are known, such as those described in Leach et al. (1992) J. Am. Chem. Soc. 114:3675-3683 and Switzer et al., supra.

The phrase "DNA sequence" refers to a contiguous nucleic acid sequence. The sequence can be either single stranded or double stranded, DNA or RNA, but double stranded DNA sequences are preferable. The sequence can be an oligonucleotide of 6 to 20 nucleotides in length to a full length genomic sequence of thousands of base pairs.

The term "protein" refers to contiguous "amino acids" or amino acid "residues." Typically, proteins have a function. However, for purposes of this invention, proteins also encompasses polypeptides and smaller contiguous amino acid sequences that do not have a functional activity. The functional proteins of this invention include, but are not limited to, esterases, dehydrogenases, hydrolases, oxidoreductases, transferases, lyases, ligases, receptors, receptor ligands, cytokines, antibodies, immunomodulatory molecules, signalling molecules, fluorescent proteins and proteins with insecticidal or biocidal activities. Useful general classes of enzymes include, but are not limited to, proteases, cellulases, lipases, hemicellulases, laccases, amylases, glucoamylases, esterases, lactases, polygalacturonases, galactosidases, ligninases, oxidases, peroxidases, glucose isomerases, nitrilases, hydroxylases, polymerases and depolymerases. In addition to enzymes, the encoded proteins which can be used in this invention include, but are not limited to, transcription factors, antibodies, receptors, growth factors (any of the PDGFs, EGFs, FGFs, SCF, HGF, TGFs, TNFs, insulin, IGFs, LIFs, oncostatins, and CSFs), immunomodulators, peptide hormones, cytokines, integrins, interleukins, adhesion molecules, thrombomodulatory molecules, protease inhibitors, angiostatins, defensins, cluster of differentiation antigens, interferons, chemokines, antigens including those from infectious viruses and organisms, oncogene products, thrombopoietin, erythropoietin, tissue plasminogen activator, and any other biologically active protein which is desired for use in a clinical, diagnostic or veterinary setting. All of these proteins are well defined in the literature and are so defined herein. Also included are deletion mutants of such proteins, individual domains of such proteins, fusion proteins made from such proteins, and mixtures of such proteins; particularly useful are those which have increased half-lives and/or increased activity.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides containing in co- and/or post-translational modifications of the polypeptide made in vivo or in vitro, for example, glycosylations, acetylations, phosphorylations, PEGylations and sulphations. In addition, protein fragments, analogs (including amino acids not encoded by the genetic code, e.g. homocysteine, ornithine, p-acetylphenylalanine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

"Amino acids" or "amino acid residues" may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Sequence variants" refers to variants of discrete biopolymers (that is biopolymers whose sequence can be uniquely defined) including polynucleotide and polypeptide and variants. Sequence variants are sequences that are related to one another or to a common nucleic acid or amino acid "reference sequence" but contain some differences in nucleotide or amino acid sequence from each other. These changes can be transitions, transversions, conservative substitutions, non-conservative substitutions, deletions, insertions or substitutions with non-naturally occurring nucleotides or amino acids (mimetics). The phrase "optimizing a sequence" refers to the process of creating nucleic acid or protein variants so that the desired functionality and or properties of the protein or nucleic acid are improved. One of skill will realize that optimizing a protein or nucleic acid could involve selecting a variant with lower functionality than the parental protein if that is desired.

The term "antibody" as used herein includes antibodies obtained from both polyclonal and monoclonal preparations, as well as: hybrid (chimeric) antibody molecules (see, for example, Winter et al. (1991) Nature 349:293-299; and U.S. Pat. No. 4,816,567); F(ab')2 and F(ab) fragments; Fv molecules (noncovalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, for example, Huston et al. (1988) Proc Natl Acad Sci USA 85:5879-5883); dimeric and trimeric antibody fragment constructs; minibodies (see, e.g., Pack et al. (1992) Biochem 31:1579-1584; Cumber et al. (1992) J Immunology 149B:120-126); humanized antibody molecules (see, for example, Riechmann et al. (1988) Nature 332:323-327; Verhoeyan et al. (1988) Science 239:1534-1536; and U.K. Patent Publication No. GB 2,276,169, published Sep. 21, 1994); and, any functional fragments obtained from such molecules, wherein such fragments retain specific-binding properties of the parent antibody molecule.

The term "sequence alignment" refers to the result when at least two biopolymer sequences are compared for maximum correspondence, as measured using a sequence comparison algorithms. Optimal alignment of sequences for comparison can be conducted by any technique known or developed in the art, and the invention is not intended to be limited in the alignment technique used. Exemplary alignment methods include the local homology algorithm of Smith & Waterman, Adv. Appl. Math. 2:482 (1981), the homology alignment algorithm of Needleman & Wunsch, J. Mol. Biol. 48:443 (1970), the search for similarity method of Pearson & Lipman, Proc. Nat'l. Acad. Sci. USA 85:2444 (1988), by computerized implementations of these algorithms (e.g., GAP, BESTFIT, FASTA, and TFASTA in the Wisconsin Genetics Software Package, Genetics Computer Group, 575 Science Dr., Madison, Wis.), and by inspection.

The "three dimensional structure" of a protein is also termed the "tertiary structure" or the structure of the protein in three dimensional space. Typically the three dimensional structure of a protein is determined through X-ray crystallography and the coordinates of the atoms of the amino acids determined. The coordinates are then converted through an algorithm into a visual representation of the protein in three dimensional space. From this model, the local "environment" of each residue can be determined and the "solvent accessibility" or exposure of a residue to the extraprotein space can be determined. In addition, the "proximity of a residue to a site of functionality" or active site and more specifically, the "distance of the α or β carbons of the residue to the site of functionality" can be determined. For glycine residues, which lack a β carbon, the α carbon can be substituted. Also from the three dimensional structure of a protein, the residues that "contact with residues of interest" can be determined. These would be residues that are close in three dimensional space and would be expected to form bonds or interactions with the residues of interest. And because of the electron interactions across bonds, residues that contact residues in contact with residues of interest can be investigated for possible mutability. Additionally, nuclear magnetic resonance spectroscopy can be used to determine the structure. Additionally, molecular modeling can be used to determine the structure, and can be based on an homologous structure or ab initio. Energy minimization techniques can also be employed.

Although not dependent on three dimensional space, the "residue chemistry" of each amino acid is influenced by its position in a protein. "Residue chemistry" refers to characteristics that a residue possesses in the context of a protein or by itself. These characteristics include, but are not limited to, polarity, hydrophobicity, net charge, molecular weight, propensity to form a particular secondary structure, and space filling size.

As used herein, the term "carrier" refers to a diluent, adjuvant, excipient, or vehicle. Carriers can be liquids, such as water and oils, including those of petroleum, animal, vegetable or synthetic origin, such as peanut oil, soybean oil, mineral oil, sesame oil and the like. The vehicles (e.g., pharmaceutical vehicles) can be saline, gum acacia, gelatin, starch paste, talc, keratin, colloidal silica, urea, and the like. In addition, auxiliary, stabilizing, thickening, lubricating and coloring agents can be used. When administered to a patient, the carriers are preferably sterile. Water can be the carrier when composition is administered intravenously. Saline solutions and aqueous dextrose and glycerol solutions can also be employed as liquid vehicles, particularly for injectable solutions. Suitable vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. Compositions, if desired, can also contain minor amounts of wetting or emulsifying agents, or pH buffering agents.

An expert system 100 is computer program that represents and reasons with the knowledge of some specialist subject (biopolymers) with a view to solving problems or giving advice (via rank ordering of substitutions with reasoning)

Knowledge acquisition is the transfer and transformation of potential problem-solving expertise (e.g. knowledge of analysing nucleotide or protein structure, nucleotide or protein phylogeny) from the knowledge source to a program.

Knowledge base 108 is the encoded knowledge for an expert system 100. In a rule-based expert system 100, a knowledge base 108 typically incorporates definitions of attributes and rules along with control information.

An inference engine 106 is software that provides the reasoning mechanism in expert system 100. In a rule based expert system 100, it typically implements forward chaining and backward chaining strategies.

A biopolymer is a molecule formed by the covalent linkage of repeating units of similar structures. Examples include, but are not limited to, polynucleotides, polypeptides, polysaccharides, lipids, polyketides and terpenes. Following their initial synthesis, a biopolymer can be additionally modified for example by glycosylation, PEGylation, methylation, hydroxylation, dehydration, oxidation and cyclization. Such modifications are included within the scope of the present invention. The sequence of a biopolymer is a linear description of the composition of that biopolymer. For example for a polynucleotide it is a description of the order of covalent linkage of nucleotide bases, for a polypeptide it is a description of the order of covalent linkage of amino acids, for a polyketide it is a description of the order of covalent linkage of ketide moieties etc. For the purposes of this invention, the term sequence may optionally also include a description of residues that are modified subsequent to their incorporation into the biopolymer, for example modifications of tRNA bases such as methylation of uracil, modifications of protein amino acids such as glycosylation, modifications of polyketide residues such as methylation or glycosylation and so on.

A substitution in a biopolymer is the replacement of one monomer with a different monomer.

A virtual surrogate screen is a measure of the activity of a biopolymer in dimensions that are mathematically constructed from physical measurements of biopolymer properties in two or more assays.

The terms screen, assay, test and measurement are used interchangeably to mean a method of determining one or more property of a biopolymer.

A high throughput screen, assay, test or measurement is used to describe any method for determining one or more property of a plurality of biopolymers either sequentially of simultaneously. The actual number of biopolymer variants whose properties can be determined by a test that is considered a high throughput screen varies from as few as 84 samples per day (Decker et al., 2003, Appl Biochem Biotechnol 105: 689-703.) to many millions. For the purposes of this invention we define a high throughput screen as an assay that can measure one or more biopolymer property for 400 biopolymer variants in 1 week, preferably a test that can measure one or more biopolymer property for 1,000 biopolymer variants in 1 week, more preferably a test that can measure one or more biopolymer properties for 10,000 biopolymer variants in one week.

As used herein the term "functional domain" means a segment of a protein that has one or more of the following properties (i) a structurally independent section of a protein, (ii) a section of a protein that is homologous to a section of another protein, (iii) a segment of protein involved in one or more specific functions, (iv) an independently evolving unit in a protein, (v) a segment of protein containing a particular sequence motif, (vi) a section of the protein containing an active site, a binding site or a regulatory site. See, for example, Suhail A Islam, Jingchu Luo and Michael J E Sternberg, 1995, "Identification and analysis of domains in proteins," Protein Engineering 8, 513-525; Orengo et al., 1997, "CATH—A Hierarchic Classification of Protein Domain Structures," Structure 5, 1093-1108; and Pearl et al., 2000, "Assigning genomic sequences to CATH," Nucleic Acids Research 28, 277-282, which are each hereby incorporated by reference in their entirety.

In some embodiments, the term "substitution" means a substitution of a residue in a polymer from one residue type to another residue type. For instance, a change from alanine to phenylalanine at position 100 in a biopolymer of interest is a substitution. A change from guanine to cytosine at position 10 in an oligomer is a substitution.

5.8 Synthesis of Biopolymer Sequence Variants

Biopolymer variants can be synthesized by methods for constructing or obtaining specific nucleic acid or polypeptide or polyketide sequences described in the art. Biopolymer variants are designed, for example, in step 03 of FIG. 2, as described in Section 5.2, above.

Oligonucleotides and polynucleotides may be synthesized using a variety of chemistries including phosphoramidite chemistry; optionally this synthesis may be performed using a commercially available DNA synthesizer. Oligonucleotides and polynucleotides may also be purchased from a commercial supplier of synthetic DNA.

Chemically synthesized oligonucleotides may be incorporated into larger polynucleotides to create one or more of the designed sequence variants using site-directed mutagenesis. Suitable site-directed techniques include those in which a template strand is used to prime the synthesis of a complementary strand lacking a modification in the parent strand, such as methylation or incorporation of uracil residues; introduction of the resulting hybrid molecules into a suitable host strain results in degradation of the template strand and replication of the desired mutated strand. See (Kunkel, 1985, Proc Natl Acad Sci USA 82: 488-92.); QuikChange™ kits available from Stratagene, Inc., La Jolla, Calif. PCR methods for introducing site-directed changes can also be employed. Site-directed mutagenesis using a single stranded DNA template and mutagenic oligos is well known in the art (Ling & Robinson 1997, Anal Biochem 254:157 1997). It has also been shown that several oligos can be incorporated at the same time using these methods (Zoller 1992, Curr Opin Biotechnol 3: 348). Single stranded DNA templates are synthesized by degrading double stranded DNA (Strandase™ by Novagen). The resulting product after strain digestion can be heated and then directly used for sequencing. Alternatively, the template can be constructed as a phagemid or M13 vector. Other techniques of incorporating mutations into DNA are known and can be found in, e.g., Deng et al. 1992, Anal Biochem 200:81.

Multiple chemically synthesized oligonucleotides may together be assembled into larger polynucleotides to create one or more of the designed sequence variants. Oligonucleotides may be assembled into larger single- or double-stranded polynucleotides in vivo or in vitro by a variety of methods including but not limited to annealing, restriction enzyme digestion and ligation, particularly using restriction enzymes whose cleavage site is distinct from their recognition sites (see for example Pierce 1994, Biotechniques 16:708-15; Mandecki & Bolling 1988, Gene 68:101-7), ligation (see for example Edge at al 1981, Nature 292:756-62; Jayaraman & Puccini 1992 Biotechniques 12:392-8), ligation followed by polymerase chain reaction amplification (see for example Jayaraman et al 1991, Proc Natl Acad Sci USA. 88:4084-8), overlap extension using thermostable nucleotide polymerases and/or ligases (see for example Ye et al 1992, Biochem Biophys Res Commun. 186:143-9; Horton et al 1989 Gene. 77:61-8; Stemmer et al 1995 Gene. 164:49-53), dual asymmetric PCR (see for example Sandhu et al 1992, Biotechniques 12:14-6) stepwise elongation of sequences (see for example Majumder 1992, Gene. 110:89-94), the ligase chain reaction (see for example Au et al 1998, Biochem Biophys Res Commun. 248:200-3; Chalmers & Curnow 2001, Biotechniques 30:249-52), insertional mutagenesis (see for example Ciccarelli et al 1990 Nucleic Acids Res. 18:1243-8), the exchangeable template reaction (see Khudyakov et al 1993, Nucleic Acids Res. 21:2747-54), sequential ligation of one or more oligonucleotides to an anchored oligonucleotide (for example a biotinylated oligonucleotide immobilized on streptavidin resin), cotransformation into an appropriate host cell such as mammalian, yeast or bacterial cells capable of joining polynucleotides (see for example Raymond et al 1999, BioTechniques 26: 134-141), or any combination of steps involving the activity of one or more of a polymerase, a ligase, a restriction enzyme, and a recombinase. Oligonucleotides may optionally be designed to improve their assembly into larger polynucleotides and subsequent processing, for example by optimizing annealing properties and eliminating restriction sites (see for example Hoover & Lubkowski 2002, Nucleic Acids Res. 30:e43).

Synthesis of polynucleotide sequence variants can also be multiplexed. Individual variants can subsequently be identified, for example by picking and sequencing single clones. Other methods of deconvolution include testing for an easily measured phenotype (examples include but are not limited to colorigenic, fluorigenic or turbidity-altering reactions that can be visualized on agar plates), then grouping clones according to activity and selecting one or more clone from each group. Optionally the one or more clone from each group may be sequenced.

One example of multiplexed variant synthesis is to incorporate one or more oligonucleotides containing one or more alternative nucleotide substitutions into one or more polynucleotide reference sequences simultaneously. Oligonucleotides synthesized from mixtures of nucleotides can be used. The synthesis of oligonucleotide libraries is well known in the art. In one alternative, degenerate oligos from trinucleotides can be used (Gaytan et al., 1998, Chem Biol 5:519; Lyttle et al. 1995, Biotechniques 19:274; Virnekas et al., 1994, Nucl. Acids Res 22:5600; Sondek & Shortle 1992, Proc. Natl. Acad. Sci. USA 89:3581). In another alternative, degenerate oligos can be synthesized by resin splitting (Lahr et al., 1999, Proc. Natl. Acad. Sci. USA 96:14860; Chatellier et al., 1995, Anal. Biochem. 229:282; and Haaparanta & Huse, 1995, Mol Divers 1:39). Mixtures of individual primers for the substitutions to be introduced by site directed mutagenesis can be simultaneously employed in a single reaction to produce the desired combinations of mutations. Simultaneous mutation of adjacent residues can be accomplished by preparing a plurality of oligonucleotides representing the desired combinations. In an alternative embodiment, sequences are assembled using PCR to link synthetic oligos (Horton et al., 1989, Gene 77:61; Shi et al. 1993, PCR Methods Appl. 3:46; and Cao, 1990, Technique 2:109). PCR with a mixture of mutagenic oligos can be used to create a multiplexed set of sequence variants that can subsequently be deconvoluted.

Cassette mutagenesis can also be used in creating multiple polynucleotide sequence variants. Using this technique, a set of sequences can be generated by ligating fragments obtained by oligonucleotide synthesis, PCR or combinations thereof. Segments for ligation can, for example, be generated by PCR and subsequent digestion with type II restriction enzymes. This enables introduction of mutations via the PCR primers. Furthermore, type II restriction enzymes generate non-palindromic cohesive ends which significantly reduce the likelihood of ligating fragments in the wrong order. Techniques for ligating many fragments can be found in Berger et al., Anal Biochem 214:571 (1993).

Protein variants can be synthesized as nucleic acid sequence variants according to any of the processes described here, followed by expression either in vivo or in an in vitro cell-free system. They may also be made directly using commercial peptide synthesizers. Protein variants may additionally be synthesized by chemically ligating one or more synthetic peptides to one or more polypeptide segments created by expression of a polynucleotide (see for example Pal et al. 2003 Protein Expr Purif. 29:185-92).

Protein variants may optionally include non-natural amino acids, incorporated at specific positions in the protein sequence by a variety of methods (see for example Hyun Bae et al 2003, J Mol Biol. 328:1071-81; Hohsaka & Sisido 2002, Curr Opin Chem Biol. 6:809-15; Li and Roberts 2003, Chem. Biol 10:233-9).

Methods for creating polyketide sequence variants are known in the art (see for example Leadley (1997) Curr Opin Chem Biol. 1:162-8). One such method is to combine polyketide synthase subunits (for example type 1 modular polyketide synthase subunits) whose combined activity is to produce a polyketide macrolactone. In one embodiment polynucleotides encoding different polyketide synthase subunits may be provided to a host cell in compatible vectors (see for example Que et al (1999) Proc Natl Acad Sci USA. 96:11740-5). In another embodiment, polynucleotide(s) encoding one or more tailoring enzymes (including glycosyl transferases and sugar synthesis pathways (see for example Tang & McDaniel (2001) Chem Biol. 8:547-55), methyl transferases, hydroxylases) may optionally be included to effect further sequence modifications of the polyketide.

The particular chemical and/or molecular biological methods used to construct the biopolymer sequence variants are not critical; any method(s) which provide the desired sequence variants can be used.

5.9 Representative Tests for Biopolymer Function

Section 5.2 described how a designed set of biopolymer variants was designed. This set of biopolymers is then synthesized using, for example, the techniques described in Section 5.8. Then the biopolymers are tested for relevant biological activity and/or biopolymer properties. A consideration of what a relevant biopolymer property is a case specific exercise. Non-limiting examples of biopolymer properties that can be relevant in some embodiments of the present invention include, but are not limited to, antigenicity, immunogenicity, immunomodulatory activity, catalysis of a chemical reaction, catalysis of polymer synthesis, catalysis of polymer degradation, catalysis of a reaction that separates or resolves two or more chiral compounds, specific activity, thermostability, pH optimum, reduction of viral titer, stimulation or agonism of a signaling pathway, inhibition or antagonism of a signaling pathway, expression of the biopolymer in a homologous host, expression of the biopolymer in a heterologous host, expression of the biopolymer in a plant cell, susceptibility of the biopolymer to in vitro post-translational modifications and susceptibility of the biopolymer to in vivo post-translational modifications.

Of particular relevance for this invention are biopolymer properties whose measurements are intensive in their use of such resources as time, space, equipment and experimental animals. Such characterizations can be rate limiting for empirical-based protein engineering approaches such as those methods applying directed evolution or screening libraries produced by other methods. A common solution to this limitation is to develop a high-throughput screen. See, for example, Olsen et al., 2000, Curr Opin Biotechnol 11:331-7.

High throughput screens typically do not measure the complex combination of functions that are desired in the final engineered biopolymer. High throughput screens can be used to measure some properties of the biopolymer, and the method of this invention allows the properties measured in two or more of these high throughput screens to be combined and used to create a virtual surrogate screen for the properties of interest. High throughput screens that may be used to measure potentially relevant biopolymer properties include but are not limited to: enzyme complementation technology (Graham et al., 2001, J Biomol Screen 6: 401-11.), fluorogenic or chromogenic reactions which may be visualized spectrophotometrically (Schwaneberg et al., 2001, J Biomol Screen 6: 111-7.; Schmidt et al., 2003, Appl Environ Microbiol 69: 297-303; Waslidge et al., 1995, Anal Biochem 231: 354-8.; Kassack et al., 2002, J Biomol Screen 7: 233-46.), by flow cytometry (Daugherty et al., 2000, J Immunol Methods 243: 211-27.; Georgiou, 2000, Adv Protein Chem 55: 293-315.; Olsen et al., 2000, Curr Opin Biotechnol 11: 331-7.) and by solid phase digital imaging (Joo et al., 1999, Chem Biol 6: 699-706.; Joern et al., 2001, J Biomol Screen 6: 219-23.), computational and cellular immunogenicity assays (Tangri et al., 2002, Curr Med Chem 9: 2191-9.), fluorescence anisotropy (Turconi et al., 2001, J Biomol Screen 6: 275-90.), flow cytometry, scintillation proximity (Jenh et al., 1998, Anal Biochem 256: 47-55.; Skorey et al., 2001, Anal Biochem 291: 269-78.) or magnetic bead capture (Yeung et al., 2002, Biotechnol Prog 18: 212-20.) for measurement of surface density or binding affinity or avidity, cell surface display (Kim et al., 2000, Appl Environ Microbiol 66: 788-93.), protein interaction measured by induction of recombination (Kaczmarczyk et al., 2003, Nucleic Acids Res 31: e86.), filter paper assays for detection of cellulase activity (Decker et al., 2003, Appl Biochem Biotechnol 105: 689-703.), fluorescence polarization assays for measuring protein phosphorylation or other cellular components (Parker et al., 2000, J Biomol Screen 5: 77-88.; Allen et al., 2002, J Biomol Screen 7: 35-44.; Kristjansdottir et al., 2003, Anal Biochem 316: 41-9.), assays that link cellular survival or growth to protein activity (Luthi et al., 2003, Biochim Biophys Acta 1620: 167-78.), assays that couple a reaction to a colorimetric or fluorimetric assay including two-hybrid or three-hybrid systems (Young et al., 1998, Nat Biotechnol 16: 946-50.; Baker et al., 2002, Proc Natl Acad Sci USA 99: 16537-42.), assays that measure incorporation of a chromogenic or fluorogenic substrate into a polymer (Glick et al., 2002, Biotechniques 33: 1136-42, 1144.), electrospray and matrix adsorption laser desorption mass spectrometry (LC-MS and MALDI) for detection of small molecules and biopolymers (Jankowski et al., 2001, Anal Biochem 290: 324-9.; Raillard et al., 2001, Chem Biol 8: 891-8.), high performance liquid chromatography (HPLC), enzyme-linked immunosorbent assays (Fahey et al., 2001, Anal Biochem 290: 272-6.; Mallon et al., 2001, Anal Biochem 294: 48-54.), detection of markers for cellular differentiation (Sottile et al., 2001, Anal Biochem 293: 124-8.), induction of a reporter gene in vivo or in vitro (Thompson et al., 2000, Toxicol Sci 57: 43-53.), small molecule or protein binding competition assays (Warrior et al., 1999, J Biomol Screen 4: 129-135.; McMahon et al., 2000, J Biomol Screen 5: 169-76.) and time resolved fluorescence (Zhang et al., 2000, Anal Biochem 281: 182-6.).

Screens for lipase or esterase activities may be performed using colorimetric or chromogenic substrates. Protein variants can be tested for hydrolysis of several different substrates intended to provide a preliminary map of the sequence-activity relationship. Two properties may be of particular interest: the effect of substrate chain length and substrate stereochemistry upon rate of hydrolysis. Commercially available substrates have been used in previous studies of cutinases or other lipases or esterases. Colorimetric screens using p-nitrophenyl acetate (Moore et al. (1996) Nat Biotechnol 14: 458-67.), p-nitrophenyl butyrate, p-nitrophenylcaprylate and p-nitrophenyl palmitate (Yang et al. (2002) Protein Eng 15: 147-52.) have been used to explore chain-length specificity. Colorimetric or fluorimetric screens using (R)- and (S)-enantiomers of p-nitrophenyl-3-butyrate (Koga et al. (2003) J Mol Biol 331: 585-92.), p-nitrophenyl-2-methyldecanoic acid (Liebeton et al. (2000) Chem Biol 7: 709-18.) and resorufin esters of 3-phenylbutyric acid (Henke et al. (1999) Biol Chem 380: 1029-33.) and p-nitrophenyl N-dodecanoyl-D(L)-phenylalaninates (Yano et al. (2003) J Org Chem 68: 1314-8.) have been used to explore esterase enantioselectivity. New fluorogenic triacylglycerol analogs have also been developed to determine chain length and enantioselectivity of lipases and cutinases (Zandonella et al. (1995) Eur J Biochem 231: 50-5.; Duque et al. (1996) J Lipid Res 37: 868-76.; Zandonella et al. (1996) Chirality 8: 481-89.; Hermetter (1999) Methods Mol Biol 109: 19-29.). Qualitative measurement of esterase activities can also be performed when bacteria expressing active esterases are grown on agar plates containing substrates (such as vinyl esters (Chahinian et al. (2002) Lipids 37: 653-62.), t-butyl esters (Yeo et al. (1998) J Gen Appl Microbiol 44: 147-152.) and 3-(aryloxy)-1,2-propanediol derivatives (Tomic et al. (2002) J Mol Graph Model 21: 241-52.)). In this case, hydrolysis is detected by a decrease in the pH of the medium (Griswold (2003) Methods Mol Biol 230: 203-11.). A set of at least 6 substrates including at least 1 enantiomeric pair will be selected from the substrates listed for which hydrolysis by the wild-type cutinase can be detected. The cutinase variant set will then be tested for activity against these same substrates using standard colorimetric or fluorimetric assays.

Other properties can be easily measured in high throughput screens and are of particular relevance to therapeutic proteins including antibodies, immunoconjugates, transcription factors, antibodies, receptors, growth factors (any of the PDGFs, EGFs, FGFs, SCF, HGF, TGFs, TNFs, insulin, IGFs, LIFs, oncostatins, and CSFs), immunomodulators, peptide hormones, cytokines, integrins, interleukins, adhesion molecules, thrombomodulatory molecules, protease inhibitors, angiostatins, defensins, cluster of differentiation antigens, interferons, chemokines, antigens including those from infectious viruses and organisms, oncogene products, thrombopoietin, erythropoietin, tissue plasminogen activator, and any other biologically active protein which is desired for use in a clinical, diagnostic or veterinary setting, although they may also have application to other protein applications. These screens include measurements of cell lines and primary cell cultures for cell-surface receptor surface density, measurements of cell surface receptor internalization rates, cell surface receptor post-translational modifications including phosphorylation, [Carthanan], binding of antigens including but not limited to cellular growth factor receptors, receptors or mediators of tumor-driven angiogenesis, B cell surface antigens and proteins synthesized by or in response to pathogens, induction of antibody-mediated cell killing, antibody-dependent macrophage activity, histamine release, induction of or cross-reaction with anti-idiotype antibodies, Examples of biopolymer properties or activities whose measurement may be resource, time or cost-limited and that therefore cannot be accurately measured in high throughput are tests for the immunogenicity of a biopolymer, in vivo or cell-culture based viral titer measurements, any experiment in which an experimental animal or human being is used as a part of the measurement of one or more properties of the biopolymer, the level of expression of the biopolymer in a host, any experiment in which the biopolymer is produced within a plant particularly when the plant must be transformed with a polynucleotide encoding the biopolymer and the biopolymer be expressed within the plant, susceptibility of the biopolymer to be modified inside a living cell, susceptibility of the biopolymer to be modified not inside a living cell, measurement of the chirality of one or more compounds produced as a result of the activity of the biopolymer, measurement of the composition of a complex mixture of compounds whose composition has been altered by the action of the biopolymer, measurement of the localization of a biopolymer within a cell or a part of a cell including the nucleus or chromosome of a cell, measurement of the pH optimum of a biopolymer, measurement of the synthesis of a polymer resulting from the action of a biopolymer, measurement of the degradation of a polymer resulting from the action of a biopolymer and the products of that degradation, alteration of the properties of a cell for example alteration of the growth, replication or differentiation patterns of a cell or population of cells, therapeutic efficacy of an antibody and modulation of a signaling pathway.

Technological advances in the future may make it possible to measure in higher throughput properties that can currently be measured only in low throughput. One skilled in the art will readily see that the methods of this invention may be used to correlate any biopolymer properties that are not easily measured with a high-throughput assay with other properties that are readily measured in high throughput.

5.10 Kits

The invention provides kits comprising a set of variant or a single variant in a set of variants that have been refined by the apparatus and methods describe herein.

The invention also provides a pharmaceutical pack or kit comprising one or more containers filled with a variant of set of variants of the present invention. The pharmaceutical pack or kit may further comprise one or more other prophylactic or therapeutic agents useful for the treatment of a particular disease. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.11 Articles of Manufacture

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures (such as methods for monitoring mean absolute lymphocyte counts, tumor cell counts, and tumor size) and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material.

In a specific embodiment, an article of manufacture comprises packaging material and a pharmaceutical agent and instructions contained within said packaging material, wherein said pharmaceutical agent is a humanized antibody and a pharmaceutically acceptable carrier, and said instructions indicate a dosing regimen for preventing, treating or managing a subject with a particular disease. In another embodiment, an article of manufacture comprises packaging material and a pharmaceutical agent and instructions contained within said packaging material, wherein said pharmaceutical agent is a humanized antibody, a prophylactic or therapeutic agent other than the humanized antibody and a pharmaceutically acceptable carrier, and said instructions indicate a dosing regimen for preventing, treating or managing a subject with a particular disease. In another embodiment, an article of manufacture comprises packaging material and two pharmaceutical agents and instructions contained within said packaging material, wherein said first pharmaceutical agent is a humanized antibody and a pharmaceutically acceptable carrier and said second pharmaceutical agent is a prophylactic or therapeutic agent other than the humanized antibody, and said instructions indicate a dosing regimen for preventing, treating or managing a subject with a particular disease.

The present invention provides that the adverse effects that may be reduced or avoided by the methods of the invention are indicated in informational material enclosed in an article of manufacture for use in preventing, treating or ameliorating one or more symptoms associated with a disease. Adverse effects that may be reduced or avoided by the methods of the invention include but are not limited to vital sign abnormalities (e.g., fever, tachycardia, bardycardia, hypertension, hypotension), hematological events (e.g., anemia, lymphopenia, leukopenia, thrombocytopenia), headache, chills, dizziness, nausea, asthenia, back pain, chest pain (e.g., chest pressure), diarrhea, myalgia, pain, pruritus, psoriasis, rhinitis, sweating, injection site reaction, and vasodilatation. Since some of the therapies may be immunosuppressive, prolonged immunosuppression may increase the risk of infection, including opportunistic infections. Prolonged and sustained immunosuppression may also result in an increased risk of developing certain types of cancer.

Further, the information material enclosed in an article of manufacture can indicate that foreign proteins may also result in allergic reactions, including anaphylaxis, or cytosine release syndrome. The information material should indicate that allergic reactions may exhibit only as mild pruritic rashes or they may be severe such as erythroderma, Stevens Johnson syndrome, vasculitis, or anaphylaxis. The information material should also indicate that anaphylactic reactions (anaphylaxis) are serious and occasionally fatal hypersensitivity reactions. Allergic reactions including anaphylaxis may occur when any foreign protein is injected into the body. They may range from mild manifestations such as urticaria or rash to lethal systemic reactions. Anaphylactic reactions occur soon after exposure, usually within 10 minutes. Patients may experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, or eosinophilia.

6. EXAMPLES

6.1 Engineering a Protein (Proteinase K) Using Expert Substitution Selection Methods and Sequence-Activity Relationships The design, synthesis and analysis of sequence variants of proteinase K is described here as an example of the use of sequence-activity relationships to engineer desired properties into a protein. Also described is the analysis of these variants using six different functional tests, and methods for determining components of a virtual screen.

FIG. 8 shows the amino acid sequence of proteinase K that occurs naturally in the fungus *Tritirachium album* Limber (Gunkel et al. (1989) Eur J Biochem 179: 185-194) (SEQ ID NO.: 2) together with an *E. coli* leader peptide (SEQ ID NO.: 1). FIG. 9 shows a nucleotide sequence designed to encode proteinase K (SEQ ID NO.: 3). The sequence has been modified from the original *Tritirachium album* sequence by removing an intron, adding an *E. coli* leader peptide and altering the codons used to resemble the distribution found in the highly expressed genes of *E coli*. The gene was synthesized for the natural proteinase K from oligonucleotides.

Several different criteria were used to identify positions and substitutions to make in the proteinase K sequence as detailed below

6.1.1 Principal Component Analysis to Identify Substitutions that may Contribute to Thermostability The proteinase K gene was used as probe against GENBANK using BLAST based algorithms. A BLAST score was chosen as a cut-off that identified more than ten but less than one hundred related sequences. This search identified the 49 sequences identified in FIG. 10.

The sequences (49 rows×728 variables) were represented in a Free-Wilson method of qualitative binary description of monomers (Kubinyi, 3D QSAR in drug design theory methods and applications. Pergamon Press, Oxford, 1990, pp 589-638), and distributed in a maximally compressed space using principal component analysis so that the first principal component (PC) captured 10.8 percent of all variance information (eigenvalue of 79), the second principal component (PC) captured 7.8 percent of all variance information (eigenvalue of 57), the third principal component (PC) captured 6.9 percent of all variance information (eigenvalue of 50), the fourth principal component (PC) captured 6.2 percent of all variance information (eigenvalue of 45), the fifth principal component (PC) captured 5.4 percent of all variance information (eigenvalue of 39) and so on until $728^{th}$ principal component (PC) captured 0 percent of all variance information (Eigenvalue 0).

All sequences were plotted in the first six principal components, which captured a total of 42 percent of all variance information present in the 728 dimensions. Sequences 46, 47, 48, 49 are all derived from thermophilic organisms and are all well separated from the proteinase K homologs 1-45 in both of the first two principal components, as shown in FIG. 11.

A corresponding plot of all loads describes the influence of each variable on the sample distribution in the various. PCs. The correlation between loads (influence of variables—in this case amino acid residues) and score (distribution of samples—here proteinase K homologs) illustrates graphically which residues are unique in determining the phylogenetic separation of genes 46-49 from genes 1-45. This is shown in FIG. 12.

Subsequently, the lower left corner of the bottom left quadrant of the loads plot was magnified and the variables labeled (FIG. 13). By adding the PC1 and PC2 value for each variable one can rank order the influence of each residue for their reciprocal effect on sample distribution. This distribution of residue effects can be due to common ancestral history or can be due to functional constraints among this group of samples.

As can be seen in FIG. 13, residues that are completely co-evolving (due to sampling effects, phylogenetic ancestry or other) will have the exact same load and consequently collapse the variable space in as many dimensions as there are absolute coevolving residues. This is illustrated in the graph where residues 15D, 18D, 19Q, 22L, 23P, 65Y, 66D, 110R, 137P, 164D, 189C, 198R all are completely co-evolving and all have profound effect on the distribution of samples 46-49 in PC1 and PC2. After removing residues that are unique for only one of the extreme samples, residues that are common to the thermophiles but unique to one individual were retained and further explored. Variables here can be amino acids as depicted in this example, or any type of feature. Features include, but are not limited to, physico-chemical properties of one or more amino acid residues. The residues can be a block or modulated within the gene, or it can be a combination of residues not genetically linked such as in the example above of residues 15D, 18D, 19Q, 22L, 23P, 65Y, 66D, 110R, 137P, 164D, 189C, 198R.

The loads for the amino acids most responsible for the clustering of thermophilic proteinase K homologs are shown in FIG. 14. This information was then incorporated into knowledge base 108. This is an example of pre-processing information.

6.1.2 Structural Information for Homologous Enzymes

The BLAST search of GENBANK for proteinase K homologs also revealed that proteinase K is homologous to subtilisin and other serine proteases. Subtilisin in particular has been extensively studied. The structures of naturally occurring and variant subtilsins have been obtained, and there is a large body of data regarding the functional effects of a substantial number of mutations. See, for example, Bryan, 2000, Biochim Biophys Acta 1543:203-222. Sequence and structural alignments of proteinase K with subtilisin allowed for the identification of homologous positions in proteinase K having changes known to improve activity or thermostabilize subtilisin. This information was incorporated into the knowledge base 108. This is an example of pre-processing information.

6.1.3 Sequence Information from Thermostable Close Homologs

Amongst the closest ten homologs of proteinase K identified by BLAST search of Genbank, are enzymes known to be thermostable. These enzymes were aligned positions that were conserved between the thermostable homologs but not found in non-thermostable homologs were identified. This information was then incorporated into the knowledge base 108. This is an example of pre-processing information.

6.1.4 Sequence Information from Close Homologs

One of the homologs identified in the BLAST search was highly related to proteinase K (>95% sequence identity) and also thermostable. The sequence of this protein was aligned with proteinase K and all amino acid changes between the two enzymes were identified. This information was then incorporated into the knowledge base 108. This is an example of pre-processing information.

6.1.5 Information Processing

Using the information described above that was placed in knowledge base 108, the following rules 120 were defined.

(a) Changes that are already present in proteinase K were eliminated.

(b) Changes that occur in the pro-region of the protein were eliminated (c) A score proportional to the load from the PCA analysis was added.

(d) A score for conservative changes was added.

(e) A score for changes found in a close homolog (>95% identical) was added.

(f) A score for change found in a close homolog that is thermostable but not in close homologs that are not thermostable was added.

An initial sequence space of 24 residues was defined using rules (a) through (f). Changes with the top 24 scores were picked. These residues are shown in FIG. 15.

These variations and all combinations of these variations encompass a sequence space of over a million different sequences. To reduce the number of variants to test in the first set of variants a design based on prior knowledge and single site statistics considerations was used (FIG. 2, step 03).

Based on information about the plasticity of serine proteases and subtilisin genes, variants with six changes per clone were designed. In this example all of the 24 top-scoring changes were equally represented. In other embodiments, a set of variants that represent each change with a frequency reflecting its actual score could have been designed. In this case, 24 clones were designed that cover the sequence space uniformly. One way to measure the uniformity of the space covered is by counting the number of instances a particular substitution (e.g., N95C) is seen in the 24 clones. This number was set at six for all the variations identified. This means, that in the set of variations synthesized, each of the identified mutations occurs six times. For example, the mutation N95C is found in six of the variants, the mutation P97S is found in six of the variants, and so forth.

The variants defined by this process are listed in FIG. 16, where FIG. 15 serves as the key for FIG. 16. For example, "95 in FIG. 16 means "N95C", "355 in FIG. 16, means "P335S".

The polynucleotides encoding each proteinase K variant defined in FIG. 16 were synthesized by PCR-based assembly of synthetic oligonucleotides. The sequence of each variant was confirmed using an ABI sequencer. The ability of each of these variant proteins to hydrolyze casein was then measured simply to determine whether the proteinase K variants had any protease activity. This is the first step in exploring the sequence space. (FIG. 2, step 04).

This data, as well as data measuring the activity of proteinase K towards the hydrolysis of polylactide, can be used to analyze the data using sequence-activity correlating methods to evaluate the substitutions (steps 05 and 06 of FIG. 2). In turn, this information can be used to update knowledge base 108 and to perform additional iterations of the method to thus further explore the sequence space for improvements in desired properties.

Preliminary data indicated that changes at residues 95, 97, 138, 208, 236, 237, 265 and 299 were found only in poorly performing variants. Changes at residues 123, 145, 167, 273, 293, 310, 332, 337 and 355 were found in medium performing variants. Changes at residues 107, 151, 180, 194, 199 and 267 were found in high performing variants. Using this information the next round of sequence sets was designed and is shown in FIG. 17.

Additionally, from the results of the experiments, expert system 100, in conjunction with the sequence-activity correlating methods inferred that the proline to serine change (seen at positions 97 and 265) for flexibility and structural perturbation twice resulted in disadvantageous changes. This information was coded into the knowledge base 108 for future experiments. This is one illustration of updating knowledge base 108.

The sequence of each constructed variant is shown in FIG. 18. The activity of the variants towards casein, which is a large polymeric substrate like polylactide, was measured. Variant activity towards a modified tetrapeptide, N-succinyl-Ala-Ala-Pro-Leu-p-nitroanilide (AAPL-p-NA) which undergoes a colorimetric change upon protease-mediated hydrolysis (Sroga et al. (2002) Biotechnol Bioeng 78: 761-9), was also measured. Using this substrate, the activity of the variants at three different pH values (7, 5.5 and 4.5) was measured. The activity of variants following a five minute heat treatment at 65° C. was also measured. The activities observed for each property measured are shown in FIG. 19.

For each of the proteinase K activities tested, a partial least squares regression (PLSR) was used to model the relationship between amino acid substitution and proteinase activity (the sequence-activity relationship) for variants 10-49. The application of these methods to nucleic acids, peptides and proteins has been described previously. See, for example, Geladi et al., 1986, Analytica Chimica Acta 186: 1-17; Hellberg et al., 1987, J Med Chem 30: 1126-35.; Eriksson et al., 1990, Acta Chem Scand 44: 50-55; Jonsson et al., 1993, Nucleic Acids Res. 21: 733-739; Norinder et al., 1997, J Pept Res 49: 155-62.; Bucht et al., 1999, Biochim Biophys Acta 1431: 471-82.

The PLSR-based sequence activity model was used to assign a regression coefficient to each varied amino acid. The predicted activity for a proteinase K variant was calculated by summing the regression coefficients for amino acid substitutions that are present in that variant. In this case, terms to account for interactions between the varied amino acids were not included, although this can also be done. See, for example, Aita et al., 2002, Biopolymers 64: 95-105. FIG. 20 shows a correlation between the predictions of the sequence-activity model and the measured ability of heat-treated proteinase K variants to hydrolyze AAPL-p-NA.

The utility of the sequence-activity model was tested for its ability to predict the activity of variants that have not been measured, or to identify amino acid substitutions that contribute positively to a specific protein property and that can then be experimentally combined. To test the sequence activity model for heat-tolerant hydrolyzers of AAPL-p-NA, the regression coefficients from the model were tested, as shown in FIG. 21.

Four of the amino acid changes had been incorporated into the variants were predicted to have a positive effect on the activity of proteinase K after heating. These were K208H, V267I, G293A and K332R. Among the variants synthesized in the initial set of 48, one (NS40) contained three of these changes (V267I, G293A and K332R) and one (NS19) contained the other (K208H). To test the predictive power of our model, a variant (NS56) containing all four of these changes was synthesized and its activity was compared with that of NS19 and NS40.

As shown in FIG. 22, combining the four changes identified by the PLSR model produced a variant with greater post-heat treatment activity towards AAPL-p-NA than the single or triple changes. By synthesizing and measuring the activities of only 48 variants a new variant that was further improved for measured activity was designed. This demonstrates that the combination of low-throughput screening and mathematical analysis is useful for protein engineering.

The current paradigm for empirical protein engineering is to employ high throughput screens to test libraries of thousands of variants. See, for example, Lin et al., 2002, Angew Chem Int Ed Engl 41: 4402-25. In general, high throughput screens do not measure all of the properties that are important for the final application. One common way of overcoming this discrepancy is the use of tiered screens, in which high throughput screens that measure only one or two of the properties of interest are followed by lower throughput screens that more accurately reflect the desired protein characteristics. See, for example, Ness et al., 2000, Adv Protein Chem 55: 261-292. This technique relies on the assumption that the high throughput primary screen will identify the amino acid substitutions that are important for the final function but will also select some false positives. False positives do not actually contribute to the final function and are eliminated by subsequent screens. The alternative possibility, that amino acids that would be beneficial for the final application may be missed by the initial high throughput screen (false negatives), is seldom considered. By prematurely discarding substitutions that would be beneficial for the desired function, the protein engineering process may be unnecessarily prolonged or even fail.

Having measured several properties of the proteinase K variants described above and validated the predictive power of the sequence-activity modeling of the present invention, the validity of the high throughput screening approach was explored in more depth. Although no high throughput screening was explored in this example, all of the assays described above could easily be adapted for use as high throughput primary screens. Hydrolysis of casein incorporated into media plates has been used as a primary screen for protease libraries. See, for example, Ness et al., 1999, Nat Biotechnol 17: 893-896; Ness et al., 2002, Nat Biotechnol 20: 1251-5. Hydrolysis of AAPL-p-NA has also been described. See, for example, Sroga et al., 2002, Biotechnol Bioeng 78: 761-9. Testing AAPL-p-NA hydrolysis at lowered pH (5.5 or 4.5) might be considered an appropriate surrogate for the low pH tolerance that will be required by an enzyme that is producing lactic acid from polylactide. Similarly testing AAPL-p-NA hydrolysis following heat treatment may measure the stability that will be required for an enzyme that must resist the thermal stresses of incorporation into a plastic. Thermostability was expressed in three ways: (i) as the absolute level of activity remaining following heat treatment, (ii) as the activity remaining relative to the activity prior to heat treatment, and (iii) as the product of these two values. Having obtained values for each of these proteinase properties, the correlation between the properties was examine, and the amino acid substitutions that would be selected by each screen were compared.

FIG. 23 shows the distribution of seven proteinase K properties following calculation of the principal components of the activity data (O'Connel (1974) Comp. Phys. Comm. 8: 49). Eighty two percent of the substitution in the data could be captured in just two dimensions. The activities of variants towards AAPL-p-NA at different pHs was highly correlated, as were the different methods of measuring heat tolerance. Thermostability was defined primarily in principal component two (vertical), while substrate preference was differentiated primarily in principal component 1 (horizontal).

Because of the clustering seen in FIG. 23, three representative activities were selected for further analysis: (i) activity towards AAPL-p-NA at pH 7.0, (ii) absolute activity towards AAPL-p-NA following five minutes at 65° C., and (iii) activity towards casein. For each of these activities PLSR models similar to that shown in FIG. 20 were constructed, and the regression coefficients for each amino acid substitution were calculated as shown for thermal tolerance in FIG. 21. The changes calculated to contribute positively to each property are shown in FIG. 24.

The difference between beneficial amino acids selected by the three different representative assays is striking. Use of any of these measurements as the primary assay would select some amino acid changes that are not important for the others. These would be false positives, for example, use of casein hydrolysis as a primary screen would identify six changes (S107D, S123A, V167I, Y194S, A199S and S273T) that have a negative effect on activity towards AAPL-p-NA, with or without heating. Perhaps even more importantly, the casein primary screen would have falsely attributed a negative value to three of the four changes important for thermal tolerance (1(208H, V267I and G293A).

This failure of a tiered screening strategy is not simply a result of selecting an inappropriate surrogate substrate. Similar results would have been seen had activity towards AAPL-p-NA been used as a primary screen followed by a test for thermal tolerance. In this case half of the beneficial changes would still have been discarded as false negatives (K208H and V267I). This analysis shows that measuring properties that are different from those of the final application can result both in incorporation of sequence changes that do not contribute to the desired phenotype, as well as omission of those that do.

A method for engineering proteins based on design, synthesis and testing of small numbers of individual variants followed by mathematical modeling to determine a sequence-activity relationship has been described. Sequence-activity models that can be used predictively to design improved variants have also been described.

By incorporating the principles of experimental design, individual design and synthesis of sequence variants allows a more efficient search of sequence space than a library approach (Hellberg et al. (1991) *Int J Pept Protein Res* 37: 414-424). Another advantage of the modeling approach is that it facilitates empirical protein engineering but requires only very low numbers of variants to be tested. This means that the need for high throughput screens is obviated. This analysis indicates that high throughput and tiered screening can be fundamentally flawed strategies for protein engineering. Both conserved reaction conditions and use of the same substrate appear susceptible to selection of false positives and rejection of false negatives. The performance of high throughput screens will be further compromised when the primary screen is selected on the basis of throughput rather than faithful replication of the final application.

6.2 Designing a Set of Biopolymer Variants to Explore a Sequence Space

Amino acid residues 3-53 of the *H. influenzae* TrmA protein provide an example for the design of a minimal set of variants that can be used to construct a search that captures a maximal amount of information for subsequent use in exploring sequence-activity correlations. Below is an alignment of the TrmA gene (SEQ ID NO.: 4) with seven residues identified as the seven residues most likely to affect the ability of the *H. influenzae* protein to function in a heterologous *E coli* system.

```
LPISQYNELL QKKLEKLTAL LHPFNAPDIQ VFDSPTSHYR
    N      E K         H L          Q

MRAEFRIWHE
    D
```

The amino acid at position seven can be either Q or N, the amino acid at position 15 can be either E or K and so on. The sequence space represented by all possible combinations of these sequences is $2^7=128$ sequences. To search through this space with complete coverage would thus require 128 individually designed and synthesized proteins.

An alternative to synthesizing and testing all possible sequences is to design a set of variants using a Taguchi array. FIG. 25 illustrates a Taguchi array for orthogonal distribution of seven variables, each of which can exist in two different states. Each state for each variable is present in half of the dataset (four proteins), and consequently gets measured four times in different contexts. In addition, every possible pairwise combination of variable states is represented at least once in the dataset so that all two-variable interaction effects on the function of the protein are measured at least once. The contribution from each variable and each two-variable interaction can subsequently be derived using one or more of the sequence-activity correlating methods of this invention. The Taguchi matrix distribution thus allows the design of eight genes to efficiently search through a 128 protein sequence space.

6.3 Identifying a Set of Substitutions to Define a Sequence Space and Designing a Set of Biopolymer Variants to Explore that Sequence Space Celiac Sprue affects as many as one percent of the population of the United States and Europe (Fasano et al., 2003, Arch Intern Med 163: 286-92). The disease causes damage to the villi (microscopic structures of the small intestine), which is associated with severely reduced intestinal absorption of essential nutrients. As a result, patients present with a range of symptoms, including diahhrea, iron and vitamin deficiencies, and reduced bone density. When it occurs in childhood, Celiac Sprue can lead to severe problems such as malabsorption of essential nutrients (such as folic acid, iron, calcium and fat-soluble vitamins) and stunted growth (Green et al., 2003, Lancet 362: 383-91). When onset of the disease occurs later in life, the consequences range from fatigue, anemia and osteoporosis to increased risks of intestinal cancer and lymphomas.

While both genetic and environmental factors play important roles in Celiac Sprue pathogenesis, this disease is uniquely tractable because the environmental trigger has been identified. Gluten proteins, found in most dietary grains such as wheat, rye and barley, have been shown to be the causative agent in inducing Celiac Sprue Exposure to gluten triggers an inflammatory response in celiac patients (Sollid, 1998, Digestive Diseases 16: 345-7), and currently the only treatment for the disease is complete exclusion of gluten from the diet (Murray et al., 2004, Am J Clin Nutr 79: 669-73). Gluten-free diet is a difficult life-long task, and recent studies suggest that even small amounts of gluten (100 ppm) are sufficient to trigger the onset of the disease (Collin et al., 2004, Aliment Pharmacol Ther 19: 1277-83).

While gluten-derived immunostimulatory peptides are not completely cleaved by normal proteases present in the human digestive tract, certain bacterial enzymes have the ability to cleave such proline-rich peptides. One of the best-characterized post-proline cleaving enzymes is the proline endopeptidase from the bacterium *Flavobacterium meningosepticum* (FM PEP) (Diefenthal et al., 1993, Appl. Microbiol. Biotechnol. 40: 90-97). FM PEP is capable of cleaving several gluten-derived peptides that contain T cell epitopes (Shan et al., 2004, Biochem. J. in press). Exposure of gluten to normal digestive enzymes followed by treatment with recombinant FM PEP decreases the number of T cell-stimulating peptides (Marti et al., 2004, submitted for publication). These properties make an enzyme like FM PEP a potential candidate for gluten detoxification and thus for treatment of Celiac Sprue.

Despite this promise, FM PEP does not meet all of the criteria required for a useful gluten detoxification agent. FM PEP has a preference for cleaving bonds between proline and glutamine but does not cleave proline-tyrosine bonds well (Shan et al., 2004, Biochem. J., in press). The products of FM PEP cleavage thus contain a significant fraction of peptides that are 10-20 amino acids in length, and that frequently contain proline-tyrosine dipeptides, a motif which is also present in many T-cell epitopes. As well as failing to cleave all of the potent T cell epitopes, the pH profile of FM PEP is not optimal for the mildly acidic conditions found in upper small intestine (pH range from 6.0 to 6.6 where a potential Celiac Cprue drug should be active (Shan et al., 2004, Biochem. J., in press). Finally, FM PEP does not express well in *E. coli* cells, which would increase the cost of production of drug based on this enzyme (Shan et al., 2004, Biochem. J., in press).

Because of the suboptimal performance of FM PEP, other proly-endopeptidases have been evaluated including one from the bacterium *Myxococcus xanthus* (MX PEP) (Shan et al., 2004, Biochem. J., in press). Preliminary studies show that MX PEP has (i) a higher specific activity against medium-sized (10-20 amino acids) peptides compared to FM PEP, (ii) a moderately improved pH profile (slightly greater acid stability), (iii) the ability to cleave both proline-glutamine and proline-tyrosine bonds (FM has specificity for PQ Bonds) (Shan et al., 2004, Biochem. J., in press).

The MX PEP is still not an ideal candidate gluten-detoxifying Celiac Sprue drug. While it is capable of cleaving many small (<10 amino acids) and medium-sized (10-20 amino acids) T-cell epitopes, it has a lower specific activity against larger gluten-derived peptides such as the 33mer. In addition, the specific activity of this enzyme is approximately 2-fold lower at pH 6.0 (the pH of upper intestine), as compared to pH 7.5.

As is frequently the case with natural proteins to be used as therapeutics, neither of the current candidates is perfectly suited for the task. The desired properties for a prolyl-endopeptidase are well understood and the enzyme is a candidate for optimization by protein engineering. The assay to be used is HPLC analysis of degradation of gluten and gluten-derived immunotoxic peptides. It is feasible to use such screening methods for a small number (<500, preferably <250, more preferably <50 per cycle) but not an overly large number of variants. Methods for identifying useful substitutions and then designing a set of variants representing this sequence space is thus an object of the example.

The *Myxococcus xanthus* prolyl endopeptidase sequence used was the one defined by genetic identifier [gi:4838465] in GENBANK, and accessed by searching for this identifier using the NCBI browser. The following homologs were identified: gi|17131625; gi|24348832; gi|28808634; gi|6048357; gi|4973227; gi|28809898; gi|6460324; gi|216201; gi|27358772; gi|216707; gi|456523; gi|3805974; gi|21727153; gi|4529992; gi|148698; gi|19347837; gi|22946157; gi|1691900; gi|15277538; gi|6456472; gi|6561876; gi|5689035; gi|26343763; gi|5103285; gi|26345256; gi|21040382; gi|164621; gi|9971902; gi|558596; gi|3043760; gi|904214; gi|28502989; gi|17385666; gi|9558588; and gi|15291259.

These sequences (gi:4838465 and the above-identified homologs) were processed and substitutions scored according to a modified version of the scheme shown in FIGS. 3 and 4. The modified process is shown in FIG. 26.

Rule 1a. Align sequences using ClustalW and select all substitutions found in any of the 35 homologs.

Rule 1b. Reconstruct a phylogenetic tree using Clustal W. For each substitution, calculate the evolutionary proximity of the closest homolog in which that substitution occurs. The evolutionary proximity EP is calculated as follows:

$$p = n_d/n$$

where,
p is the p-distance,
$n_d$ is the number of amino acid differences between two sequences; and
n is the total number of amino acids in the protein.
Further, $$d = -\ln(1-p)$$

where,
d is the Poisson-corrected p-distance between two sequences; and
ln(1−p) is the natural logarithm of the p-distance.
And, $$EP = 1/d$$

where,
EP is the evolutionary proximity.

Rule 2b. For each position calculate the site heterogeneity, that is a measure of the number of different amino acids present at that position. The site heterogeneity is calculated as the number of different amino acids seen at a position in the set of homologs (SH).

Rule 3b. For each position calculate the site entropy as follows:

$$SE = -\Sigma\{(P_{Ai}/N) \times \ln(P_{Ai}/N)\}$$

where,
N is the number of homologous sequences,
$P_{Ai}$ is the number of times amino acid i occurs at position P,
$\ln(P_{Ai}/N)$ is the natural log of $P_{Ai}/N$, and
$\Sigma$ is the sum for all amino acids for position P.

Rule 4b. For each substitution, count the number of times it occurs in the set of homologs (SN).

Rule 1c. For each substitution, calculate the favorability of that substitution using a PAM250 matrix:

$$SM = PAM(A_o, A_s)/10$$

where,
$A_o$ is the original amino acid at a position;
$A_s$ is the substitution amino acid,
$PAM(A_o, A_s)$ is a measure of the average probability that $A_o$ is substituted with $A_s$ in a large set of protein homolog families.

As indicated in FIG. 26, the total score is then calculated as:

$$Score = f(EP) \times f(SH) \times f(SE) \times f(SN) \times f(SM)$$

where f( ) is a mathematical function. In this example the function is multiplication by 1, but in principle the use of functions allows different weights to be applied in subsequent cycles.

The results of using this substitution scoring scheme are shown in Table 1 below.

TABLE 1

| Substitution | Score |
| --- | --- |
| F82Y | 0.427376 |
| D225E | 0.427037 |
| V517I | 0.423723 |
| R78K | 0.410195 |
| E276D | 0.408982 |
| S396T | 0.402781 |
| Y550F | 0.397683 |
| D376E | 0.397472 |
| V268I | 0.390803 |
| E9D | 0.379643 |
| D233E | 0.375544 |
| K239R | 0.369665 |
| V628I | 0.365753 |
| E212D | 0.363124 |
| V300I | 0.360761 |
| E261Q | 0.359375 |
| Q10E | 0.356574 |
| W256Y | 0.355259 |
| Q518K | 0.352662 |
| R77K | 0.34542 |
| R345Q | 0.344938 |
| V677I | 0.340269 |
| V554I | 0.339015 |
| Q36K | 0.33743 |
| K52Q | 0.337228 |
| I152M | 0.335877 |
| W126Y | 0.334169 |
| F67Y | 0.3327 |
| E372K | 0.331501 |
| L667M | 0.321891 |

A set of thirty variants were then designed with the following criteria:
1) Include five substitutions in each variant.
2) Require that each substitution occur an equal number of times (5) among variants.
3) Maximize the number of different pairs of substitutions that occur. If each variant contains five substitutions, it contains ten sets of pairs. There is thus a maximum of 300 pairs represented in 300 variants. The variant set shown contains 299 different pairs.

This set was calculated by in silico evolution. An initial set of variants each containing five substitutions was chosen randomly and each substitution occurring five times among variants. Substitutions were then altered randomly. If a change increased the number of substitution pairs in the variant set it was accepted. Otherwise it was rejected. The process continued until 299 different pairs were obtained. The variant set is illustrated in Table 2 below.

TABLE 2

| Variant-1 | R78K | Y550F | V268I | E261Q | K52Q |
|---|---|---|---|---|---|
| Variant-2 | S396T | D233E | V300I | Q36K | F67Y |
| Variant-3 | D225E | V517I | V628I | K52Q | F67Y |
| Variant-4 | D225E | V268I | R77K | V554I | Q36K |
| Variant-5 | S396T | E9D | E212D | W126Y | E372K |
| Variant-6 | R78K | E276D | D376E | D233E | E372K |
| Variant-7 | F82Y | E276D | Y550F | K239R | V628I |
| Variant-8 | D376E | V300I | Q10E | K52Q | L667M |
| Variant-9 | V628I | V300I | R77K | R345Q | W126Y |
| Variant-10 | Y550F | E212D | W256Y | R77K | L667M |
| Variant-11 | E9D | D233E | V628I | V554I | L667M |
| Variant-12 | D376E | V268I | V628I | W256Y | I152M |
| Variant-13 | E212D | Q10E | R345Q | V677I | I152M |
| Variant-14 | F82Y | R78K | W256Y | R345Q | F67Y |
| Variant-15 | F82Y | D225E | V300I | I152M | E372K |
| Variant-16 | F82Y | R78K | V677I | W126Y | L667M |
| Variant-17 | F82Y | E9D | E261Q | Q10E | Q36K |
| Variant-18 | V517I | D233E | E261Q | I152M | W126Y |
| Variant-19 | E276D | E212D | V300I | Q518K | Q36K |
| Variant-20 | V517I | R78K | S396T | Q10E | R77K |
| Variant-21 | S396T | Q518K | V554I | K52Q | I152M |
| Variant-22 | D225E | Y550F | D233E | Q10E | Q518K |
| Variant-23 | D376E | Q518K | R77K | V677I | F67Y |
| Variant-24 | K239R | E212D | E261Q | V554I | F67Y |
| Variant-25 | E276D | S396T | E261Q | W256Y | V677I |
| Variant-26 | K239R | W256Y | Q36K | K52Q | W126Y |
| Variant-27 | V268I | K239R | Q518K | E372K | L667M |
| Variant-28 | V517I | Y550F | V677I | V554I | E372K |
| Variant-29 | D225E | D376E | E9D | K239R | R345Q |
| Variant-30 | V517I | E276D | V268I | E9D | R345Q |

6.4 Identifying a Set of Substitutions and Defining a Set of Variants Representing that Sequence Space for Antibodies with Improved Neutralization of Respiratory Syncitial Virus In this example, the optimization procedures of the present invention are illustrated for an antibody that binds and neutralizes Respiratory Syncytial Virus (RSV). The sequence of one such antibody is publicly available (GENBANK accession #AAF21612). A significant benefit of the computational antibody design system using the methods described in this invention is that only relatively small numbers of variants need to be synthesized and tested. This allows the use of functional tests that are more comprehensive than binding assays. Viral neutralization for example, is an important antibody function but the sequence and structural determinants are poorly understood.

Methods used to identify substitutions in the framework and CDR regions of the heavy chain of the Im-1 antibody sequence are as follows. The sequence of the heavy chain of the Im-1 antibody was aligned using the kabat numbering system with germline human ig heavy chain sequences retrieved from the VBase database. A total of 49 sequences were aligned. This alignment may not limited to germline human sequences. Alternatively, all sequences that are in the same structural class as AAF21612 as defined by Chothia and Lesk (Chothia and Lesk, 1986, EMBO Journal 5, 823-826) can be used.

These sequences were processed and substitutions scored according to a modified version of the scheme shown in FIG. 3. The modified process is shown in FIG. 27.

Rule 1a. Align the sequences using kabat numbering and select all substitutions found in any of the germline sequences. Classify the substitutions into two categories: (i) substitutions found in the framework region and (ii) substitutions found in the CDR.

Rule 1b. Reconstruct a phylogenetic tree using the Clustal W software based on the amino acid alignment in the framework region. For each substitution, calculate the evolutionary proximity of the closest germline in which that substitution occurs. The evolutionary proximity (EP) is calculated as described in Section 6.3.

Rule 1c. For each substitution in the framework group and in the CDR, calculate the favorability of that substitution using a PAM100 matrix.

$$SM=PAM(A_o,A_s)/10$$

where, $A_o$ is the original amino acid at a position, $A_s$ is the substitution amino acid, and $PAM(A_o, A_s)$ is a measure of the average probability that $A_o$ is substituted with $A_s$ in a large set of protein homolog families.

Rule 2b. For each position, calculate the site heterogeneity, that is a measure of the number of different amino acids present at that position. The site heterogeneity is calculated as the number of different amino acids seen at a position in the set of homologs (SH).

Rule 3b. For each position calculate the site entropy SE as described in Section 6.3.

Rule 4b. For each substitution count the number of times it occurs in the set of homologs (SN)

The total score is then calculated for framework and CDR region substitutions as follows:

$$Score_{FW}=f(EP) \times f(SH) \times f(SE) \times f(SN) \times f(SM),$$

where f( ) is a mathematical function. In this case the function was the parameter in the parentheses multiplied by 1, but the use of functions allows different weights to be applied in subsequent cycles.

$Score_{CDR}$=f'(SE)×f'(SN)×f'(SM), where f'( ) is a mathematical function. In this case the function f'( ) was the parameter in the parentheses multiplied by 1, but the use of functions f'( ) allows different weights to be applied in subsequent cycles.

Based in the above scores, twenty substitutions in both the CDR and framework were identified. The results of using this substitution-scoring scheme is shown in Table 3:

TABLE 3

| Framework substitutions | |
|---|---|
| K78R | 0.465651 |
| H73Q | 0.398614 |
| S79A | 0.389751 |

TABLE 3-continued

| | |
|---|---|
| L08V | 0.352089 |
| S24T | 0.345752 |
| L01V | 0.338391 |
| S20A | 0.337918 |
| G26S | 0.337206 |
| D27S | 0.333916 |
| V45I | 0.321903 |
| L42V | 0.311439 |
| C19A | 0.280519 |
| S68N | 0.279479 |
| M74L | 0.258614 |
| N75S | 0.254877 |
| I69T | 0.243678 |
| T21S | 0.238389 |
| R13S | 0.227712 |
| V86R | 0.221026 |
| G85A | 0.21849 |

CDR substitutions

| | |
|---|---|
| V30M | 35.63365 |
| D65N | 35.55048 |
| G51S | 32.24937 |
| N31S | 30.06633 |
| L52aY | 30.05984 |
| L52aN | 9.380159 |
| N31H | 25.66902 |
| E56K | 25.53363 |
| D65T | 22.22917 |
| F33V | 21.71887 |
| A53D | 21.88011 |
| A53P | 19.17291 |
| A53Q | 12.47777 |
| F59V | 16.86972 |
| V55L | 16.06146 |
| G51N | 13.5927 |
| E56Q | 11.17192 |
| V55F | 10.78488 |
| F33I | 9.900269 |
| S62T | 8.950517 |

A set of forty variants were then designed with the following criteria:

1. Include five substitutions in each variant
2. Maximize the number of different pairs of substitutions that occur. If each variant contains five substitutions, it contains ten sets of pairs. There is thus a maximum of 400 pairs represented in forty variants. The variant set below was optimally design to maximize the number of pairs observed.

In addition, the relative number of framework versus CDR substitution can be modulated. A maximum number of framework and/or CDR substitutions in a variant is set.

This set was calculated by in silico evolution. An initial set of variants each containing five substitutions was randomly chosen. Substitutions were then altered randomly. If a change increased the number of substitution pairs in the variant set it was accepted. Otherwise it was rejected. The process continued for 10,000 iterations. The final set of variants is shown in Table 4.

TABLE 4

| | | | | | |
|---|---|---|---|---|---|
| Variant-1 | L01V | S20A | G26S | T21S | F59V |
| Variant-2 | S20A | L42V | C19A | S68N | G85A |
| Variant-3 | S79A | L08V | L01V | R13S | G85A |
| Variant-4 | S79A | N75S | V30M | F59V | V55F |
| Variant-5 | N31S | C19A | E56K | A53D | V86R |
| Variant-6 | H73Q | S68N | R13S | V30M | A53P |
| Variant-7 | K78R | M74L | V86R | G85A | G51N |
| Variant-8 | L08V | S20A | L52aN | G51N | F33I |
| Variant-9 | V45I | C19A | D65N | L52aN | N31S |
| Variant-10 | G26S | M74L | N75S | R13S | A53Q |
| Variant-11 | L01V | V86R | L52aN | A53D | V55L |
| Variant-12 | L42V | N31S | L52aY | G51S | F59V |
| Variant-13 | L08V | D65T | A53D | L52aY | F33V |
| Variant-14 | S68N | G51S | F59V | V55L | F33I |
| Variant-15 | K78R | H73Q | S79A | L52aY | F33I |
| Variant-16 | G26S | D27S | V45I | G51N | E56Q |
| Variant-17 | K78R | C19A | N75S | I69T | N31H |
| Variant-18 | V45I | T21S | G85A | V30M | V55L |
| Variant-19 | K78R | S20A | D65N | G51S | E56Q |
| Variant-20 | K78R | D27S | D65T | F33V | S62T |
| Variant-21 | S79A | L42V | A53Q | V55L | G51N |
| Variant-22 | M74L | I69T | D65T | E56Q | F33I |
| Variant-23 | S24T | L01V | I69T | G51S | A53P |
| Variant-24 | V45I | L42V | M74L | N31H | A53P |
| Variant-25 | L42V | I69T | T21S | V86R | E56K |
| Variant-26 | S20A | I69T | V30M | N31S | F33V |
| Variant-27 | G26S | S68N | L52aY | E56K | D65T |
| Variant-28 | C19A | V86R | F33V | A53Q | F59V |
| Variant-29 | H73Q | L08V | N31H | V55L | S62T |
| Variant-30 | K78R | L08V | G26S | N31S | V55F |
| Variant-31 | S20A | D27S | E56K | A53Q | V55F |
| Variant-32 | S79A | S24T | S68N | T21S | A53D |
| Variant-33 | L42V | R13S | D65N | V55F | F33I |
| Variant-34 | D27S | G85A | G51S | L52aN | N31H |
| Variant-35 | N75S | T21S | F33V | A53P | S62T |
| Variant-36 | R13S | L52aY | F33V | V55L | E56Q |
| Variant-37 | L01V | V45I | S68N | V55F | S62T |
| Variant-38 | L08V | S24T | C19A | V30M | E56Q |
| Variant-39 | S79A | D27S | C19A | M74L | N31S |
| Variant-40 | H73Q | S24T | D27S | V86R | D65N |

6.5 Identifying a Set of Substitutions and Defining a Set of Variants Representing that Sequence Space for Humanizing Murine Antibody RSV19

In this example, a humanization procedure for a murine antibody RSV19 that binds and neutralize RSV (Respiratory Syncytial Virus) is illustrated. A significant benefit of the computational antibody design system using the methods described in this invention is that only small numbers of variants will be synthesized and tested. This allows the use of functional tests that are more complicated than selection for binding. Antibody humanization is an important antibody function but the sequence and structural determinants are poorly understood.

The methods used to identify substitutions in the framework and CDR regions of the heavy chain of the RSV-19 antibody sequence are as follows. The sequence of the heavy chain of the RSV-19 antibody was aligned using the kabat numbering system with germline human ig heavy chain sequences retrieved from VBase database This alignment may not limited to germline human sequences. Alternatively, all human antibody sequences that are in the same structural class as Im-1 as defined by Chothia and Lesk (Chothia and Lesk, 1986, EMBO Journal 5, 823-826) can be used. A total of 45 sequences were aligned.

The sequences were processed and substitutions scored according to a modified version of the scheme shown in FIG. 3. The modified process is shown in FIG. 28.

Rule 1a. Align sequences using kabat numbering and select all substitutions found in any of the germline sequences. Classify the substitutions into two categories: (i) substitutions found in the framework region and (ii) substitutions found in the CDR. Select only these substitutions and consider them separately.

Rule 1b. Reconstruct a phylogenetic tree using the Clustal W software based on the amino acid alignment in the framework region. For each substitution, calculate the evolutionary proximity of the closest germline in which that substitution occurs. The evolutionary proximity (EP) is calculated, where EP is as defined in Section 6.3.

Rule 1c. For each substitution in the framework group and in the CDR, calculate the favorability of that substitution using a PAM100 matrix. SM is as defined in Section 6.4.

Rule 2b. For each position calculate the site heterogeneity, that is a measure of the number of different amino acids present at that position. The site heterogeneity is calculated as the number of different amino acids seen at a position in the set of homologs (SH).

Rule 3b. For each position calculate the site entropy SE using the algorithm describe in Section 6.3.

Rule 4b. For each substitution, count the number of times it occurs in the set of homologs (SN).

The total score is then calculated for framework and CDR region substitutions as follows:

$$Score_{FW} = f(EP) \times f(SH) \times f(SE) \times f(SN) \times f(SM),$$

where f( ) is a mathematical function. In this case the function was the parameter in the parentheses multiplied by 1, but the use of functions allows different weights to be applied in subsequent cycles.

$$Score_{CDR} = f'(SE) \times f'(SN) \times f'(SM),$$

where f'( ) is a mathematical function. In this case the function was the parameter in the parentheses multiplied by 1, but the use of functions allows different weights to be applied in subsequent cycles.

Based on the above scores, twenty substitutions in both the CDR and the framework were identified. The results of using this substitution-scoring scheme are shown in Table 5:

TABLE 5

| Framework substitutions | |
|---|---|
| I46V | 0.389716 |
| K19R | 0.364451 |
| D69N | 0.330972 |
| R13K | 0.314539 |
| T82aA | 0.304669 |
| I29F | 0.275096 |
| N73T | 0.270393 |
| S71K | 0.268009 |
| T70S | 0.264867 |
| A16G | 0.262967 |
| A85V | 0.261951 |
| S72N | 0.258769 |
| T66S | 0.253018 |
| T23A | 0.2495 |
| N90R | 0.249449 |
| A67R | 0.24173 |
| Q41K | 0.22512 |
| D69T | 0.218449 |
| N28T | 0.217729 |
| R38A | 0.215293 |

| CDR substitutions | |
|---|---|
| D31S | 30.52868 |
| V53T | 28.91288 |
| D52cS | 28.58028 |
| N52aS | 26.10288 |
| M35bV | 25.5501 |
| K30S | 24.93946 |
| Q54Y | 23.36634 |
| Q60K | 23.19751 |
| D52bG | 22.92382 |
| H35S | 21.86205 |
| E52D | 20.6664 |
| D50S | 20.49003 |
| M65I | 20.19161 |
| N52aG | 20.19023 |
| A63V | 19.17104 |
| K58S | 18.77169 |
| E52S | 18.50896 |
| F59V | 18.24618 |

TABLE 5-continued

| | |
|---|---|
| D52cN | 17.85268 |
| P57D | 17.60608 |

A set of forty variants were then designed with the following criteria:

1. Include four to six substitutions in each variant
2. Maximize the number of different pairs of substitutions that occur. If each variant contains five substitutions, it contains ten sets of pairs. There is thus a maximum of 400 pairs represented in forty variants. The variant set below was optimally designed using the evolutionary algorithm to maximize the number of pairs observed.

In addition, the relative number of framework versus CDR substitution can be modulated. A maximum number of framework and/or CDR substitutions in a variant can be set. For humanization, substitutions of human residues in framework regions are preferred. Substitutions in the CDR are designed to retain the activity while changing the amino acid in framework region more biased towards human sequences.

This set was calculated by in silico evolution. An initial set of variants each containing five substitutions was chosen randomly. Substitutions were then altered randomly. If a change increased the number of substitution pairs in the variant set it was accepted. Otherwise it was rejected. The process continued for 10000 iterations. The final set of variants is shown in Table 6.

TABLE 6

| | | | | | |
|---|---|---|---|---|---|
| Variant-1 | I29F | N73T | S71K | Q41K | N52aG |
| Variant-2 | N73T | A85V | S72N | T66S | R38A |
| Variant-3 | D69N | R13K | I29F | D69T | R38A |
| Variant-4 | D69N | N90R | D31S | N52aG | F59V |
| Variant-5 | N52aS | Q54Y | Q60K | H35S | E52S |
| Variant-6 | K19R | T66S | D69T | D31S | D50S |
| Variant-7 | I46V | T23A | N28T | R38A | K58S |
| Variant-8 | R13K | N73T | K30S | K58S | D52cN |
| Variant-9 | A16G | S72N | V53T | K30S | D52bG |
| Variant-10 | S71K | T23A | N90R | D69T | M65I |
| Variant-11 | I29F | N28T | K30S | H35S | A63V |
| Variant-12 | A85V | N52aS | M35bV | K30S | D31S |
| Variant-13 | R13K | D52bG | H35S | D50S | M65I |
| Variant-14 | T66S | D52cS | N52aG | A63V | D50S |
| Variant-15 | I46V | K19R | D69N | M35bV | D52cN |
| Variant-16 | S71K | T70S | A16G | K58S | E52S |
| Variant-17 | I46V | S72N | N90R | A67R | Q54Y |
| Variant-18 | A16G | Q41K | R38A | D31S | A63V |
| Variant-19 | I46V | N73T | V53T | D52cS | E52S |
| Variant-20 | I46V | T70S | D52bG | E52D | P57D |
| Variant-21 | D69N | A85V | M65I | A63V | K58S |
| Variant-22 | T23A | A67R | D52bG | E52S | D52cN |
| Variant-23 | T82aA | I29F | A67R | D52cS | D50S |
| Variant-24 | A16G | A85V | T23A | Q54Y | D50S |
| Variant-25 | A85V | A67R | Q41K | N28T | Q60K |
| Variant-26 | N73T | A67R | D31S | N52aS | E52D |
| Variant-27 | S71K | T66S | M35bV | Q60K | D52bG |
| Variant-28 | S72N | N28T | E52D | M65I | N52aG |
| Variant-29 | K19R | R13K | Q54Y | A63V | P57D |
| Variant-30 | I46V | R13K | S71K | N52aS | F59V |
| Variant-31 | N73T | T70S | Q60K | M65I | F59V |
| Variant-32 | D69N | T82aA | T66S | Q41K | H35S |
| Variant-33 | A85V | D69T | V53T | F59V | D52cN |
| Variant-34 | T70S | R38A | D52cS | K30S | Q54Y |
| Variant-35 | N90R | Q41K | E52D | D50S | D52cN |
| Variant-36 | D69T | M35bV | E52D | A63V | P57D |
| Variant-37 | I29F | A16G | T66S | F59V | P57D |
| Variant-38 | R13K | T82aA | S72N | D31S | E52S |
| Variant-39 | D69N | T70S | S72N | T23A | N52aS |
| Variant-40 | K19R | T82aA | T70S | N28T | V53T |

6.6 Optimization with One Set of Substitutions

One embodiment of the present invention provides the following method.
a) Identify substitutions using a combination of rules (FIG. 2, step 2).
b) Design a set of variants incorporating these substitutions (FIG. 2, step 3).
c) Synthesize and test the set of variants (FIG. 2, step 4).
d) Model sequence-activity relationships and assign values (e.g. regression coefficients) to the substitutions or combinations of substitutions in the variant set (FIG. 2, steps 5 and 6).
e) Design a new set of variants using only the substitutions already tested, in combinations calculated to be advantageous from the values (e.g. regression coefficients) derived from the sequence activity model (FIG. 2, step 7).
f) Repeat steps c-e until a biopolymer with the desired properties has been obtained (FIG. 2 step 8).

6.7 Optimization with One Set of Substitutions and Adjustable Parameters for Sequence-Activity Modeling One embodiment of the present invention provides the following method.
a) Identify substitutions using a combination of rules (FIG. 2, step 2).
b) Design a set of variants incorporating these substitutions (FIG. 2, step 3).
c) Synthesize and test the set of variants (FIG. 2, step 4)
d) Model sequence-activity relationship and assign values (e.g. regression coefficients) to the substitutions or combinations of substitutions in the variant set (FIG. 2, steps 5 and 6).
e) Design a new set of variants using only the substitutions already tested, in combinations calculated to be advantageous from the values (e.g. regression coefficients) derived from the sequence-activity model (FIG. 2, step 7).
f) Repeat steps c-e. However, for each new set of variants that is synthesized and tested, compare the measured activity values for each variant with the values predicted by each sequence-activity correlating method. Use this information to weight and combine the different sequence-activity modeling methods so that the predictions more closely match the measured values. (FIG. 2, step 10)
h) Repeat f) until a biopolymer with the desired properties has been obtained (FIG. 2, step 8).

6.8 Optimization with More than One Set of Substitutions

One embodiment of the present invention provides the following method.
a) Identify substitutions using a combination of rules (FIG. 2, step 2).
b) Design a set of variants incorporating these substitutions (FIG. 2, step 3).
c) Synthesize the set of variants and test (FIG. 2, step 4).
d) Model sequence-activity relationship and assign values (e.g. regression coefficients) to the substitutions or combinations of substitutions in the variant set (FIG. 2, steps 5 and 6).
e) Design a new set of variants using the substitutions already tested, in combinations calculated to be advantageous from the values (e.g. regression coefficients) derived from the sequence activity model (FIG. 2, step 7) and additional new substitutions from step a).
f) Repeat steps a-e until a biopolymer with the desired properties has been obtained (FIG. 2, step 8).

6.9 Optimization with More than One Set of Substitutions and Adjustable Parameters for Sequence-Activity Modeling One embodiment of the present invention provides the following method.
a) Identify substitutions using a combination of rules (FIG. 2, step 2).
b) Design a set of variants incorporating these substitutions (FIG. 2, step 3).
c) Synthesize the set of variants and test (FIG. 2, step 4).
d) Model sequence-activity relationship and assign values (e.g. regression coefficients) to the substitutions or combinations of substitutions in the variant set (FIG. 2, steps 5 and 6).
e) Design a new set of variants using the substitutions already tested, in combinations calculated to be advantageous from the values (e.g. regression coefficients) derived from the sequence activity model (FIG. 2, step 7) and additional new substitutions from step a).
f) Repeat steps c)-e). For each new set of variants that are synthesized and tested, compare the measured activity values for each variant with the values predicted by each sequence-activity correlating method. Use this information to weight and combine the different sequence-activity modeling methods so that the predictions more closely match the measured values. (FIG. 2, step 10).
g) Repeat f) until a biopolymer with the desired properties has been obtained (FIG. 2, step 8).

6.10 Optimization with More than One Set of Substitutions and Adjustable Parameters for Initial Substitution Selection One embodiment of the present invention provides the following method.
a) Identify substitutions using a combination of rules (FIG. 2, step 2).
b) Design a set of variants incorporating these substitutions (FIG. 2, step 3).
c) Synthesize and test the set of variants (FIG. 2, step 4).
d) Model the sequence-activity relationship of the set of variants and assign values (e.g. regression coefficients) to the substitutions or combinations of substitutions in the variant set (FIG. 2, steps 5 and 6).
e) For each substitution or group of substitutions, compare the activity values assigned from the sequence-activity correlation (e.g. the experimentally determined contributions) with the score obtained by the combination of rules (e.g. the predicted contributions). Use this information to weight and combine the different substitution selection rules/methods so that the predictions more closely match the values derived from the sequence-activity relationship (FIG. 2, step 9).
f) Design a new set of variants using the substitutions already tested, in combinations calculated to be advantageous from the values (e.g. regression coefficients) derived from the sequence activity model (FIG. 2, step 7) and additional new substitutions from a).
g) Repeat steps a-f until a biopolymer with the desired properties has been obtained (FIG. 2, step 8).

6.11 Optimization with More than One Set of Substitutions and Adjustable Parameters for Initial Substitution Selection and Sequence-Activity Modeling One embodiment of the present invention provides the following method.
a) Identify substitutions using a combination of rules (FIG. 2, step 2).
b) Design a set of variants incorporating these substitutions (FIG. 2, step 3).

c) Synthesize the set of variants and test (FIG. 2, step 4).

d) Model sequence-activity relationship and assign values (e.g. regression coefficients) to the substitutions or combinations of substitutions (FIG. 2, steps 5 and 6).

e) For each substitution or group of substitutions, compare the activity values assigned from the sequence-activity correlation (e.g. the experimentally determined contributions) with the score obtained by the combination of rules (e.g., the predicted contributions). Use this information to weight and combine the different substitution selection rules/methods so that the predictions more closely match the values derived from the sequence-activity relationship (FIG. 2, step 9).

f) Design a new set of variants using the substitutions already tested, in combinations calculated to be advantageous from the values (e.g. regression coefficients) derived from the sequence activity model (FIG. 2, step 7) and additional new substitutions from step a).

g) For each new set of variants that are synthesized and tested, compare the measured activity values for each variant with the values predicted by each sequence-activity correlating method. Use this information to weight and combine the different sequence-activity modeling methods so that the predictions more closely match the measured values (FIG. 2, step 10).

h) Repeat steps a)-f) until a biopolymer with the desired properties has been obtained (FIG. 2, step 8).

6.12 System with Adjustable Parameters for Initial Substitution Selection

One embodiment of the present invention provides the following method.

a) Perform the process of FIG. 2/e.g. Method X.5 multiple times using different biopolymer targets.

b) For each substitution or group of substitutions, compare the activity values assigned from the sequence-activity correlation (e.g., the experimentally determined contributions) with the score obtained by the combination of rules (e.g., the predicted contributions).

c) Use the information from b) to weight and combine the different substitution selection rules/methods so that the predictions more closely match the values derived from the sequence-activity relationship (FIG. 2, step 9).

d) Compile a general set of weights and combinations of substitution selection rules/methods for use with a biopolymer class (e.g., protein/nucleic acid/polyketide) AND/OR compile a specific set of weights and combinations of substitution selection rules/methods for use with a biopolymer subclass (e.g., kinase, antibody, promoter sequence, intron, type II polyketide, terpene) AND/OR compile a specific set of weights and combinations of substitution selection rules/methods for use with a biopolymer class and property (ie thermostability of polypeptides, pH optimum of enzymes, promoter activity in *E coli*, polyketide activity towards tumor killing).

6.13 System with Adjustable Parameters for Sequence-Activity Analysis

One embodiment of the present invention provides the following method.

a) Perform the process of FIG. 2 (e.g. methods 8.2 or 8.4 multiple times using different biopolymer targets).

b) For each new set of variants that are synthesized and tested, compare the measured activity values for each variant with the values predicted by each sequence-activity correlating method.

c) Use the information from b) to weight and combine the different sequence-activity modeling methods so that the predictions more closely match the measured values (FIG. 2, step 10).

d) Compile a general set of weights and combinations of sequence-activity modeling methods for use with a biopolymer class (e.g., protein/nucleic acid/polyketide) AND/OR compile a specific set of weights and combinations of sequence-activity modeling methods for use with a biopolymer subclass (e.g., kinase, antibody, promoter sequence, intron, type II polyketide, terpene, etc.) AND/OR compile a specific set of weights and combinations of sequence-activity modeling methods for use with a biopolymer class and property (e.g., thermostability of polypeptides, pH optimum of enzymes, promoter activity in *E coli*, polyketide activity towards tumor killing).

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Aspects of the present invention can be implemented as a computer program product that comprises a computer program mechanism embedded in a computer readable storage medium. For instance, the computer program product could contain the program modules and/or data structures shown in FIG. 1. These program modules may be stored on a CD-ROM, magnetic disk storage product, digital video disk (DVD) or any other computer readable data or program storage product. The software modules in the computer program product may also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for constructing a variant set for modifying a biopolymer of interest, the method comprising:
   a) identifying a plurality of positions in said biopolymer of interest and, for each respective position in said plurality of positions, one or more substitutions for the respective position, wherein the plurality of positions and the one or more substitutions for each respective position in the plurality of positions collectively define a biopolymer sequence space;
   b) selecting a first plurality of variants of the biopolymer of interest thereby forming a variant set, wherein said variant set comprises a subset of said biopolymer sequence space;
   c) measuring a property of all or a portion of the variants in the variant set; and
   d) modeling, using a suitably programmed computer, a sequence-activity relationship between (i) one or more substitutions at one or more positions of the biopolymer of interest represented by the variant set and (ii) the property measured for all or the portion of the variants in the variant set, wherein the sequence-activity relationship has the form $$Y=f(w_1x_1, w_2x_2, \ldots w_ix_i)$$

wherein,

Y is a quantitative measure of the property;

$x_i$ is a descriptor of a substitution, a combination of substitutions, or a component of one or more substitutions, at one or more positions in the plurality of positions;

$w_i$ is a weight applied to the descriptor $x_i$; and f( ) is a mathematical function, and wherein the modeling comprises:

i) optimizing, using a suitably programmed computer, the sequence-activity relationship by adjusting individual weights $w_i$ for each said descriptor $x_i$ using a refinement algorithm that minimizes the difference between the predicted values and the real values of Y from partial data, wherein the partial data is the first plurality of variants with either (1) individual sequences left out on a random basis or (2) individual substitutions at positions in the plurality of positions left out on a random basis, and ii) repeating the optimizing i) a plurality of times thereby obtaining, for each respective substitution or combination of substitutions $x_i$, (a) an average value for the weight $w_i$ describing a relative or absolute contribution of the respective substitution or combination of substitutions $x_i$ to Y, and (b) a standard deviation, variance or other measure of confidence in the weight $w_i$ describing the relative or absolute contribution of the respective substitution or combination of substitutions $x_i$ to Y.

2. The method of claim 1, the method further comprising:

e) defining a new variant set for the biopolymer of interest that comprises variants that include substitutions in the plurality of positions that are selected based on a function of the sequence-activity relationship.

3. The method of claim 2, the method further comprising:

f) measuring a property of all or a portion of the variants in the new variant set.

4. The method of claim 3, the method further comprising repeating steps b) through f), until a variant in the new variant set exhibits a value for the property that exceeds a predetermined value.

5. The method of claim 4, wherein the predetermined value is a value that is greater than the value for the property that is exhibited by the biopolymer of interest.

6. The method of claim 3, the method further comprising repeating steps b) though f), until a variant in the variant set exhibits a value for the property that is less than a predetermined value.

7. The method of claim 6, wherein the predetermined value is a value that is less than the value for the property that is exhibited by the biopolymer of interest.

8. The method of claim 2, wherein the new variant set comprises variants of the biopolymer that have one or more substitutions at one or more positions that are not encompassed by the biopolymer sequence space of step a).

9. The method of claim 2, wherein variants in the new variant set differ by fewer than 5 substitutions from at least one biopolymer for which the property has already been measured.

10. The method of claim 2, wherein the plurality of positions and the one or more substitutions for each respective position in the plurality of positions are identified using a plurality of rules; and wherein the contribution of each respective rule in the plurality of rules to the biopolymer sequence space is independently weighted by a rule weight in a plurality of rule weights corresponding to the respective rule; and the method further comprises, prior to the defining of a new variant set step e), the steps of:

adjusting one or more rule weights in the plurality of rule weights based on a comparison, for each respective substitution at each position in the plurality of positions in the variant set, (i) a value derived for the respective substitution at each position in the plurality of positions from the sequence-activity relationship, and (ii) a score assigned by the plurality of rules to the respective substitution at each position in the plurality of positions; and repeating the identifying step using the rule weights, thereby redefining the plurality of positions and, for each respective position in the plurality of positions, redefining the one or more substitutions for the respective position; and wherein the defining of a new variant set step e) further comprises redefining the variant set to comprise one or more variants each having a substitution in a position in the redefined plurality of positions not present in any variant in the variant set selected by the initial selecting step b).

11. The method of claim 2 wherein the modeling a sequence-activity relationship d) further comprises modeling a plurality of sequence-activity relationships, wherein each respective sequence-activity relationship in the plurality of sequence-activity relationships describes the relationship between (i) one or more substitutions at one or more positions of the biopolymer of interest represented by the variant set and (ii) the property measured for all or the portion of the variants in the variant set; and the defining the new variant set e) comprises redefining the variant set to comprise variants that include substitutions in the plurality of positions that are selected based on a combination function of the plurality of sequence-activity relationships.

12. The method of claim 2 wherein the function f is a linear combination of the $x_i$ and the sequence-activity relationship has the form:

$$Y=w_1x_1+w_2x_2+\ldots+w_ix_i.$$

13. The method of claim 12 wherein a respective $x_i$ in the sequence-activity relationship is a descriptor of a substitution or a combination of substitutions and wherein the substitution or combination of substitutions is selected for the new variant set for the biopolymer of interest when the weight $w_i$ corresponding to the respective $x_i$ is positive.

14. The method of claim 13 wherein the weight $w_i$ corresponding to the respective $x_i$ is at least one standard deviation above neutrality.

15. The method of claim 13 wherein the substitution or combination of substitutions has been tested at least three times.

16. The method of claim 1, wherein the plurality of positions and the one or more substitutions for each respective position in the plurality of positions are identified using a plurality of rules.

17. The method of claim 16, wherein the plurality of rules comprises two or more rules selected from the group consisting of:

(i) the favorability of a substitution calculated from a substitution matrix;

(ii) the probability of a substitution calculated from a conservation index;
(iii) the proximity of a position to a structurally defined region within the biopolymer;
(iv) the presence of a substitution in a homologous biopolymer;
(v) the favorability of a substitution calculated from a comparison of homologous sequences;
(vi) the mutability of a position calculated from a comparison of homologous sequences;
(vii) the favorability of a substitution calculated from a comparison of homologous structures; and
(viii) the mutability of a position calculated from a comparison of homologous structures.

18. The method of claim 16, wherein the plurality of rules comprises five or more rules.

19. The method of claim 16, wherein
(A) the identifying combines a score from each rule in the plurality of rules thereby forming a cumulative score for each respective substitution at each position in the plurality of positions by summing the score from each rule in the plurality of rules for each respective substitution at each position in the plurality of positions, and
(B) the cumulative score for each respective substitution at each position in the plurality of positions is rank ordered.

20. The method of claim 19, wherein the combining comprises adding (i) a first score from a first rule in the plurality rules and (ii) a second score from a second rule in the plurality rules for the variant of a biopolymer of interest.

21. The method of claim 19, wherein
(A) the identifying combines a score from each rule in the plurality of rules thereby forming a cumulative score for each respective substitution at each position in the plurality of positions wherein the forming the cumulative score comprises multiplying (i) a first score from a first rule in the plurality rules and (ii) a second score from a second rule in the plurality rules for each respective substitution at each position in the plurality of positions, and
(B) the cumulative score for each respective substitution at each position in the plurality of positions is rank ordered.

22. The method of claim 1, wherein the variant set is enriched for pairwise uniqueness of substitutions at positions in the plurality of positions.

23. The method of claim 1, wherein the variant set consists of fewer than 1000 variants.

24. The method of claim 1, wherein the variant set consists of fewer than 250 variants.

25. The method of claim 1, wherein the variant set consists of fewer than 100 variants.

26. The method of claim 1, wherein variants in the variant set contain fewer than 5 substitutions.

27. The method of claim 1, wherein the modeling comprises least square regression, linear regression, non-linear regression, logistic regression, or partial least squares projection to latent variables.

28. The method of claim 1, wherein the modeling step d) comprises:
computation of a neural network, computation of a Bayesian model, a generalized additive model, a support vector machine, machine learning, or classification using a regression tree using, as input to the modeling, (i) the one or more substitutions at the one or more positions of the biopolymer of interest represented by the variant set and (ii) the property measured for the variants in the variant set, and
obtaining, as output to the modeling, a predicted value for the property.

29. The method of claim 1, wherein the modeling step d) comprises boosting or adaptive boosting.

30. The method of claim 1, wherein the biopolymer of interest is a polypeptide, a polynucleotide, a small inhibitory RNA molecule (siRNA), or a polyketide.

31. The method of claim 1, wherein the biopolymer of interest is a protein kinase, a protein phosphatase, a protease, a receptor, a G-protein coupled receptor, a cytokine, a growth factor or an antigen from an infectious pathogen.

32. The method of claim 1, wherein the biopolymer of interest is a cytochrome P450, a lipase, an esterase, a peptidase, a transferase, a polymerase, or a depolymerase.

33. The method of claim 1, wherein the plurality of positions comprises five or more positions.

34. The method of claim 1, wherein the plurality of positions comprises ten or more positions.

35. The method of claim 1, wherein the selecting the first plurality of variants step b) comprises applying a monte carlo algorithm, a genetic algorithm, or a combination thereof, to construct the variant set, with the provisos that:
(i) each variant in all or portion of the variant set has a number of substitutions that is between a first value and a second value; and
(ii) a number of different pairs of substitutions collectively represented by the variant set is above a predetermined number.

36. The method of claim 35, wherein the first value is two substitutions and the second value is twenty substitutions.

37. The method of claim 35, wherein the first value is four substitutions and the second value is ten substitutions.

38. The method of claim 35, wherein the predetermined number is one hundred.

39. The method of claim 35, wherein the predetermined number is thirty.

40. The method of claim 1 wherein
the measuring step c) comprises synthesizing all or the portion of the variants in the variant set, and wherein
the property of a variant in the variant set is an antigenicity of the variant, an immunogenicity of the variant, an immunomodulatory activity of the variant, a catalysis of a chemical reaction by the variant, a thermostability of the variant, a level of expression of the variant in a host cell, a susceptibility of the variant to a post-translational modification, a killing of pathogenic organisms or viruses resulting from activity of the variant or a modulation of a signaling pathway by the variant.

41. The method of claim 1, wherein each variant in the first plurality of variants is selected on a predetermined basis.

42. The method of claim 1, wherein the value quantifying the confidence with which a substitution in the one or more substitutions of a position in the one or more positions of the biopolymer of interest contributes to the measured property is determined by the method of:
(i) calculating a plurality of sequence activity relationships, wherein each sequence activity relationship in the plurality of sequence activity relationships is calculated using the measured property of each variant in an independent subset of the variant set;

(ii) calculating, for each sequence activity relationship in said plurality of sequence activity relationships, a value for the contribution to the measured property by the substitution in the position; and (iii) calculating a confidence for the value for the contribution to the measured property by the substitution in the position using each said value computed in said calculating step (ii).

43. The method of claim 1 implemented on a computer.

44. A computer program product encoding instructions for implementing the method according to claim 1.

* * * * *

SEQUENCE LISTING

```
<160> NUMBER OF SEQ ID NOS: 3

<210> SEQ ID NO 1
<211> LENGTH: 20
<212> TYPE: PRT
```

-continued

<213> ORGANISM: Escheria coli
<220> FEATURE:
<223> OTHER INFORMATION: Escheria coli Leader Peptide

<400> SEQUENCE: 1

```
Met Lys Lys Leu Leu Phe Ala Ile Pro Leu Val Val Pro Phe Tyr Ser
 1               5                  10                  15

His Ser Thr Met
         20
```

<210> SEQ ID NO 2
<211> LENGTH: 377
<212> TYPE: PRT
<213> ORGANISM: Tritirachium album Limber
<220> FEATURE:
<223> OTHER INFORMATION: Tritirachium album Limber proteinase K

<400> SEQUENCE: 2

```
Ala Pro Ala Val Glu Gln Arg Ser Glu Ala Ala Pro Leu Ile Glu Ala
 1               5                  10                  15

Arg Gly Glu Met Val Ala Asn Lys Tyr Ile Val Lys Phe Lys Glu Gly
                20                  25                  30

Ser Ala Leu Ser Ala Leu Asp Ala Ala Met Glu Lys Ile Ser Gly Lys
            35                  40                  45

Pro Asp His Val Tyr Lys Asn Val Phe Ser Gly Phe Ala Ala Thr Leu
    50                  55                  60

Asp Glu Asn Met Val Arg Val Leu Arg Ala His Pro Asp Val Glu Tyr
65                  70                  75                  80

Ile Glu Gln Asp Ala Val Val Thr Ile Asn Ala Ala Gln Thr Asn Ala
                85                  90                  95

Pro Trp Gly Leu Ala Arg Ile Ser Ser Thr Ser Pro Gly Thr Ser Thr
            100                 105                 110

Tyr Tyr Tyr Asp Glu Ser Ala Gly Gln Gly Ser Cys Val Tyr Val Ile
    115                 120                 125

Asp Thr Gly Ile Glu Ala Ser His Pro Glu Phe Glu Gly Arg Ala Gln
130                 135                 140

Met Val Lys Thr Tyr Tyr Tyr Ser Ser Arg Asp Gly Asn Gly His Gly
145                 150                 155                 160

Thr His Cys Ala Gly Thr Val Gly Ser Arg Thr Tyr Gly Val Ala Lys
                165                 170                 175

Lys Thr Gln Leu Phe Gly Val Lys Val Leu Asp Asp Asn Gly Ser Gly
            180                 185                 190

Gln Tyr Ser Thr Ile Ile Ala Gly Met Asp Phe Val Ala Ser Asp Lys
    195                 200                 205

Asn Asn Arg Asn Cys Pro Lys Gly Val Val Ala Ser Leu Ser Leu Gly
    210                 215                 220

Gly Gly Tyr Ser Ser Ser Val Asn Ser Ala Ala Ala Arg Leu Gln Ser
225                 230                 235                 240

Ser Gly Val Met Val Ala Val Ala Ala Gly Asn Asn Asn Ala Asp Ala
                245                 250                 255

Arg Asn Tyr Ser Pro Ala Ser Glu Pro Ser Val Cys Thr Val Gly Ala
            260                 265                 270

Ser Asp Arg Tyr Asp Arg Arg Ser Ser Phe Ser Asn Tyr Gly Ser Val
    275                 280                 285

Leu Asp Ile Phe Gly Pro Gly Thr Ser Ile Leu Ser Thr Trp Ile Gly
    290                 295                 300

Gly Ser Thr Arg Ser Ile Ser Gly Thr Ser Met Ala Thr Pro His Val
```

-continued

```
            305                 310                 315                 320
Ala Gly Leu Ala Ala Tyr Leu Met Thr Leu Gly Lys Thr Thr Ala Ala
                    325                 330                 335

Ser Ala Cys Arg Tyr Ile Ala Asp Thr Ala Asn Lys Gly Asp Leu Ser
                340                 345                 350

Asn Ile Pro Phe Gly Thr Val Asn Leu Leu Ala Tyr Asn Asn Tyr Gln
            355                 360                 365

Ala Val Asp His His His His His His
        370                 375
```

<210> SEQ ID NO 3
<211> LENGTH: 1193
<212> TYPE: DNA
<213> ORGANISM: Artificial Sequence
<220> FEATURE:
<223> OTHER INFORMATION: Artificial nucleic acid sequence encoding
      Tritirachium album Limber proteinase K

<400> SEQUENCE: 3

| | |
|---|---|
| atgaaaaaac tgctgttcgc gattccgctg gtggtgccgt tctatagcca tagcaccatg | 60 |
| gcaccggccg ttgaacagcg ttctgaagca gctcctctga ttgaggcacg tggtgaaatg | 120 |
| gtagcaaaca agtacatcgt gaagttcaag gagggttctg ctctgtctgc tctggatgct | 180 |
| gctatggaaa agatctctgg caagcctgat cacgtctata agaacgtgtt cagcggtttc | 240 |
| gcagcaactc tggacgagaa catggtccgt gtactgcgtg ctcatccaga cgttgaatac | 300 |
| atcgaacagg acgctgtggt tactatcaac gcggcacaga ctaacgcacc ttggggtctg | 360 |
| gcacgtattt cttctacttc cccgggtacg tctacttact actacgacga gtctgccggt | 420 |
| caaggttctt gcgtttacgt gatcgatacg ggcatcgagg cttctcatcc tgagtttgaa | 480 |
| ggccgtgcac aaatggtgaa gacctactac tactcttccc gtgacggtaa tggtcacggt | 540 |
| actcattgcg caggtactgt tggtagccgt acctacggtg ttgctaagaa aacgcaactg | 600 |
| ttcggcgtta aagtgctgga cgacaacggt tctggtcagt actccaccat tatcgcgggt | 660 |
| atggatttcg tagcgagcga taaaaacaac cgcaactgcc cgaaaggtgt tgtggcttct | 720 |
| ctgtctctgg gtggtggtta ctcctcttct gttaacagcg cagctgcacg tctgcaatct | 780 |
| tccggtgtca tggtcgcagt agcagctggt aacaataacg ctgatgcacg caactactct | 840 |
| cctgctagcg agccttctgt ttgcaccgtg ggtgcatctg atcgttatga tcgtcgtagc | 900 |
| tccttcagca actatggttc cgtcctggat atcttcggcc ctggtacttc tatcctgtct | 960 |
| acctggattg gcggtagcac tcgttccatt tccggtacga gcatggctac tccacatgtt | 1020 |
| gctggtctgg cagcatacct gatgaccctg ggtaagacca ctgctgcatc cgcttgtcgt | 1080 |
| tacatcgcgg atactgcgaa caaaggcgat ctgtctaaca tcccgttcgg caccgttaat | 1140 |
| ctgctggcat acaacaacta tcaggctgtc gaccatcatc atcatcatca tag | 1193 |